(12) United States Patent
Wenglowsky et al.

(10) Patent No.: US 11,059,827 B2
(45) Date of Patent: Jul. 13, 2021

(54) COMPOUNDS AND COMPOSITIONS USEFUL FOR TREATING DISORDERS RELATED TO NTRK

(71) Applicant: Blueprint Medicines Corporation, Cambridge, MA (US)

(72) Inventors: Steven Mark Wenglowsky, Cambridge, MA (US); Chandrasekhar V. Miduturu, Cambridge, MA (US); Neil Bifulco, Sudbury, MA (US); Joseph L. Kim, Wayland, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 16/527,773

(22) Filed: Jul. 31, 2019

(65) Prior Publication Data

US 2019/0382410 A1 Dec. 19, 2019

Related U.S. Application Data

(62) Division of application No. 15/355,425, filed on Nov. 18, 2016, now Pat. No. 10,370,379.

(60) Provisional application No. 62/257,476, filed on Nov. 19, 2015.

(51) Int. Cl.
*C07D 487/04* (2006.01)
*A61P 35/02* (2006.01)

(52) U.S. Cl.
CPC ............ *C07D 487/04* (2013.01); *A61P 35/02* (2018.01)

(58) Field of Classification Search
CPC ......................... C07D 487/04; A61K 31/519
USPC ........................................ 544/281; 514/259.3
See application file for complete search history.

(56) References Cited

U.S. PATENT DOCUMENTS

| | | | |
|---|---|---|---|
| 5,251,911 A | 10/1993 | Blake | |
| 8,802,697 B2 | 8/2014 | Bifulco, Jr. et al. | |
| 9,126,951 B2 | 9/2015 | Bifulco, Jr. et al. | |
| 9,200,002 B2 | 12/2015 | Hodous et al. | |
| 9,334,263 B2 | 5/2016 | Hodous et al. | |
| 9,340,514 B2 | 5/2016 | Bifulco, Jr. et al. | |
| 9,434,700 B2 | 9/2016 | Bifulco, Jr. et al. | |
| 9,499,522 B2 | 11/2016 | DiPietro et al. | |
| 9,688,680 B2 | 6/2017 | Hodous | |
| 9,695,165 B2 | 7/2017 | Bifulco, Jr. et al. | |
| 9,884,861 B2 | 2/2018 | Hodous et al. | |
| 9,944,651 B2 | 4/2018 | Hodous et al. | |
| 9,994,552 B2 | 6/2018 | DiPietro et al. | |
| 9,994,575 B2 | 6/2018 | Hodous et al. | |
| 10,000,490 B2 | 6/2018 | Bifulco, Jr. et al. | |
| 10,000,496 B2 | 6/2018 | Hodous et al. | |
| 10,017,512 B2 | 7/2018 | Wenglowsky et al. | |
| 10,030,005 B2 | 7/2018 | Brubaker et al. | |
| 10,035,789 B2 | 7/2018 | Brubaker et al. | |
| 10,139,872 B1 | 11/2018 | Li et al. | |
| 10,196,436 B2 | 2/2019 | Miduturu | |
| 10,202,365 B2 | 2/2019 | Brooijmans et al. | |
| 10,227,329 B2 | 3/2019 | Brubaker et al. | |
| 10,370,379 B2 | 8/2019 | Wenglowsky et al. | |
| 2014/0045779 A1 | 2/2014 | Xu | |
| 2014/0187559 A1 | 7/2014 | Miduturu | |
| 2016/0102097 A1 | 4/2016 | Hodous et al. | |
| 2016/0168156 A1 | 6/2016 | Kim et al. | |
| 2017/0022206 A1 | 1/2017 | Hodous et al. | |
| 2017/0029409 A1 | 2/2017 | DiPietro et al. | |
| 2017/0057953 A1 | 3/2017 | Hodous et al. | |
| 2017/0066773 A1 | 3/2017 | Wenglowsky et al. | |
| 2017/0066812 A1 | 3/2017 | Bifulco, Jr. et al. | |
| 2017/0121312 A1 | 5/2017 | Brubaker et al. | |
| 2017/0174652 A1 | 6/2017 | Bifulco, Jr. et al. | |
| 2017/0204104 A1 | 7/2017 | Hodous et al. | |
| 2017/0253593 A1 | 9/2017 | Bifulco, Jr. et al. | |
| 2017/0267661 A1 | 9/2017 | Kim et al. | |
| 2017/0298069 A1 | 10/2017 | Brooijmans et al. | |
| 2018/0022731 A1 | 1/2018 | Brooijmans et al. | |
| 2018/0022732 A1 | 1/2018 | Brubaker et al. | |
| 2018/0030032 A1 | 2/2018 | Brubaker et al. | |
| 2019/0119280 A1 | 4/2019 | Hodous et al. | |
| 2019/0144454 A1 | 5/2019 | Hodous et al. | |
| 2019/0169194 A1 | 6/2019 | Wenglowsky et al. | |
| 2019/0185454 A1 | 6/2019 | Brubaker et al. | |

FOREIGN PATENT DOCUMENTS

| | | |
|---|---|---|
| CN | 102596957 A | 7/2012 |
| CN | 103965199 A | 8/2014 |
| EP | 2194058 A1 | 6/2010 |
| GB | 2515785 A | 1/2015 |
| JP | 2007-507446 A | 3/2007 |
| JP | 2007-534687 A | 11/2007 |
| JP | 2013-525481 A | 6/2013 |
| JP | 2013-537199 A | 9/2013 |
| RU | 2379308 C2 | 1/2010 |
| WO | 2005/040171 A1 | 5/2005 |
| WO | 2005/117909 A2 | 12/2005 |
| WO | 2009/032694 A1 | 3/2009 |

(Continued)

OTHER PUBLICATIONS

Dowling et al., Potent and Selective Inhibitors of CK2 Kinase Identified through Structure-Guided Hybridization. ACS Med Chem Lett. Jan. 24, 2012;3(4)278-83.

Dowling et al., Structure and Property Based Design of Pyrazolo[1,5-a]pyrimidine Inhibitors of CK2 Kinase with Activity in Vivo. ACS Med Chem Lett. 2013;4(8):800-5.

Dwyer et al., Discovery of pyrazolo[1,5-a]pyrimidine-based CHK1 inhibitors: a template-based approach—part 1. Bioorg Med Chem Lett. Jan. 1, 2011;21(1):467-70.

Radl et al., Synthetic Studies Connected with the Preparation of N-[3-(3-Cyanopyrazolo[1,5-a]Pyrimidin-5-yl)Phenyl]-N-Ethylacetamide, A Zelaplon Regioisomer. Heterocycles. 2010;80(2)1359-1379.

(Continued)

*Primary Examiner* — Susanna Moore

(74) *Attorney, Agent, or Firm* — McCarter & English, LLP; Steven G. Davis; Wei Song

(57) ABSTRACT

This invention relates to inhibitors of NTRK that are active against wild-type NTRK and its resistant mutants.

19 Claims, No Drawings

(56) References Cited

FOREIGN PATENT DOCUMENTS

| | | |
|---|---|---|
| WO | 2010/048314 A1 | 4/2010 |
| WO | 2011/006074 A1 | 1/2011 |
| WO | 2011/139273 A1 | 11/2011 |
| WO | 2012/034091 A1 | 3/2012 |
| WO | 2012/034095 A1 | 3/2012 |
| WO | 2014/036387 A2 | 3/2014 |
| WO | 2014/055955 A1 | 4/2014 |
| WO | 2014/071358 A2 | 5/2014 |
| WO | 2014/118226 A1 | 8/2014 |
| WO | 2014/130375 A1 | 8/2014 |
| WO | 2014/139326 A1 | 9/2014 |
| WO | 2015/157093 A1 | 10/2015 |
| WO | 2016/133838 A1 | 8/2016 |
| WO | 2017/087778 A1 | 5/2017 |
| WO | 2018/049233 A1 | 3/2018 |

OTHER PUBLICATIONS

STN Registry No. 1017684-07-9, 1 page, dated Apr. 28, 2008.
STN Registry No. 1017684-10-4, 1 page, dated Apr. 28, 2008.
STN Registry No. 1017684-13-7, 1 page, dated Apr. 28, 2008.
STN Registry No. 1017684-15-9, 1 page, dated Apr. 28, 2008.
STN Registry No. 1017684-17-1, 1 page, dated Apr. 28, 2008.
STN Registry No. 1224289-06-8, 1 page, dated May 17, 2010.
STN Registry No. 1224289-08-0, 1 page, dated May 17, 2010.
STN Registry No. 1265679-25-1, 1 page, dated Mar. 2, 2011.
STN Registry No. 138904-40-2, 1 page, dated Feb. 14, 1992.
STN Registry No. 138904-41-3, 1 page, dated Feb. 14, 1992.
STN Registry No. 138904-42-4, 1 page, dated Feb. 14, 1992.
STN Registry No. 138904-43-5, 1 page, dated Feb. 14, 1992.
STN Registry No. 138904-44-6, 1 page, dated Feb. 14, 1992.
STN Registry No. 138904-45-7, 1 page, dated Feb. 14, 1992.
STN Registry No. 138904-46-8, 1 page, dated Feb. 14, 1992.
STN Registry No. 140706-37-2, 1 page, dated Apr. 26, 1992.
STN Registry No. 144488-64-2, 1 page, dated Nov. 13, 1992.
Traxler et al., Use of a pharmacophore model for the design of EGF-R tyrosine kinase inhibitors: 4-(phenylamino) pyrazolo[3,4-d]pyrimidines. J Med Chem. Oct. 24, 1997;40(22):3601-16.
International Search Report and Written Opinion for Application No. PCT/US2016/048698, dated Nov. 18, 2016, 11 pages.
International Search Report and Written Opinion for Application No. PCT/US2016/062731, dated Feb. 10, 2017.
Notice of Allowance for U.S. Appl. No. 14/887,614, dated Jan. 17, 2018.
Notice of Allowance for U.S. Appl. No. 15/093,354, dated Sep. 26, 2017.
Notice of Allowance for U.S. Appl. No. 15/217,503, dated Jan. 16, 2018.
Notice of Allowance for U.S. Appl. No. 15/217,503, dated Sep. 5, 2017.
Notice of Allowance for U.S. Appl. No. 15/222,523, dated Oct. 11, 2018.
Notice of Allowance for U.S. Appl. No. 15/248,207, dated Mar. 9, 2018.
Notice of Allowance for U.S. Appl. No. 15/295,450, dated Feb. 14, 2018.
Notice of Allowance for U.S. Appl. No. 15/340,428, dated Feb. 20, 2018.
Notice of Allowance for U.S. Appl. No. 15/340,428, dated Oct. 25, 2017.
Notice of Allowance for U.S. Appl. No. 15/462,255, dated Aug. 6, 2018.
Notice of Allowance for U.S. Appl. No. 15/479,145, dated Nov. 30, 2017.
Notice of Allowance for U.S. Appl. No. 15/488,257, dated Dec. 6, 2018.
Notice of Allowance for U.S. Appl. No. 15/548,925, dated Sep. 21, 2018.
Notice of Allowance for U.S. Appl. No. 15/599,006, dated Feb. 22, 2018.
Notice of Allowance for U.S. Appl. No. 15/657,057, dated Oct. 19, 2018.
Notice of Allowance for U.S. Appl. No. 15/660,840, dated Jan. 17, 2018.
Notice of Allowance for U.S. Appl. No. 15/867,637, dated Sep. 26, 2018.
Singapore Office Action for Application No. 11201803920T, dated Jul. 8, 2019, 13 pages.
U.S. Appl. No. 16/002,587, filed Jun. 7, 2018—Abandoned.
U.S. Appl. No. 15/248,207, filed Aug. 26, 2016, U.S. Pat. No. 10,175,512.
U.S. Appl. No. 16/027,166, filed Jul. 3, 2018, US2019-0169194.
U.S. Appl. No. 15/355,425, filed Nov. 18, 2016, U.S. Pat. No. 10,370,379.
Doebele et al., An Oncogenic NTRK Fusion in a Patient with Soft-Tissue Sarcoma with Response to the Tropomyosin-Related Kinase Inhibitor LOXO-101. Cancer Discov. Oct. 2015;5(10):1049-57.

COMPOUNDS AND COMPOSITIONS USEFUL FOR TREATING DISORDERS RELATED TO NTRK

CROSS-REFERENCE TO RELATED APPLICATIONS

This application is a divisional application of U.S. Ser. No. 15/355,425, filed Nov. 18, 2016, which claims priority from U.S. Ser. No. 62/257,476 filed Nov. 19, 2015. The entire contents of each of the aforementioned applications are incorporated herein by reference.

BACKGROUND

Neurotrophic Tyrosine Receptor Kinase (NTRK) 1, 2 and 3 are receptor tyrosine kinases (RTKs) that activate multiple downstream pathways involved in cell proliferation and survival. Various genetic fusions, arising from aberrant chromosomal translocations of the genes coding for these RTKs, are implicated in the etiology of multiple cancers including high and low grade glioma, cholangiocarcinoma, papillary thyroid carcinoma, colon cancer and non-small cell lung cancer. A genomics analysis on the landscape of kinase fusions identified NTRK fusions in a wide array of additional cancer types including head and neck squamous cell carcinoma, pancreatic adenocarcinoma, sarcoma and melanoma, thereby providing further therapeutic rationale for deploying inhibitors of these kinases to treat multiple oncologic indications.

The identification of NTRK fusions as the underlying cause of certain cancers prompted the discovery and clinical development of several NTRK kinase inhibitors to treat tumors that harbor an NTRK fusion protein. Early clinical data support the viability of this approach in providing benefit to patients with specific human malignancies. Ultimately however, despite clear signs of clinical activity, most patients' cancers will become resistant to kinase inhibitor therapy leading to relapse and progression of the disease. When resistance occurs, the patient's treatment options are often very limited. There is thus a need for compounds that inhibit NTRK, as well as its resistant mutants.

SUMMARY OF THE INVENTION

The present invention provides inhibitors of NTRK and NTRK mutants, e.g., NTRK resistant mutants (as defined herein), for example, inhibitors of structural formula (I) and pharmaceutically acceptable salts and compositions thereof. The present invention further provides methods of using the compounds of the invention, and pharmaceutically acceptable salts and compositions thereof, to inhibit the activity of NTRK or its mutants in a cell or patient. The present invention further provides methods for using the compounds of the invention, and pharmaceutically acceptable salts and compositions thereof, to treat a subject suffering from a condition mediated by aberrant NTRK activity, e.g., cancer.

In one aspect, the invention features a compound of Formula I or a pharmaceutically acceptable salt thereof, wherein:

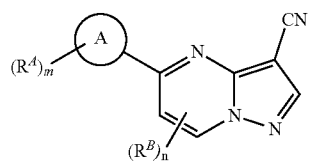

I

Ring A is selected from monocyclic or bicyclic aryl, monocyclic or bicyclic heteroaryl, cycloalkyl and heterocyclyl;

each $R^A$ is independently selected from monocyclic or bicyclic aryl, monocyclic or bicyclic heteroaryl, monocyclic or bicyclic cycloalkyl, monocyclic or bicyclic heterocyclyl, $C_1$-$C_6$ alkyl, $C_1$-$C_6$ alkoxyl, halo, $C_1$-$C_6$ haloalkyl, $C_1$-$C_6$ haloalkoxyl, $C_1$-$C_6$ hydroxyalkyl, $C_1$-$C_6$ heteroalkyl, —N($R^1$)($R^2$), nitro, cyano, —C(O)$R^2$, —OC(O)$R^2$, —C(O)O$R^1$, —S$R^1$, —S(O)$_2R^1$, —S(O)$_2$—N($R^2$)($R^2$), —($C_1$-$C_6$ alkylene)-S(O)$_2$—N($R^2$)($R^2$), —C(O)—N($R^2$)($R^2$), —N($R^2$)($R^2$)—C(O)$R^1$, —($C_1$-$C_6$ alkylene)-N($R^2$)—C(O)$R^1$, —N$R^2$S(O)$_2R^1$, —P(O)($R^1$)($R^1$), and —O$R^1$; wherein each of aryl, heteroaryl, cycloalkyl, heterocyclyl, alkyl, alkoxyl, haloalkyl, hydroxyalkyl, heteroalkyl is independently substituted with 0-5 occurrences of $R^a$;

each $R^B$ is independently selected from $C_1$-$C_6$ alkyl, $C_1$-$C_6$ alkoxyl, halo, $C_1$-$C_6$ haloalkyl, $C_1$-$C_6$ haloalkoxyl, $C_1$-$C_6$ hydroxyalkyl, $C_1$-$C_6$ heteroalkyl, —N($R^1$)($R^1$), nitro, cyano, and —O$R^1$;

each $R^1$ is independently selected from hydrogen, $C_1$-$C_6$ alkyl, $C_1$-$C_6$ haloalkyl, $C_1$-$C_6$ haloalkoxyl, $C_1$-$C_6$ hydroxyalkyl, $C_1$-$C_6$ heteroalkyl, cycloalkyl, cycloalkylalkyl, heterocyclyl, and heterocyclylalkyl, wherein each of $C_1$-$C_6$ alkyl, $C_1$-$C_6$ haloalkyl, $C_1$-$C_6$ hydroxyalkyl, $C_1$-$C_6$ heteroalkyl, cycloalkyl, cycloalkylalkyl, heterocyclyl, and heterocyclylalkyl is independently substituted with 0-5 occurrences of $R^b$;

each $R^2$ is independently selected from hydrogen, $C_1$-$C_6$ alkyl, $C_1$-$C_6$ heteroalkyl; or 2 $R^2$ together with the nitrogen to which they are attached form a heterocyclyl ring substituted with 0-5 occurrences of $R^b$;

each $R^a$ and $R^b$ is independently selected from halo, cyano, hydroxyl, $C_1$-$C_6$ alkyl, $C_1$-$C_6$ alkoxyl, $C_1$-$C_6$ haloalkoxyl, —N(R")(R"), —C(O)—N(R")(R"), —N(R") (R")—C(O)R', and —($C_1$-$C_6$ alkylene)-N(R")—C(O)R';

each R' and R" is independently selected from hydrogen and $C_1$-$C_6$ alkyl or $C_1$-$C_6$ hydroxyalkyl;

m is 0, 1, 2, 3, 4 or 5; and n is 0, 1 or 2;

provided that the compound is not (R)-5-(2-(2,5-difluorophenyl)pyrrolidin-1-yl)pyrazolo[1,5-a]pyrimidine-3-carbonitrile.

In another aspect, the present invention provides pharmaceutical compositions comprising a compound of structural formula (I) or a pharmaceutically acceptable salt thereof and a pharmaceutically acceptable carrier.

In another aspect, the present invention provides a method for inhibiting NTRK activity in a cell or in a patient. In some embodiments, said method comprises the step of contacting the cell or administering to the patient a compound of structural formula (I) or a pharmaceutically acceptable salt or composition thereof.

In another aspect, the present invention provides a method for treating a subject suffering from a condition mediated by aberrant NTRK activity. In some embodiments, said method comprises administering to the subject a therapeutically effective amount of a compound of structural formula (I) or a pharmaceutically acceptable salt or composition thereof.

In another aspect, the present invention provides a method for treating a subject who has developed resistance to a cancer treatment. In some embodiments, said method comprises administering to the subject a therapeutically effective amount of a compound of structural formula (I) or a pharmaceutically acceptable salt or composition thereof.

EMBODIMENTS OF THE INVENTION

In one aspect, the invention features a compound of Formula I or a pharmaceutically acceptable salt thereof, wherein:

(I)

Ring A is selected from monocyclic or bicyclic aryl, monocyclic or bicyclic heteroaryl, cycloalkyl and heterocyclyl;

each $R^A$ is independently selected from monocyclic or bicyclic aryl, monocyclic or bicyclic heteroaryl, monocyclic or bicyclic cycloalkyl, monocyclic or bicyclic heterocyclyl, $C_1$-$C_6$ alkyl, $C_1$-$C_6$ alkoxyl, halo, $C_1$-$C_6$ haloalkyl, $C_1$-$C_6$ haloalkoxyl, $C_1$-$C_6$ hydroxyalkyl, $C_1$-$C_6$ heteroalkyl, —N($R^1$)($R^1$), nitro, cyano, —C(O)$R^1$, —OC(O)$R^1$, —C(O)O$R^1$, —S$R^1$, —S(O)$_2R^1$, —S(O)$_2$—N($R^2$)($R^2$), —($C_1$-$C_6$ alkylene)-S(O)$_2$—N($R^2$)($R^2$), —C(O)—N($R^2$)($R^2$), —N($R^2$)($R^2$)—C(O)$R^1$, —($C_1$-$C_6$ alkylene)-N($R^2$)—C(O)$R^1$, —N$R^2$S(O)$_2R^1$, —P(O)($R^1$)($R^1$), and —O$R^1$; wherein each of aryl, heteroaryl, cycloalkyl, heterocyclyl, alkyl, alkoxyl, haloalkyl, hydroxyalkyl, heteroalkyl is independently substituted with 0-5 occurrences of $R^a$;

each $R^B$ is independently selected from $C_1$-$C_6$ alkyl, $C_1$-$C_6$ alkoxyl, halo, $C_1$-$C_6$ haloalkyl, $C_1$-$C_6$ haloalkoxyl, $C_1$-$C_6$ hydroxyalkyl, $C_1$-$C_6$ heteroalkyl, —N($R^1$)($R^1$), nitro, cyano, and —O$R^1$;

each $R^1$ is independently selected from hydrogen, $C_1$-$C_6$ alkyl, $C_1$-$C_6$ haloalkyl, $C_1$-$C_6$ haloalkoxyl, $C_1$-$C_6$ hydroxyalkyl, $C_1$-$C_6$ heteroalkyl, cycloalkyl, cycloalkylalkyl, heterocyclyl, and heterocyclylalkyl, wherein each of $C_1$-$C_6$ alkyl, $C_1$-$C_6$ haloalkyl, $C_1$-$C_6$ hydroxyalkyl, $C_1$-$C_6$ heteroalkyl, cycloalkyl, cycloalkylalkyl, heterocyclyl, and heterocyclylalkyl is independently substituted with 0-5 occurrences of $R^b$;

each $R^2$ is independently selected from hydrogen, $C_1$-$C_6$ alkyl, $C_1$-$C_6$ heteroalkyl; or 2 $R^2$ together with the nitrogen to which they are attached form a heterocyclyl ring substituted with 0-5 occurrences of $R^b$;

each $R^a$ and $R^b$ is independently selected from halo, cyano, hydroxyl, $C_1$-$C_6$ alkyl, $C_1$-$C_6$ alkoxyl, $C_1$-$C_6$ haloalkoxyl, —N(R")(R"), —C(O)—N(R")(R"), —N(R")(R")—C(O)R', and —($C_1$-$C_6$ alkylene)-N(R")—C(O)R';

each R' and R" is independently selected from hydrogen and $C_1$-$C_6$ alkyl or $C_1$-$C_6$ hydroxyalkyl;

m is 0, 1, 2, 3, 4 or 5; and n is 0, 1 or 2;

provided that the compound is not (R)-5-(2-(2,5-difluorophenyl)pyrrolidin-1-yl)pyrazolo[1,5-a]pyrimidine-3-carbonitrile.

In some embodiments, the compound has Formula (Ia-1):

(Ia-1)

In some embodiments, at least one $R^A$ is halo.

In other embodiments, the compound has Formula (Ib):

(Ib)

In some embodiments, one $R^A$ is halo and one $R^A$ is aryl or heteroaryl.

In some embodiments, the compound has Formula Ic:

(Ic)

Formula Ic-1:

(Ic-1)

wherein:

X is N or C($R^9$);

$R^{A1}$ is fluoro or —CN;

$R^{A2}$ is fluoro or hydrogen;

$R^{B1}$ is hydrogen or fluoro;

$R^9$ is selected from hydrogen, halo, —CN, $C_1$-$C_4$ alkyl, —C(O)N($R^{11}$)($R^{11}$), and —S(O)$_2$N($R^1$)($R^1$), wherein any alkyl portion of $R^9$ is optionally substituted with one or more substituents selected from —OH and —F;

$R^{10}$ is selected from hydrogen, halo, —O—($C_1$-$C_4$ alkyl) optionally substituted with one or more halo, and —C(O)N($R^{11}$)($R^{11}$); and each $R^{11}$ is independently selected from hydrogen, and $C_1$-$C_4$ alkyl optionally substituted with one or more substituents selected from —OH and cyclopropyl.

In some embodiments of Formula Ic, $R^9$ is selected from hydrogen, fluoro, chloro, —CN, —C(O)NH$_2$, —C(O)NHCH$_3$, —C(O)N(CH$_3$)$_2$, —C(O)NHCH$_2$CH$_2$OH, —C(OH)(CH$_3$)$_2$, —S(O)$_2$NH$_2$, and N-(cyclopropylmethyl)carbamyl.

In some embodiments of Formula Ic, $R^{10}$ is selected from hydrogen, fluoro, chloro, —OCH$_3$, —OCF$_3$ and —C(O)NH$_2$.

In another aspect, the invention features a method for inhibiting NTRK activity in a cell or in a patient comprising the step of contacting the cell or administering to the patient a compound described herein (e.g., a compound in Table 1) or a pharmaceutically acceptable salt thereof, or a pharmaceutical composition thereof.

In another aspect, the invention features a method for treating a subject suffering from a condition mediated by aberrant NTRK activity, comprising administering to the subject a therapeutically effective amount of a compound described herein (e.g., a compound in Table 1) or a pharmaceutically acceptable salt thereof, or a pharmaceutical composition thereof.

In another aspect, the present invention features a method for treating a subject who has developed resistance to a cancer treatment, comprising administering to the subject a therapeutically effective amount of a compound described herein (e.g., a compound in Table 1) or a pharmaceutically acceptable salt thereof, or a pharmaceutical composition thereof.

Definitions

As used herein, the terms a "patient," "subject," "individual," and "host" refer to either a human or a non-human animal suffering from or suspected of suffering from a disease or disorder associated with aberrant NTRK expression (i.e., increased NTRK activity caused by signaling through NTRK) or biological activity.

"Treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "preventing" when used in relation to a condition or disease such as cancer, refers to a reduction in the frequency of, or delay in the onset of, symptoms of the condition or disease. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The term "therapeutic effect" refers to a beneficial local or systemic effect in animals, particularly mammals, and more particularly humans, caused by administration of a compound or composition of the invention. The phrase "therapeutically-effective amount" means that amount of a compound or composition of the invention that is effective to treat a disease or condition caused by over expression of NTRK or aberrant NTRK biological activity at a reasonable benefit/risk ratio.

The therapeutically effective amount of such substance will vary depending upon the subject and disease condition being treated, the weight and age of the subject, the severity of the disease condition, the manner of administration and the like, which can readily be determined by one of skill in the art.

As used herein, "developing resistance" means that when a drug is first administered to the patient, the patient's symptoms improve, whether measured by decrease in tumor volume, a decrease in the number of new lesions, or some other means that a physician uses to judge disease progression; however, those symptoms stop improving, or even worsen at some point. At that time, the patient is said to have developed resistance to the drug.

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —CH$_2$—, —CH$_2$CH$_2$—, and CH$_2$CH$_2$CH$_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like. The term "haloalkoxy" refers to an alkoxy in which one or more hydrogen atoms are replaced by halo, and includes alkoxy moieties in which all hydrogens have been replaced by halo (e.g., perfluoroalkoxy).

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkenylene" refers to an alkenyl group having two connecting points. For example, "ethenylene" represents the group —CH=CH—. Alkenylene groups can also be in an unsubstituted form or substituted form with one or more substituents.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to an alkynyl having two connecting points. For example, "ethynylene" represents the group —C≡C—. Alkynylene groups can also be in an unsubstituted form or substituted form with one or more substituents.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Haloalkyl" and "haloalkoxyl" refers to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Haloalkylene" refers to a divalent alkyl, e.g., —CH$_2$—, —CH$_2$CH$_2$—, and —CH$_2$CH$_2$CH$_2$—, in which one or more hydrogen atoms are replaced by halo, and includes alkyl moieties in which all hydrogens have been replaced by halo.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —CH$_2$OCH$_2$CH$_3$ radical is referred to as a "$C_3$" heteroalkyl. Connection to the rest of the molecule may be through either a heteroatom or a carbon in the heteroalkyl chain. "Heteroalkylene" refers to a divalent optionally substituted alkyl, which has one or more skeletal chain atoms selected from an atom other than carbon, e.g., oxygen, nitrogen, sulfur, phosphorus or combinations thereof.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a -(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In some embodiments, heteroaryl can include

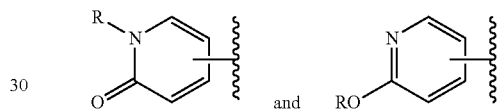

wherein R is H or $C_{1-6}$ alkyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

"Heterocyclylalkyl" refers to an alkyl group substituted with a heterocyclyl group.

"Cyano" refers to a —CN radical.

"Nitro" refers to —NO$_2$.

"Hydroxy" or "hydroxyl" refers to —OH.

"Hydroxyalkyl" refers to a divalent alkyl, e.g., —CH$_2$—, —CH$_2$CH$_2$—, and —CH$_2$CH$_2$CH$_2$—, in which one or more hydrogen atoms are replaced by a hydroxy, and includes alkyl moieties in which all hydrogens have been replaced by hydroxy.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee = (90-10)/100 = 80\%.$$

Thus, a composition containing 90% of one enantiomer and 10% of the other is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

TABLE 1 below shows the structures of compounds described herein.

| Compound Number | Structure |
| --- | --- |
| 1 | (structure) |
| 2 | (structure) |
| 3 | (structure) |

TABLE 1-continued below shows the structures of compounds described herein.

| Compound Number | Structure |
|---|---|
| 4 | |
| 5 | |
| 6 | |
| 7 | |
| 8 | 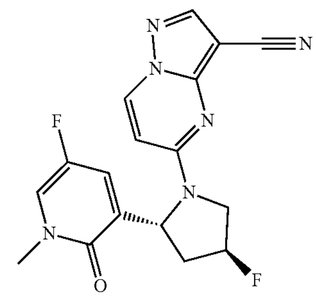 [SMILES: Cn1cc(F)cc([C@H]2C[C@H](F)CN2c2ccn3ncc(C#N)c3n2)c1=O] |
| 9 | 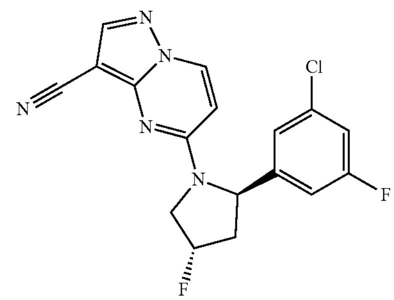 [SMILES: N#Cc1cnn2ccc(N3C[C@@H](F)C[C@@H]3c3cc(F)cc(Cl)c3)nc12] |
| 10 | 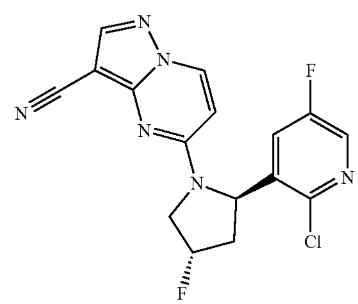 [SMILES: N#Cc1cnn2ccc(N3C[C@@H](F)C[C@@H]3c3cc(F)cnc3Cl)nc12] |
| 11 | 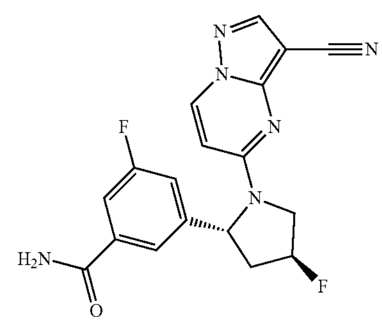 [SMILES: N#Cc1cnn2ccc(N3C[C@@H](F)C[C@@H]3c3cc(F)cc(C(N)=O)c3)nc12] |
| 12 | 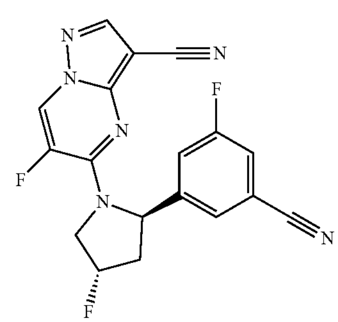 [SMILES: N#Cc1cc(F)cc([C@H]2C[C@H](F)CN2c2nc3c(C#N)cnn3cc2F)c1] |

TABLE 1-continued
below shows the structures of compounds described herein.
| Compound Number | Structure |
|---|---|
| 13 | 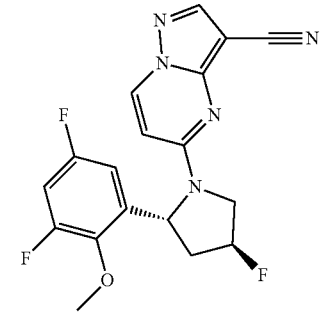 [SMILES: COc1c(F)cc(F)cc1[C@H]1C[C@H](F)CN1c1ccn2ncc(C#N)c2n1] |
| 14 | |
| 15 | |
| 16 | |
| 17 | 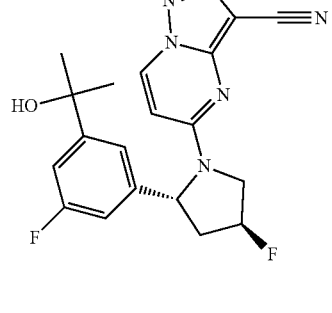 |
| 18 | 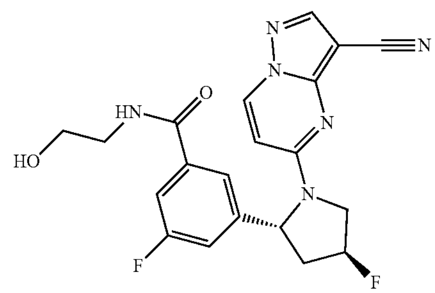 [SMILES: N#Cc1cnn2ccc(N3C[C@@H](F)C[C@@H]3c3cc(F)cc(C(=O)NCCO)c3)nc12] |
| 19 | 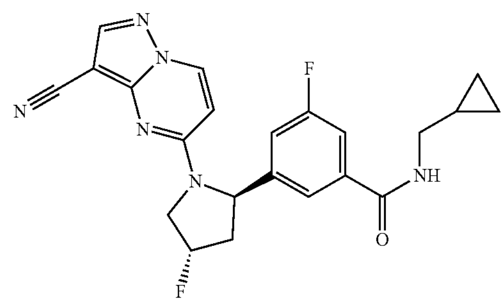 [SMILES: N#Cc1cnn2ccc(N3C[C@@H](F)C[C@@H]3c3cc(F)cc(C(=O)NCC4CC4)c3)nc12] |
| 20 | 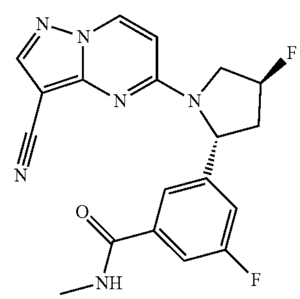 [SMILES: CNC(=O)c1cc(F)cc([C@H]2C[C@H](F)CN2c2ccn3ncc(C#N)c3n2)c1] |
| 21 | 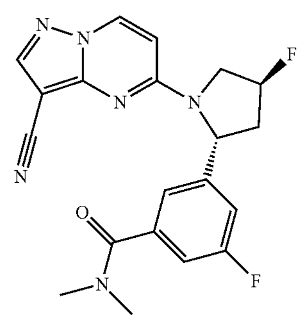 [SMILES: CN(C)C(=O)c1cc(F)cc([C@H]2C[C@H](F)CN2c2ccn3ncc(C#N)c3n2)c1] |

TABLE 1-continued below shows the structures of compounds described herein.

| Compound Number | Structure |
|---|---|
| 22 | (structure shown) |

Pharmaceutically acceptable salts of these compounds are also contemplated for the uses described herein.

"Pharmaceutically acceptable salt" refers to any salt of a compound of the invention which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Pharmaceutical Compositions

Pharmaceutical compositions of the invention comprise one or more compounds of the invention and one or more physiologically or pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the invention are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present invention that may be combined with the carrier materials to produce a composition in a single dosage form will vary depending upon the host treated, the particular mode of administration.

Dosages

Toxicity and therapeutic efficacy of compounds of the invention, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Treatment

NTRK fusions have been implicated in several types of cancers. These fusions harbor an intact NTRK kinase domain that is identical to the native or wild-type form of the receptor; therefore, as used herein, any NTRK protein (NTRK1, 2 or 3) with the same kinase domain as wild-type NTRK will be referred to as "wild-type NTRK." Mutations can occur in the NTRK kinase domain, leading to mutants that are resistant to kinase inhibitor therapy. These resistance mutations can be predicted using structural biology and computational analyses, as well as by examining codon sequences in which a sequence change gives rise to a codon for a different amino acid. Alternatively, resistance mutations for a given inhibitor can be identified experimentally by administration of that inhibitor (e.g., a known NTRK wild-type inhibitor) and exposing cells to a mutation-promoting agent, such as ENU (N-ethyl-N-nitrosourea). The cells are washed and then plated with increasing concentrations (2-100× proliferation $IC_{50}$) of the compound of choice. The wells with cellular outgrowth are then collected after 3-4 weeks. In particular, a mutation at amino acid position 595 within the NTRK fusion (NTRK1 wt numbering), effecting a change from a glycine to an arginine residue (heretofore designated 'G595R') was identified via both methods. This mutation was subsequently demonstrated to confer significant resistance to two NTRK inhibitors that are being clinically evaluated (shown in the table below). As shown in the table, the compounds are active against the wild-type NTRK, but are markedly less active against the G595R mutant form of the NTRK fusion.

| Compound | NTRK wt Enzyme Assay $IC_{50}$ (nM) | NTRK wt Cellular $GI_{50}$ (nM) | NTRK G595R Cellular $GI_{50}$ (nM) |
|---|---|---|---|
| Entrectinib | 0.6 | 2 | 2700 |
| TSR-011 | 2.3 | 32 | 12000 |
| Crizotinib | 9.3 | 87 | 9000 |

The invention provides compounds that inhibit both wild-type NTRK and mutants thereof, including the G595R mutant. Furthermore, the inhibitors can be selective for wild-type NTRK, over other kinases, thus leading to reduced toxicities associated with inhibiting other kinases. Because of their activity against wild-type and mutant NTRK, the compounds described herein can be used to treat a patient with a condition associated with aberrant NTRK activity. They can also be used to treat various cancers. In some embodiments, the cancer is selected from non-small cell lung cancer, breast cancer, melanoma, low and high grade glioma, glioblastoma, pediatric astrocytoma, colorectal cancer, thyroid cancer, pancreatic cancer, biliary cancer, head and neck cancer, primary CNS tumors, cholangiocarcinoma, acute myelogenous leukemia, breast cancer, salivary gland cancer, sarcoma, and spitzoid neoplasms.

The compounds can also be used to treat a patient who has developed resistance to a wild-type NTRK inhibitor, or a patient with a mutant form of NTRK, such as the G595R mutant. The method includes the step of administering a compound or composition of the invention that is active against the NTRK resistant mutant. By "active" is meant that a compound has an $IC_{50}$ of less than 1 µM, 500 nM, 250 nM, 100 nM, 75 nM, 50 nM, 25 nM, 10 nM, or 5 nM when measured in a biochemical assay, against at least one resistant mutant.

The compounds and compositions described herein can be administered alone or in combination with other compounds, including other NTRK-modulating compounds, or other therapeutic agents. In some embodiments, the compound or composition of the invention may be administered in combination with one or more compounds selected from cabozantinib (COMETRIQ®), vandetanib (CALPRESA®), sorafenib (NEXAVAR®), sunitinib (SUTENT®), regorafenib (STAVARGA®), ponatinib (ICLUSIG®), bevacizumab (AVASTIN®), crizotinib (XALKORI®), or gefitinib (IRESSA®). The compound or composition of the invention may be administered simultaneously or sequentially with the other therapeutic agent by the same or different routes of administration. The compound of the invention may be included in a single formulation with the other therapeutic agent or in separate formulations.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS:

Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS:

Preparative HPLC was performed on a Shimadzu Discovery VP® Preparative system fitted with a Luna 5 u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Chiral HPLC:

Preparative HPLC to resolve chiral mixtures was performed on a Thar SFC Pre-80 instrument fitted with a Chiralpak AS-H column (5 mm, 3.0 cm id×25 cm L). The mobile phases consisted of SFC $CO_2$ (A) and MeOH/0.1% $NH_4OH$ (B). A constant gradient from 67% to 33% (B) was maintained at a flow rate of 65 g/min, with a system back pressure of 100 bar. The separation progress was monitored by UV detection at a wavelength of 220 nm.

Silica Gel Chromatography:

Silica gel chromatography was performed on either a Teledyne Isco CombiFlash® Rf unit or a Biotage® Isolera Four unit.

Proton NMR:

Unless otherwise indicated, all 1H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-$d_6$ solvent as parts-per million (ppm) with respect to residual DMSO (2.50 ppm).

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Protocol 1

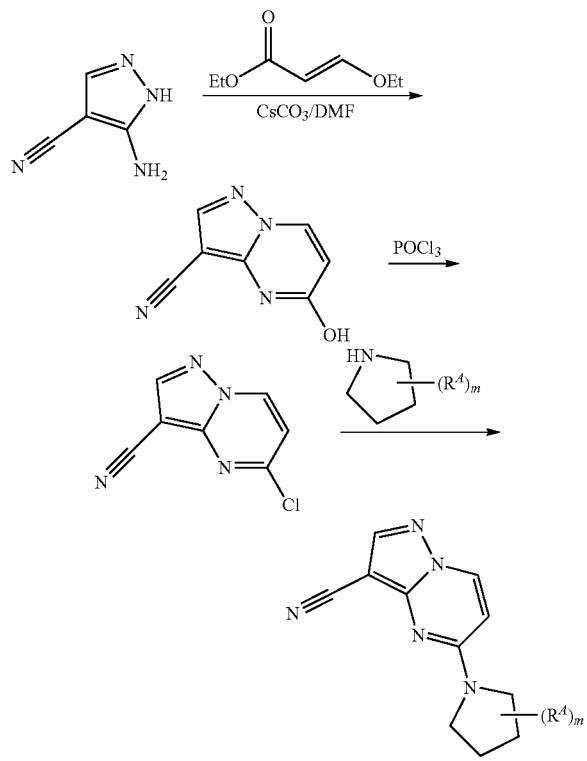

General synthetic protocol 1 involves formation of 5-hydroxypyrazolo[1,5-a]pyrimidine-3-carbonitrile via the cyclization of 5-amino-1H-pyrazole-4-carbonitrile and ethyl (E)-3-ethoxyacrylate or suitable equivalent, under thermal conditions in the presence of a base such as cesium carbonate. The hydroxyl group is converted to a leaving group such as chloride by reaction with phosphorous oxychloride. The chloro group is displaced by an amine in a solvent such as dioxane or n-butanol in the presence of a base such as DIPEA, or via Pd-catalyzed cross-coupling under, e.g., Buchwald conditions, to give the desired products.

Synthetic Protocol 2

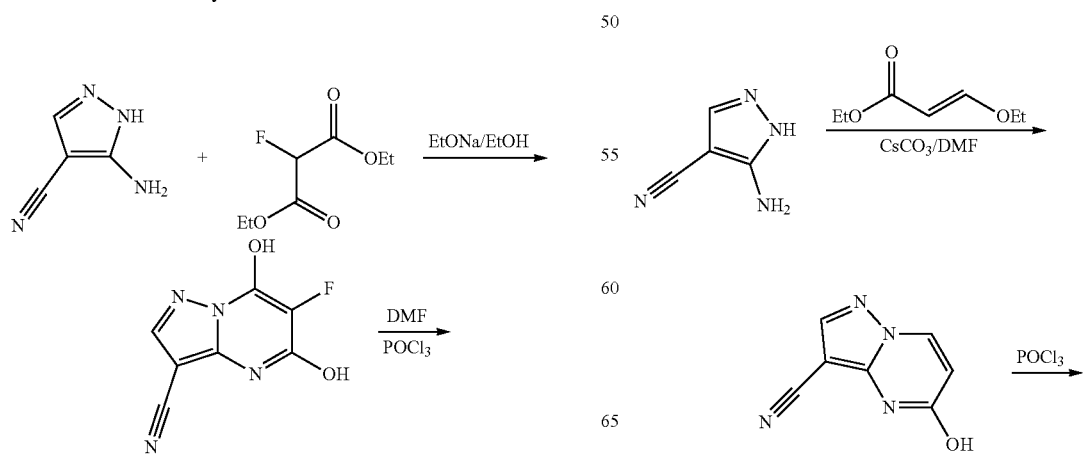

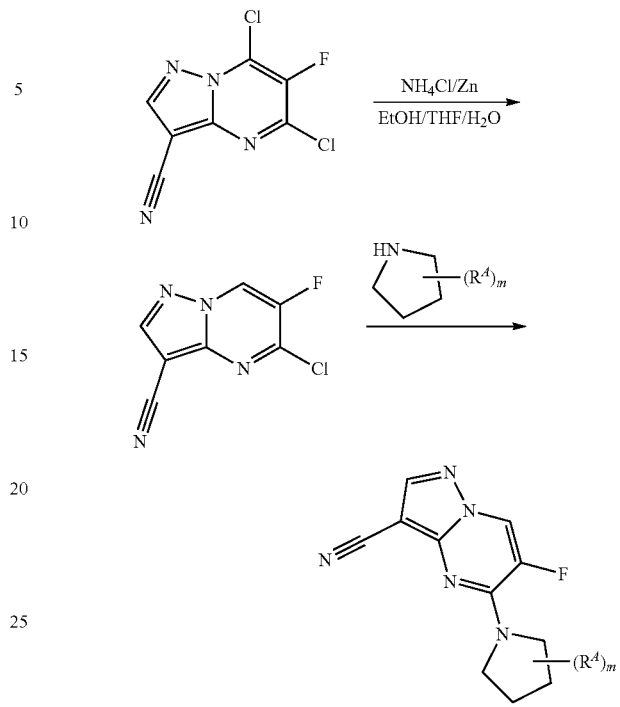

General synthetic protocol 2 involves formation of 6-fluoro-5,7-dihydroxypyrazolo[1,5-a]pyrimidine-3-carbonitrile via the cyclization of 5-amino-1H-pyrazole-4-carbonitrile and diethyl 2-fluoromalonate, or a suitable equivalent. The hydroxyl groups are converted to chlorides by reaction with phosphorous oxychloride. The 7-chloro group can be selectively reduced in the presence of the 5-chloro group in the presence of a reducing agent such as zinc. The remaining chloro group is displaced by an amine in a solvent such as dioxane or n-butanol in the presence of a base such as DIPEA, or via Pd-catalyzed cross-coupling under, e.g., Buchwald conditions, to give the desired products.

Example 1: 5-((2R,4S)-4-fluoro-2-(5-fluoropyridin-3-yl)pyrrolidin-1-yl)pyrazolo[1,5-a]pyrimidine-3-carbonitrile (Compound 1)

-continued

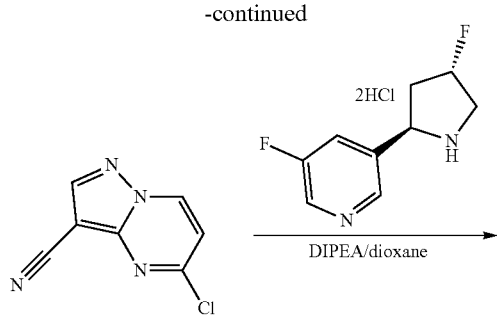

Step 1: Synthesis of 5-hydroxypyrazolo[1,5-a]pyrimidine-3-carbonitrile

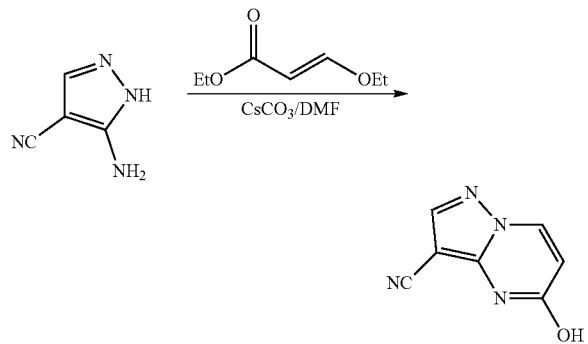

To a mixture of 5-amino-1H-pyrazole-4-carbonitrile (10.00 g, 92.51 mmol) in DMF (350.00 mL) was added ethyl (E)-3-ethoxyacrylate (13.34 g, 92.51 mmol) and $Cs_2CO_3$ (60.38 g, 185.02 mmol). The mixture was stirred at 100° C. for 2 hrs. After LCMS showed the reaction was complete, the reaction mixture was cooled to 25° C., then added to water (300 mL), acidified by HCl (1 M) till pH=4, then filtered. The filter cake was dried in vacuum to give 5-hydroxypyrazolo[1,5-a]pyrimidine-3-carbonitrile (10.00 g, yield: 67.51%) as a white solid.

Step 2: Synthesis of 5-chloropyrazolo[1,5-a]pyrimidine-3-carbonitrile

A mixture of 5-hydroxypyrazolo[1,5-a]pyrimidine-3-carbonitrile (10.00 g, 62.45 mmol) in $POCl_3$ (200.00 mL) was heated to 150° C. for 4 hrs. After TLC (PE:EtOAc=1:1) showed the reaction was complete, the mixture was concentrated to remove $POCl_3$, then dissolved in DCM (100 mL), concentrated and purified by column chromatography on silica gel (DCM) to give 5-chloropyrazolo[1,5-a]pyrimidine-3-carbonitrile (6.00 g, yield: 53.80%) as a white solid.

Step 3: Synthesis of 5-((2R,4S)-4-fluoro-2-(5-fluoropyridin-3-yl)pyrrolidin-1-yl)pyrazolo[1,5-a]pyrimidine-3-carbonitrile

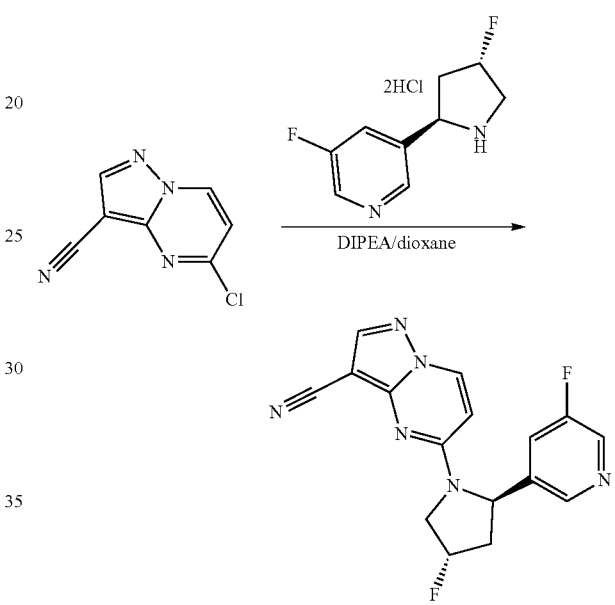

To a mixture of 5-chloropyrazolo[1,5-a]pyrimidine-3-carbonitrile (86.00 mg, 334.49 umol, 1.20 eq) and 3-fluoro-5-((2R,4S)-4-fluoropyrrolidin-2-yl)pyridine HCl (49.78 mg, 278.74 umol, 1.00 eq) in dioxane (6.00 mL) was added DIPEA (108.07 mg, 836.23 umol, 3.00 eq) in one portion. The mixture was stirred at 130° C. for 16 hrs. LCMS showed the reaction was complete. The reaction mixture was purified by acidic prep-HPLC to afford 5-((2R,4S)-4-fluoro-2-(5-fluoropyridin-3-yl)pyrrolidin-1-yl)pyrazolo[1,5-a]pyrimidine-3-carbonitrile (90.60 mg, 163.43 umol, yield: 58.63%) as a yellow oil.

Example 2: (R)-5-(4,4-difluoro-2-(5-fluoropyridin-3-yl)pyrrolidin-1-yl)pyrazolo[1,5-a]pyrimidine-3-carbonitrile (Compound 3)

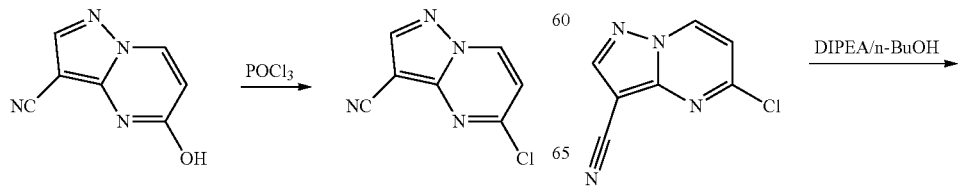

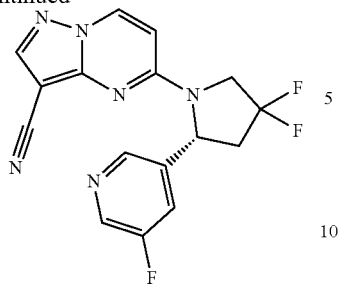

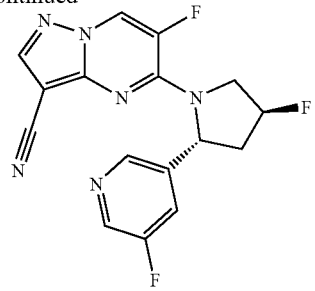

To a mixture of 5-chloropyrazolo[1,5-a]pyrimidine-3-carbonitrile (40.00 mg, 223.99 umol, 1.00 eq) and 3-[(2R)-4,4-difluoropyrrolidin-2-yl]-5-fluoro-pyridine (61.62 mg, 223.99 umol, 1.00 eq) in n-BuOH (2.00 mL) was added DIPEA (144.74 mg, 1.12 mmol, 5.00 eq). The resulting mixture was stirred at 100° C. for 16 hrs. The mixture was concentrated and the crude product was purified by acidic prep-HPLC (TFA system). (R)-5-(4,4-difluoro-2-(5-fluoropyridin-3-yl)pyrrolidin-1-yl)pyrazolo[1,5-a]pyrimidine-3-carbonitrile (48.70 mg, 85.09 umol, yield: 38%) was obtained as a brown solid.

Example 3: 6-fluoro-5-((2R,4S)-4-fluoro-2-(5-fluoropyridin-3-yl)pyrrolidin-1-yl)pyrazolo[1,5-a]pyrimidine-3-carbonitrile (Compound 4)

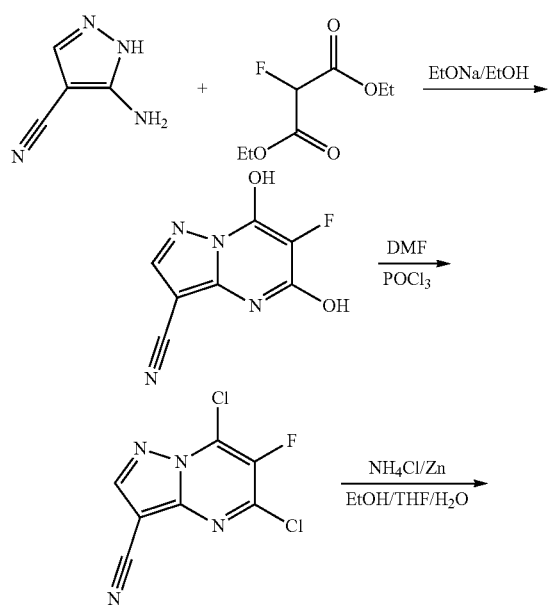

Step 1: 6-fluoro-5,7-dihydroxypyrazolo[1,5-a]pyrimidine-3-carbonitrile

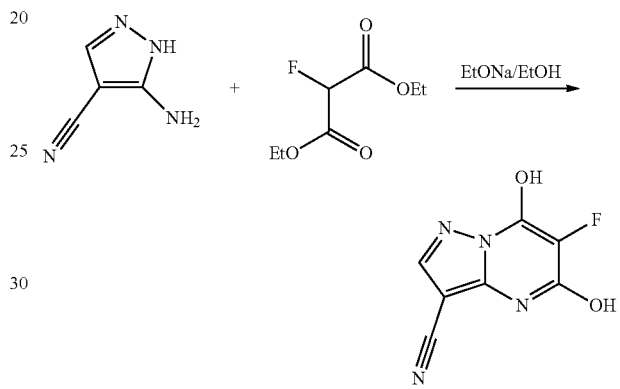

To the mixture of freshly prepared NaOEt (4.34 g, 63.83 mmol, 1.38 eq) in anhydrous EtOH (100.00 mL) was added 5-amino-1H-pyrazole-4-carbonitrile (5.00 g, 46.25 mmol, 1.00 eq) and diethyl 2-fluoromalonate (8.65 g, 48.56 mmol, 1.05 eq) at 20° C. The resulting mixture was heated to 120° C. for 32 hrs. The mixture was concentrated to remove EtOH, and the resulting residue was dissolved in water (50 mL). The water layer was acidified by HCl (1 M) to pH=2-3 and a white precipitate was generated. The solid was collected by filtration and dried in vacuo to give the crude 6-fluoro-5,7-dihydroxypyrazolo[1,5-a]pyrimidine-3-carbonitrile (4.00 g, yield: 44.54%) as a white solid. $^1$H-NMR (400 MHz, DMSO-d$_6$) δ ppm 7.92 (s, 1H).

Step 2: 5,7-dichloro-6-fluoropyrazolo[1,5-a]pyrimidine-3-carbonitrile

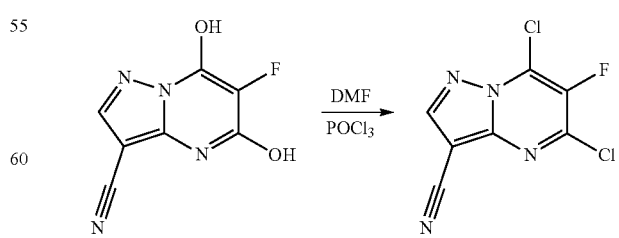

To a mixture of 6-fluoro-5,7-dihydroxypyrazolo[1,5-a]pyrimidine-3-carbonitrile (4.00 g, 20.61 mmol, 1.00 eq) in POCl$_3$ (80.00 mL) was added DMF (150.61 mg, 2.06 mmol, 158.53 uL, 0.10 eq), and the mixture was heated to 100° C. for 16 hrs. The mixture was concentrated to give the crude product. The crude product was purified by flash column chromatography on silica gel (DCM) to give 5,7-dichloro-6-fluoropyrazolo[1,5-a]pyrimidine-3-carbonitrile (1.30 g, yield: 27.32%) as a yellow solid. $^1$H-NMR (400 MHz, CDCl$_3$) δ ppm 8.48 (s, 1H).

Step 3: 5-chloro-6-fluoropyrazolo[1,5-a]pyrimidine-3-carbonitrile

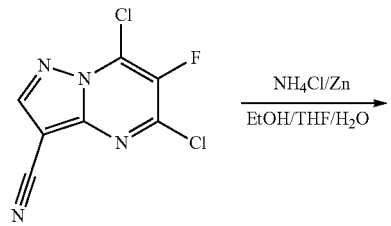

To a mixture of 5,7-dichloro-6-fluoropyrazolo[1,5-a]pyrimidine-3-carbonitrile (1.30 g, 5.63 mmol, 1.00 eq) in EtOH/THF/H$_2$O (50.00 mL, V/V/V=3/1/2) was added Zn powder (1.84 g, 28.14 mmol, 5.00 eq) and NH$_4$Cl (1.20 g, 22.51 mmol, 786.96 uL, 4.00 eq). The mixture was stirred at 20° C. for 0.1 hr. The mixture was concentrated to remove EtOH and THF. The mixture was extracted with EtOAc (10 mL*2), the organic layers were dried over Na$_2$SO$_4$, and concentrated to give 5-chloro-6-fluoropyrazolo[1,5-a]pyrimidine-3-carbonitrile (1.00 g, crude) as a yellow solid. $^1$H-NMR (400 MHz, CDCl$_3$) δ ppm 8.75 (d, 1H, J=2.4 Hz), 8.40 (s, 1H).

Step 4: 6-fluoro-5-((2R,4S)-4-fluoro-2-(5-fluoro-pyridin-3-yl)pyrrolidin-1-yl)pyrazolo[1,5-a]pyrimidine-3-carbonitrile

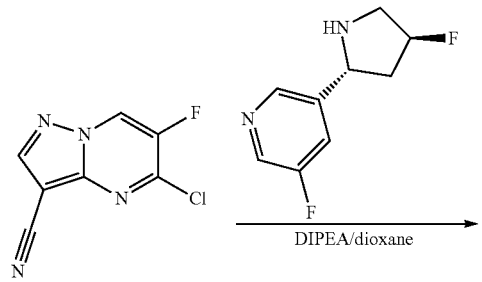

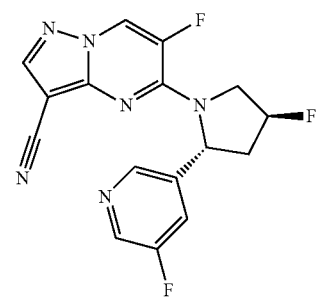

To a mixture of 5-chloro-6-fluoropyrazolo[1,5-a]pyrimidine-3-carbonitrile (200.50 mg, 1.02 mmol, 1.00 eq) in dioxane (5.00 mL) was added DIPEA (395.47 mg, 3.06 mmol, 3.00 eq) and 3-fluoro-5-((2R,4S)-4-fluoropyrrolidin-2-yl)pyridine (187.87 mg, 1.02 mmol, 1.00 eq). The mixture was stirred at 100° C. for 2 hrs. The mixture was concentrated to give the crude product. The crude product was purified by prep-HPLC (TFA system) to give 6-fluoro-5-((2R,4S)-4-fluoro-2-(5-fluoropyridin-3-yl)pyrrolidin-1-yl)pyrazolo[1,5-a]pyrimidine-3-carbonitrile (163.30 mg, yield: 46.50%) as a yellow oil.

Example 4: 5-((2R,4S)-4-cyano-2-(2,5-difluorophenyl)pyrrolidin-1-yl)pyrazolo[1,5-a]pyrimidine-3-carbonitrile (Compound 5)

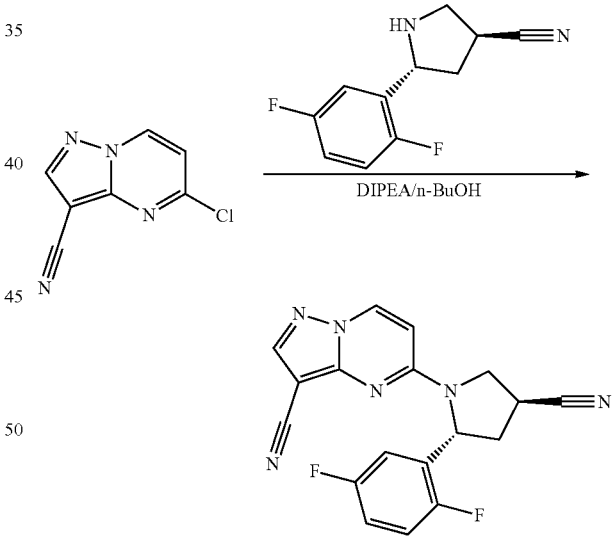

To a mixture of 5-chloropyrazolo[1,5-a]pyrimidine-3-carbonitrile (50.00 mg, 279.99 umol) in n-BuOH (3.00 mL) was added DIPEA (72.37 mg, 559.98 umol) and (3S,5R)-5-(2,5-difluorophenyl)pyrrolidine-3-carbonitrile (58.30 mg, 279.99 umol). The mixture was stirred at 100° C. for 16 hrs. LCMS showed the reaction was complete. The reaction mixture was concentrated to give the crude product. The crude product was purified by neutral prep-HPLC to give 5-((2R,4S)-4-cyano-2-(2,5-difluorophenyl)pyrrolidin-1-yl)pyrazolo[1,5-a]pyrimidine-3-carbonitrile (10.60 mg, 30.26 umol, yield: 10.81%) as a white solid.

Example 5: 5-((2R,4S)-2-(3-cyano-5-fluorophenyl)-4-fluoropyrrolidin-1-yl)pyrazolo[1,5-a]pyrimidine-3-carbonitrile (Compound 6)

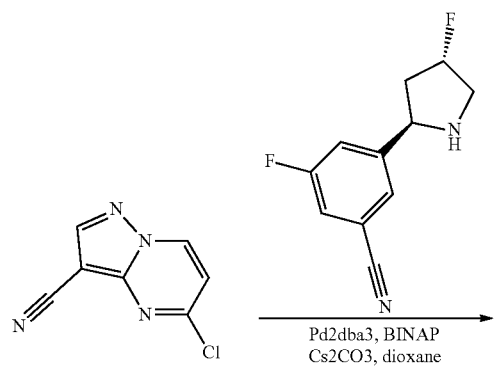

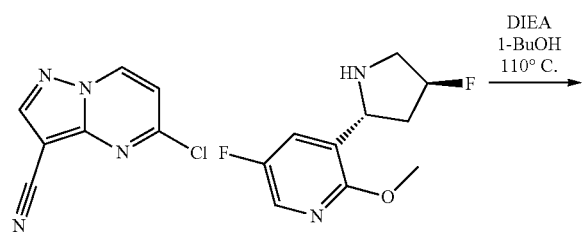

5-Chloropyrazolo[1,5-a]pyrimidine-3-carbonitrile (0.075 g, 0.420 mmol), 3-fluoro-5-((2R,4S)-4-fluoropyrrolidin-2-yl)benzonitrile (0.096 g, 0.462 mmol) and Cs₂CO₃ (0.411 g, 1.260 mmol) were taken up in dioxane (2 ml). Pd₂(dba)₃ (0.038 g, 0.042 mmol) and BINAP (0.052 g, 0.084 mmol) were added and stirred at 110° C. for 4 hours. The solvent was removed in vacuo. The residue was purified via reverse phase chromatography (0-100% ACN/H₂O) to give 5-((2R,4S)-2-(3-cyano-5-fluorophenyl)-4-fluoropyrrolidin-1-yl)pyrazolo[1,5-a]pyrimidine-3-carbonitrile (0.015 g, 0.043 mmol, 10.20% yield) as a white foam.

Example 6: 5-((2R,4S)-4-fluoro-2-(5-fluoro-2-methoxypyridin-3-yl)pyrrolidin-1-yl)pyrazolo[1,5-a]pyrimidine-3-carbonitrile (Compound 7)

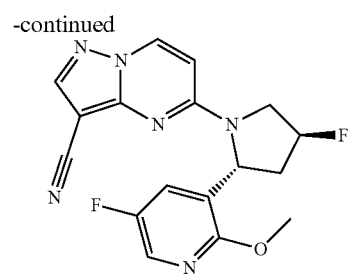

A mixture of 5-chloropyrazolo[1,5-a]pyrimidine-3-carbonitrile (88.5 mg, 0.50 mmol), 5-fluoro-3-((2R,4S)-4-fluoropyrrolidin-2-yl)-2-methoxypyridine hydrochloride (124 mg, 0.50 mmol) and DIEA (0.26 mL, 1.50 mmol) in n-butanol (2.5 mL) was heated in a microwave reactor at 110° C. for 60 minutes. The mixture was concentrated to remove solvents and the residue was purified by column chromatography on silica gel to give 5-((2R,4S)-4-fluoro-2-(5-fluoro-2-methoxypyridin-3-yl)pyrrolidin-1-yl)pyrazolo[1,5-a]pyrimidine-3-carbonitrile as a white solid (168 mg, yield: 95%).

Example 7: 5-((2R,4S)-4-fluoro-2-(5-fluoro-1-methyl-2-oxo-1,2-dihydropyridin-3-yl)pyrrolidin-1-yl)pyrazolo[1,5-a]pyrimidine-3-carbonitrile (Compound 8)

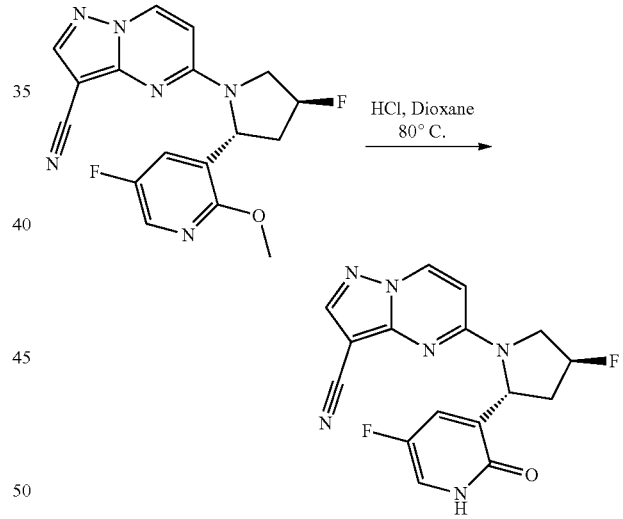

Step 1: 5-((2R,4S)-4-fluoro-2-(5-fluoro-2-oxo-1,2-dihydropyridin-3-yl)pyrrolidin-1-yl)pyrazolo[1,5-a]pyrimidine-3-carbonitrile A mixture of 5-((2R,4S)-4-fluoro-2-(5-fluoro-2-methoxypyridin-3-yl)pyrrolidin-1-yl)pyrazolo[1,5-a]pyrimidine-3-carbonitrile (110 mg, 0.31 mmol) and HCl in dioxane (4M, 0.4 mL, 1.50 mmol) in dioxane (1.2 mL) was heated at 85° C. for 8 hours. The mixture was quenched with saturated NaHCO₃ solution and extracted with EtOAc. The combined organic layers were dried over Na₂SO₄ and concentrated to give the crude product which was carried over to the next step without further purification. To a solution of 5-((2R,4S)-4-fluoro-2-(5-fluoro-2-oxo-1,2-dihydropyridin-3-yl)

pyrrolidin-1-yl)pyrazolo[1,5-a]pyrimidine-3-carbonitrile (100 mg, 0.29 mmol) in DMF (1.5 mL) at 0° C. was added NaH (60% dispersion, 14 mg, 0.35 mmol) and the solution was warmed at room temperature for 15 minutes. The reaction mixture was cooled again to 0° C., added MeI (0.022 mL, 0.35 mmol) and warmed to room temperature overnight. LCMS showed that the starting material was consumed. The mixture was diluted with water and extracted with EtOAc (2x). The combined organic layers were washed with water (3x), dried over Na₂SO₄ and concentrated to give the crude product which was purified by column chromatography on silica gel to give 5-((2R,4S)-4-fluoro-2-(5-fluoro-1-methyl-2-oxo-1,2-dihydropyridin-3-yl)pyrrolidin-1-yl)pyrazolo[1,5-a]pyrimidine-3-carbonitrile as a white solid (86 mg, yield: 83%).

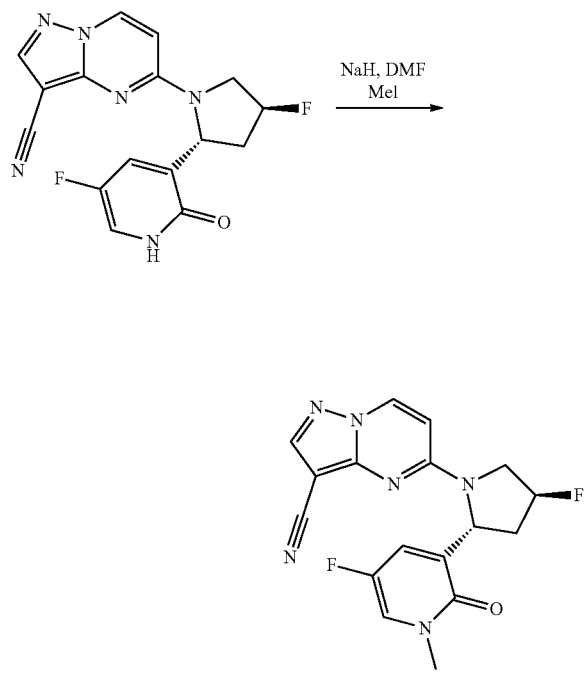

Step 2: Synthesis of 5-((2R,4S)-4-fluoro-2-(5-fluoro-1-methyl-2-oxo-1,2-dihydropyridin-3-yl)pyrrolidin-1-yl)pyrazolo[1,5-a]pyrimidine-3-carbonitrile To a solution of 5-((2R,4S)-4-fluoro-2-(5-fluoro-2-oxo-1,2-dihydropyridin-3-yl)pyrrolidin-1-yl)pyrazolo[1,5-a]pyrimidine-3-carbonitrile (100 mg, 0.29 mmol) in DMF (1.5 mL) at 0° C. was added NaH (60% dispersion, 14 mg, 0.35 mmol) and the solution was warmed at room temperature for 15 minutes. The reaction mixture was cooled again to 0° C., added MeI (0.022 mL, 0.35 mmol) and warmed to room temperature overnight. LCMS showed that the starting material was consumed. The mixture was diluted with water and extracted with EtOAc (2x). The combined organic layers were washed with water (3x), dried over Na₂SO₄ and concentrated to give the crude product which was purified by column chromatography on silica gel to give 5-((2R,4S)-4-fluoro-2-(5-fluoro-1-methyl-2-oxo-1,2-dihydropyridin-3-yl)pyrrolidin-1-yl)pyrazolo[1,5-a]pyrimidine-3-carbonitrile as a white solid (86 mg, yield: 83%).

Example 8: 5-((2R,4S)-4-fluoro-2-(3-fluoro-5-(2-hydroxypropan-2-yl)phenyl) pyrrolidin-1-yl)pyrazolo[1,5-a]pyrimidine-3-carbonitrile (Compound 14)

Step 1: 1-(3-((2R,4S)-1-(tert-butylsulfonyl)-4-fluoropyrrolidin-2-yl)-5-fluorophenyl) ethan-1-one

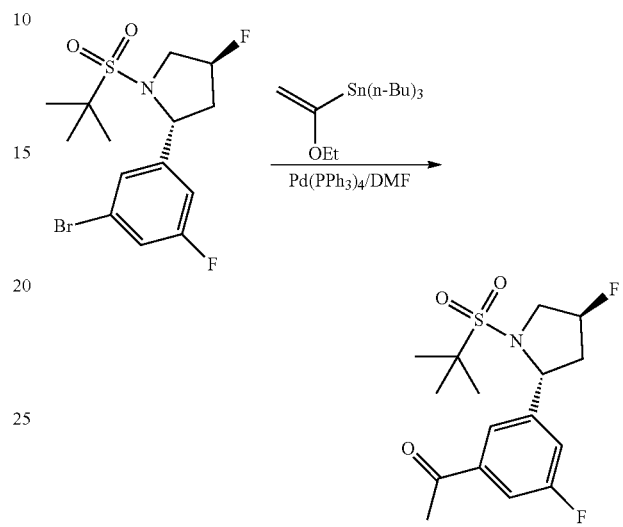

To a mixture of (2R,4S)-2-(3-bromo-5-fluorophenyl)-1-(tert-butylsulfonyl)-4-fluoropyrrolidine (200.00 mg, 523.20 umol, 1.00 eq) in toluene (5.00 mL) was added Pd(PPh₃)₄ (60.46 mg, 52.32 umol, 0.10 eq) and tributyl(1-ethoxyvinyl)stannane (226.74 mg, 627.84 umol, 211.91 uL, 1.20 eq). The mixture was stirred at 110° C. for 16 hrs under N₂. The mixture was concentrated to give the crude product. The crude product was purified by prep-TLC (PE:EtOAc=3:1) to give 1-(3-((2R,4S)-1-(tert-butylsulfonyl)-4-fluoropyrrolidin-2-yl)-5-fluorophenyl)ethan-1-one (150.00 mg, 434.28 umol, yield: 83.00%) as a yellow oil.

Step 2: 1-(3-fluoro-5-((2R,4S)-4-fluoropyrrolidin-2-yl)phenyl)ethan-1-one

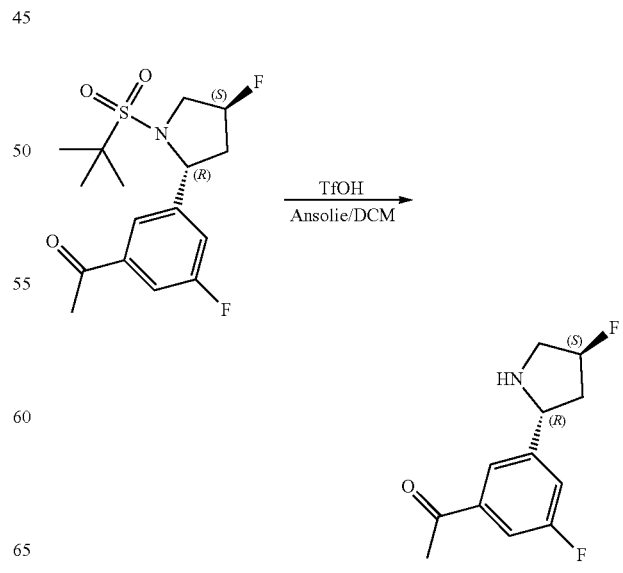

To a mixture of TfOH (195.53 mg, 1.30 mmol, 115.02 uL, 3.00 eq) in DCM (5.00 mL) was added anisole (70.44 mg, 651.42 umol, 70.44 uL, 1.50 eq) at −40° C. Then a solution of 1-(3-((2R,4S)-1-(tert-butylsulfonyl)-4-fluoropyrrolidin-2-yl)-5-fluorophenyl)ethan-1-one (150.00 mg, 434.28 umol, 1.00 eq) in DCM (5.00 mL) was added to the above solution. After addition, the mixture was stirred at 25° C. for 2 hrs. TLC (PE:EtOAc=3:1) showed the reaction was complete. Saturated aq. K$_2$CO$_3$ (3 mL) was added to the mixture, which was then extracted with DCM (3 mL*2). The organic layer was concentrated to give 1-(3-fluoro-5-((2R,4S)-4-fluoropyrrolidin-2-yl)phenyl)ethan-1-one (100.00 mg, crude) as a yellow oil.

Step 3: 5-((2R,4S)-2-(3-acetyl-5-fluorophenyl)-4-fluoropyrrolidin-1-yl)pyrazolo[1,5-a]pyrimidine-3-carbonitrile

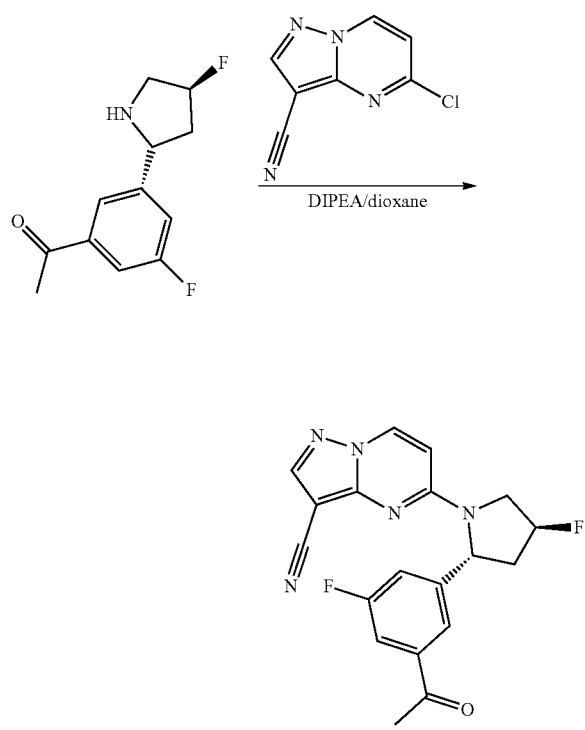

To a mixture of 5-chloropyrazolo[1,5-a]pyrimidine-3-carbonitrile (80.00 mg, 447.98 umol, 1.00 eq) in dioxane (5.00 mL) was added DIPEA (173.69 mg, 1.34 mmol, 234.72 uL, 3.00 eq) and 1-(3-fluoro-5-((2R,4S)-4-fluoropyrrolidin-2-yl)phenyl)ethan-1-one (99.89 mg, 443.50 umol, 0.99 eq). The mixture was stirred at 100° C. for 2 hrs. LCMS showed the reaction was complete. The mixture was concentrated to give the crude product. The crude product was purified by prep-TLC (PE:EtOAc=1:1) to give 5-((2R,4S)-2-(3-acetyl-5-fluorophenyl)-4-fluoropyrrolidin-1-yl)pyrazolo[1,5-a]pyrimidine-3-carbonitrile (100.00 mg, 272.22 umol, yield: 60.77%) as a yellow oil.

Step 4: 5-((2R,4S)-4-fluoro-2-(3-fluoro-5-(2-hydroxypropan-2-yl)phenyl)pyrrolidin-1-yl)pyrazolo[1,5-a]pyrimidine-3-carbonitrile

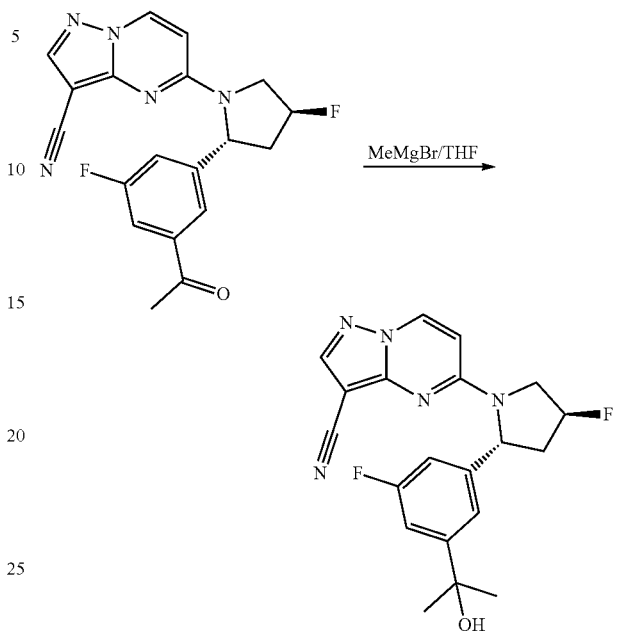

To a mixture of 5-((2R,4S)-2-(3-acetyl-5-fluorophenyl)-4-fluoropyrrolidin-1-yl)pyrazolo [1,5-a]pyrimidine-3-carbonitrile (50.00 mg, 136.11 umol, 1.00 eq) in THF (5.00 mL) was added dropwise MeMgBr (3 M, 136.11 uL, 3.00 eq) at −78° C. After addition, the mixture was stirred at 25° C. for 16 hrs. HPLC showed the starting material was about 60% consumed. The mixture was added to MeOH (2 mL) and then concentrated to give the crude product. The crude product was purified by prep-HPLC (TFA) to give 5-((2R,4S)-4-fluoro-2-(3-fluoro-5-(2-hydroxypropan-2-yl)phenyl) pyrrolidin-1-yl)pyrazolo[1,5-a]pyrimidine-3-carbonitrile (14.00 mg, 36.52 umol, yield: 26.83%) as a white solid. $^1$H-NMR (400 MHz, CD$_3$OD) δ ppm 8.35 (br.s, 1H), 8.11 (s, 1H), 7.28 (s, 1H), 7.10 (d, 1H, J=8.0 Hz), 6.91 (d, 1H, J=8.8 Hz), 6.17 (br.s, 1H), 5.42 (d, 1H, J=52.4 Hz), 5.23 (br.s, 1H), 4.16-4.08 (m, 1H), 2.91 (br.s, 1H), 2.31-2.17 (m, 1H), 1.47 (d, 6H, J=3.6 Hz). MS Calcd.: 383.4, MS Found: 384.1, 406.0 ([M+1]$^+$ and [M+23]$^+$).

Example 9: 3-((2R,4S)-1-(3-cyanopyrazolo[1,5-a]pyrimidin-5-yl)-4-fluoropyrrolidin-2-yl)-5-fluoro-N-methylbenzamide (Compound 20)

Step 1: Methyl 3-((2R,4S)-1-(tert-butylsulfonyl)-4-fluoropyrrolidin-2-yl)-5-fluorobenzoate

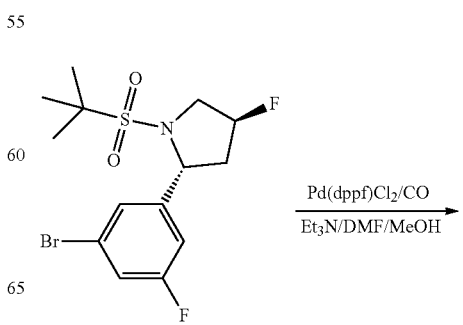

-continued

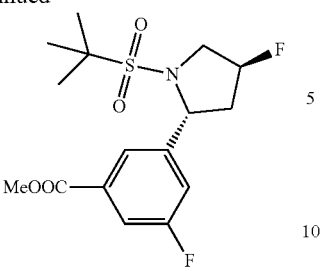

To a mixture of (2R,4S)-2-(3-bromo-5-fluorophenyl)-1-(tert-butylsulfonyl)-4-fluoropyrrolidine (2.00 g, 5.23 mmol, 1.00 eq) in MeOH (10.00 mL) was added Et₃N (1.59 g, 15.70 mmol, 3.00 eq), Pd(dppf)Cl₂ (191.41 mg, 261.60 umol, 0.05 eq). The mixture was stirred at 70° C. for 16 hrs under CO (50 Psi). The mixture was filtered and the filtrate was concentrated to give the crude product. The crude product was purified by column chromatography on silica gel (PE:EtOAc=15:1-8:1) to give methyl 3-((2R,4S)-1-(tert-butylsulfonyl)-4-fluoropyrrolidin-2-yl)-5-fluorobenzoate (1.20 g, 3.32 mmol, yield: 63.46%) as a red solid.

Step 2: Methyl 3-fluoro-5-((2R,4S)-4-fluoropyrrolidin-2-yl)benzoate

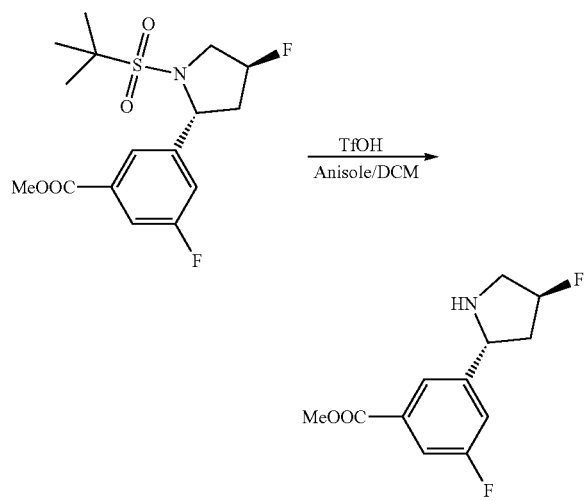

To a mixture of TfOH (1.37 g, 9.12 mmol, 3.00 eq) in DCM (50.00 mL) was added anisole (493.12 mg, 4.56 mmol, 1.50 eq) at −40° C. Then a solution of methyl 3-((2R,4S)-1-(tert-butylsulfonyl)-4-fluoropyrrolidin-2-yl)-5-fluorobenzoate (1.10 g, 3.04 mmol, 1.00 eq) in DCM (30.00 mL) was added dropwise to the mixture at −40° C. over 0.1 hr. After addition, the mixture was warmed to 0° C. and stirred at 0° C. for 1 hr. The mixture was added to K₂CO₃ (aq. 10 mL) and stirred for 0.1 hr. The mixture was extracted with DCM (10 mL*2). The organic layer was concentrated and then HCl/EtOAc (10 mL, 4 M) was added. The resulting mixture was stirred at 20° C. for 0.5 hr and filtered. The filter cake was dried in vacuum to give methyl 3-fluoro-5-((2R,4S)-4-fluoropyrrolidin-2-yl)benzoate (550.00 mg, crude, HCl) as a yellow solid.

Step 3: Methyl 3-((2R,4S)-1-(3-cyanopyrazolo[1,5-a]pyrimidin-5-yl)-4-fluoropyrrolidin-2-yl)-5-fluorobenzoate

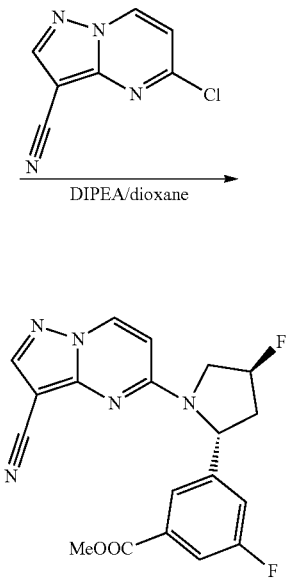

To a mixture of methyl 3-fluoro-5-((2R,4S)-4-fluoropyrrolidin-2-yl)benzoate (400.00 mg, 2.24 mmol, 1.00 eq) in dioxane (50.00 mL) was added DIPEA (868.45 mg, 6.72 mmol, 3.00 eq) and 5-chloropyrazolo[1,5-a]pyrimidine-3-carbonitrile (540.00 mg, 2.24 mmol, 1.00 eq). The mixture was stirred at 100° C. for 16 hrs. The mixture was concentrated to give the crude product. The crude product was purified by column chromatography on silica gel (PE:EtOAc=10:1-3:1) to give methyl 3-((2R,4S)-1-(3-cyanopyrazolo[1,5-a]pyrimidin-5-yl)-4-fluoropyrrolidin-2-yl)-5-fluorobenzoate (650.00 mg, 1.70 mmol, yield: 75.89%) as a yellow oil. ¹H-NMR (400 MHz, CD₃OD) δ ppm 8.30-8.24 (m, 1H), 6.94-6.83 (m, 2H), 5.64 (t, 1H, J=9.2 Hz), 5.41 (d, 1H, J=52.0 Hz), 4.48-4.38 (m, 2H), 3.97 (s, 3H), 2.79-2.69 (m, 1H), 2.20-2.06 (m, 1H).

Step 4: 3-((2R,4S)-1-(3-cyanopyrazolo[1,5-a]pyrimidin-5-yl)-4-fluoropyrrolidin-2-yl)-5-fluorobenzoic acid

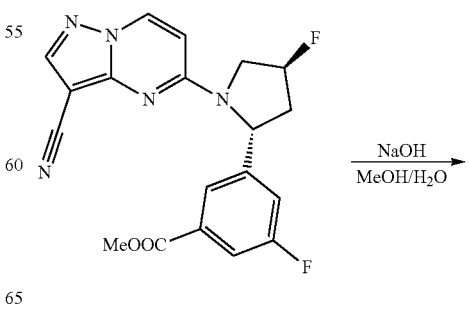

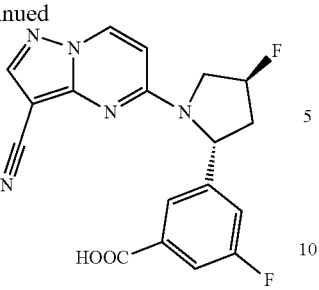

To a mixture of methyl 3-((2R,4S)-1-(3-cyanopyrazolo[1,5-a]pyrimidin-5-yl)-4-fluoropyrrolidin-2-yl)-5-fluorobenzoate (530.00 mg, 1.38 mmol, 1.00 eq) in MeOH/H$_2$O (20.00 mL, v:v=3:1) was added NaOH (110.40 mg, 2.76 mmol, 2.00 eq). The mixture was stirred at 20° C. for 16 hrs. The mixture was concentrated to remove MeOH. To the water layer was added HCl (2 M) until the pH was below 7. The water layer was then extracted with EtOAc (3 mL*3). The resulting organic layer was dried over Na$_2$SO$_4$ and concentrated to give 3-((2R,4S)-1-(3-cyanopyrazolo[1,5-a]pyrimidin-5-yl)-4-fluoropyrrolidin-2-yl)-5-fluorobenzoic acid (400.00 mg, 1.08 mmol, yield: 78.48%) as a white solid.

Step 5: 3-((2R,4S)-1-(3-cyanopyrazolo[1,5-a]pyrimidin-5-yl)-4-fluoropyrrolidin-2-yl)-5-fluoro-N-methylbenzamide

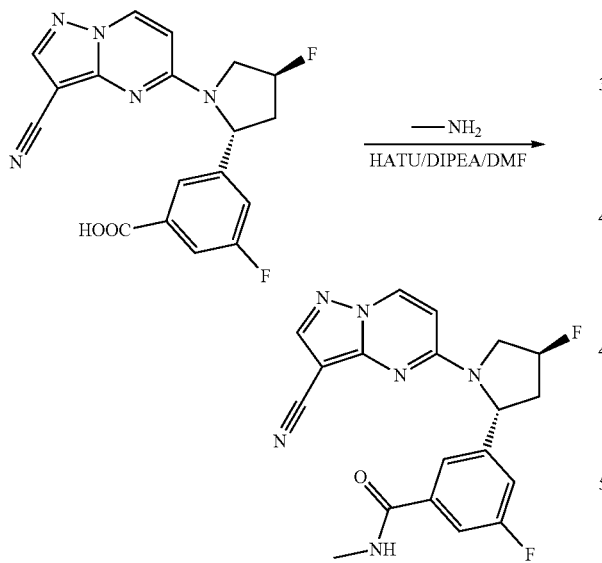

To a mixture of 3-((2R,4S)-1-(3-cyanopyrazolo[1,5-a]pyrimidin-5-yl)-4-fluoropyrrolidin-2-yl)-5-fluorobenzoic acid (80.00 mg, 216.61 umol, 1.00 eq) in DMF (2.00 mL) was added DIPEA (83.99 mg, 649.84 umol, 113.49 uL, 3.00 eq), HATU (98.84 mg, 259.94 umol, 1.20 eq) and methanamine (17.55 mg, 259.93 umol, 1.20 eq, HCl). The mixture was stirred at 20° C. for 1 hr. LCMS showed the reaction was complete. The mixture was then concentrated to give the crude product. The crude product was purified by prep-HPLC (TFA) to give 3-((2R,4S)-1-(3-cyanopyrazolo[1,5-a]pyrimidin-5-yl)-4-fluoropyrrolidin-2-yl)-5-fluoro-N-methylbenzamide (50.70 mg, 102.14 umol, yield: 47.15%, TFA) as a brown oil.

Example 10: 2-((2R,4S)-1-(3-cyanopyrazolo[1,5-a]pyrimidin-5-yl)-4-fluoropyrrolidin-2-yl)-4-fluorobenzamide (Compound 22)

Step 1: 5-((2R,4S)-2-(2-bromo-5-fluorophenyl)-4-fluoropyrrolidin-1-yl)pyrazolo[1,5-a]pyrimidine-3-carbonitrile

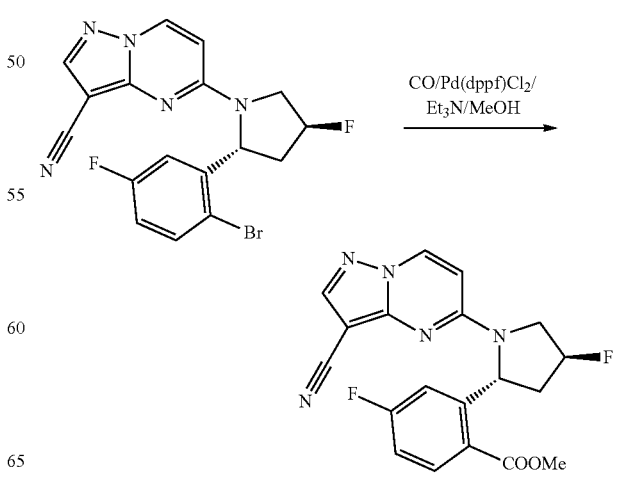

A mixture of 5-chloropyrazolo[1,5-a]pyrimidine-3-carbonitrile (500.00 mg, 2.33 mmol, 1.00 eq, HCl), (2R,4S)-2-(2-bromo-5-fluoro-phenyl)-4-fluoro-pyrrolidine (694.17 mg, 2.33 mmol, 1.00 eq, HCl), DIPEA (751.26 mg, 5.81 mmol, 1.02 mL, 2.50 eq) in dioxane (8.00 mL) was stirred at 80° C. for 16 hrs. TLC (PE:EtOAc=3:1) showed the reaction was complete. To the mixture was added H$_2$O (10 mL), and then the mixture was extracted with EtOAc (10 mL*3). The combined organic layers were dried over Na$_2$SO$_4$, concentrated in vacuum to get 5-((2R,4S)-2-(2-bromo-5-fluorophenyl)-4-fluoropyrrolidin-1-yl)pyrazolo[1,5-a]pyrimidine-3-carbonitrile (1.00 g, crude) as a yellow oil.

Step 2: Methyl 2-((2R,4S)-1-(3-cyanopyrazolo[1,5-a]pyrimidin-5-yl)-4-fluoropyrrolidin-2-yl)-4-fluorobenzoate A mixture of 5-((2R,4S)-2-(2-bromo-5-fluorophenyl)-4-fluoropyrrolidin-1-yl)pyrazolo[1,5-a]pyrimidine-3-carbonitrile (900.00 mg, 2.23 mmol, 1.00 eq), Pd(dppf)Cl₂ (326.34 mg, 446.00 umol, 0.20 eq), Et₃N (676.96 mg, 6.69 mmol, 927.34 uL, 3.00 eq) in MeOH (10.00 mL) was degassed and purged with CO 3 times. Then the mixture was stirred at 70° C. for 120 hrs under CO (50 psi) atmosphere. LCMS showed most of the starting material was consumed. The mixture was then filtered, and the filtrate was concentrated under vacuum to yield methyl 2-((2R,4S)-1-(3-cyanopyrazolo[1,5-a]pyrimidin-5-yl)-4-fluoropyrrolidin-2-yl)-4-fluorobenzoate (700.00 mg, crude) as a yellow solid.

Step 3: 2-((2R,4S)-1-(3-cyanopyrazolo[1,5-a]pyrimidin-5-yl)-4-fluoropyrrolidin-2-yl)-4-fluorobenzoic acid

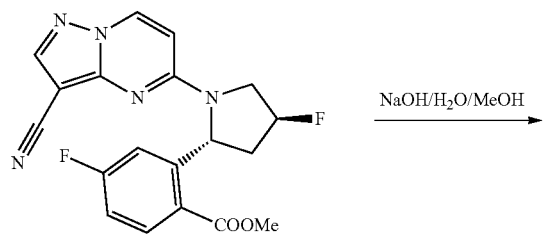

A mixture of methyl 2-((2R,4S)-1-(3-cyanopyrazolo[1,5-a]pyrimidin-5-yl)-4-fluoropyrrolidin-2-yl)-4-fluorobenzoate (700.00 mg, 1.83 mmol, 1.00 eq), NaOH (146.08 mg, 3.65 mmol, 2.00 eq) in MeOH (5.00 mL) and H₂O (5.00 mL) was stirred at 25° C. for 16 hrs. LCMS showed the reaction was complete. MeOH was removed under vacuum and then diluted HCl (1 M) was added to the mixture until pH=6 causing a yellow precipitate to form. The precipitate was collected and dried under vacuum to yield 2-((2R,4S)-1-(3-cyanopyrazolo[1,5-a]pyrimidin-5-yl)-4-fluoropyrrolidin-2-yl)-4-fluorobenzoic acid (280.00 mg, 758.15 umol, yield: 41.43%) as a yellow solid.

Step 4: 2-((2R,4S)-1-(3-cyanopyrazolo[1,5-a]pyrimidin-5-yl)-4-fluoropyrrolidin-2-yl)-4-fluorobenzamide

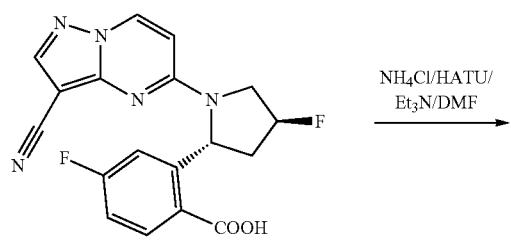

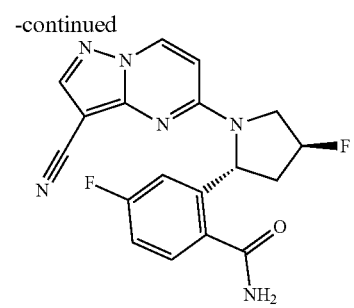

A mixture of 2-((2R,4S)-1-(3-cyanopyrazolo[1,5-a]pyrimidin-5-yl)-4-fluoropyrrolidin-2-yl)-4-fluorobenzoic acid (100.00 mg, 270.77 umol, 1.00 eq), NH₄Cl (43.45 mg, 812.31 umol, 28.40 uL, 3.00 eq), HATU (113.25 mg, 297.85 umol, 1.10 eq) and Et₃N (82.20 mg, 812.31 umol, 112.60 uL, 3.00 eq) in DMF (2.00 mL) was stirred at 25° C. for 16 hrs. LCMS showed the reaction was complete. The mixture was then concentrated under vacuum and purified by prep-HPLC (TFA) to produce 2-((2R,4S)-1-(3-cyanopyrazolo[1,5-a]pyrimidin-5-yl)-4-fluoropyrrolidin-2-yl)-4-fluorobenzamide (26.70 mg, 72.49 umol, yield: 26.77%) as a yellow oil.

Example 11: Synthesis of Intermediates 4-fluoro-2-arylpyrrolidine

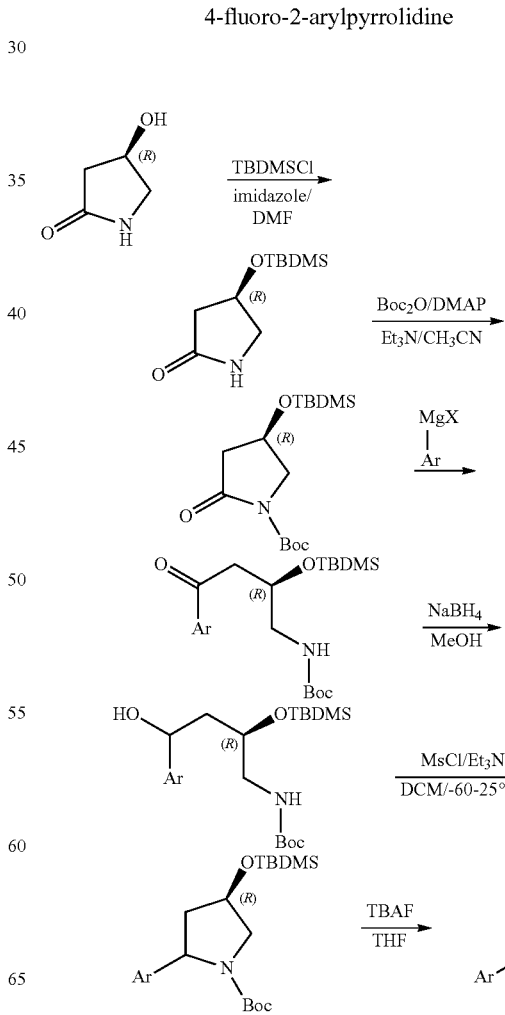

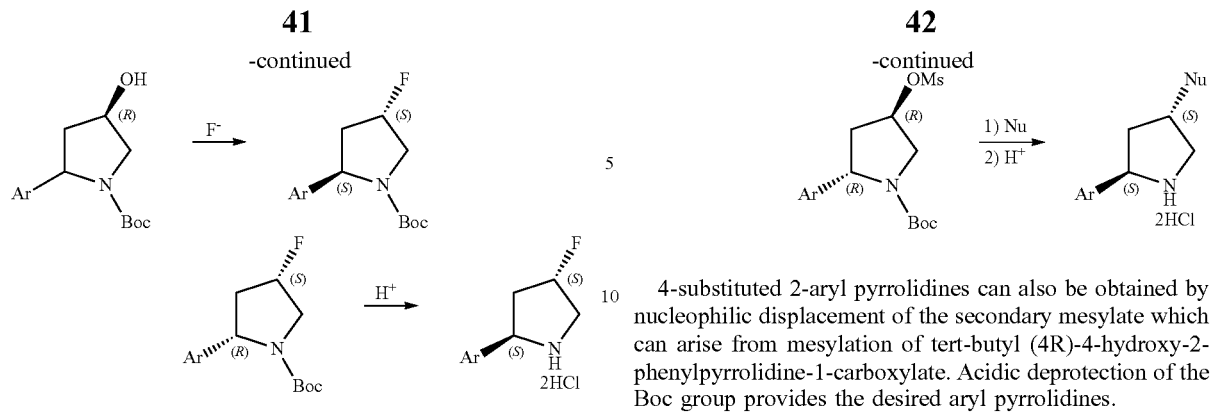

The general synthesis of 4-fluoro-2-arylpyrrolidine is shown above. (R)-4-Hydroxypyrrolidin-2-one is protected with a silyl group such as TBS while the lactam is protected with a suitable protecting group such as Boc. A nucleophilic Grignard reagent opens the lactam to give the di-protected 4-amino-3-hydroxy-1-phenylbutan-1-one. The ketone is reduced to the secondary alcohol with a reducing reagent such as sodium borohydride. Conversion of the alcohol to a leaving group, for example by forming the mesylate, leads to ring closure giving di-protected 4-fluoro-2-hydroxypyrrolidines. Alcohol deprotection with a fluoride source or acid followed by reaction with nucleophilic fluorine such as DAST or BAST gives the fluoro pyrrolidine, which can be deprotected under acid conditions, such as with TBAF, to provide the desired 4-fluoro-2-arylpyrrolidines.

(R)-4,4-Difluoro-2-phenylpyrrolidines

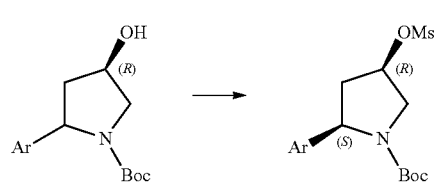

(R)-4,4-Difluoro-2-phenylpyrrolidines are prepared as shown above from tert-butyl (4R)-4-hydroxy-2-phenylpyrrolidine-1-carboxylate via oxidation of the secondary alcohol to a ketone with an oxidating reagent, such as TEMPO or Dess-Martin periodinane, followed by fluorination with a reagent such as DAST. Acidic deprotection of the Boc group provides the desired aryl pyrrolidine.

4-substituted 2-aryl pyrrolidines can also be obtained by nucleophilic displacement of the secondary mesylate which can arise from mesylation of tert-butyl (4R)-4-hydroxy-2-phenylpyrrolidine-1-carboxylate. Acidic deprotection of the Boc group provides the desired aryl pyrrolidines.

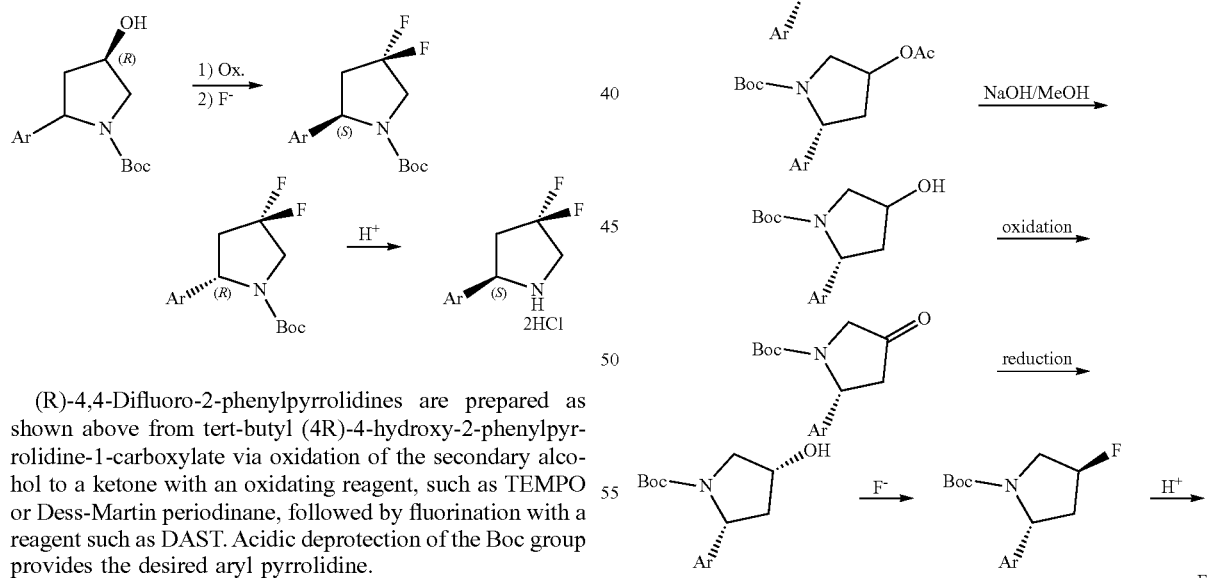

An additional method for preparing 4-fluoro-2-arylpyrrolidines involves formation of sulfinamides from benzaldehydes, which are stereoselectively reacted with allyl nucleophiles, such as allylzinc or allyl Grignard reagents. Conversion to the free amine under acidic conditions followed by acetylation and ring closure with iodine provides 2-aryl pyrrolidines. Protection of the amine with a group such as Boc, deprotection of the acetate and oxidation with a reagent such as TEMPO or Dess-Martin periodinane provides the ketone which can be selectively reduced to the secondary alcohol with sodium borohydride. Fluorination followed by amine deprotection provides the desired aryl pyrrolidines.

3-Fluoro-5-((2R,4S)-4-fluoropyrrolidin-2-yl)pyridine

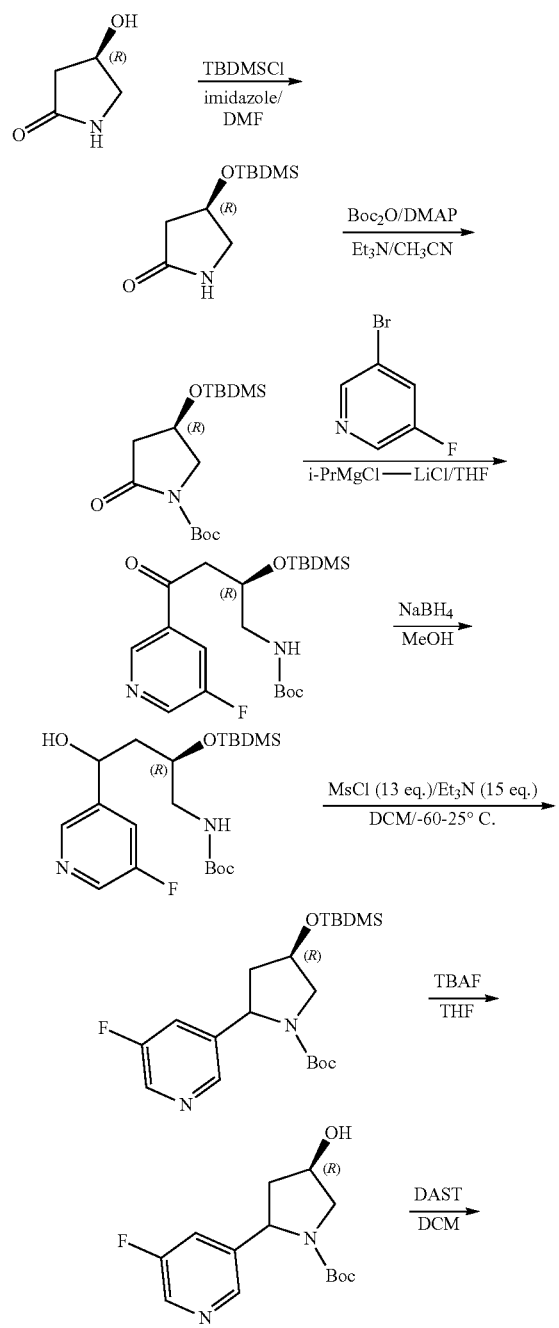

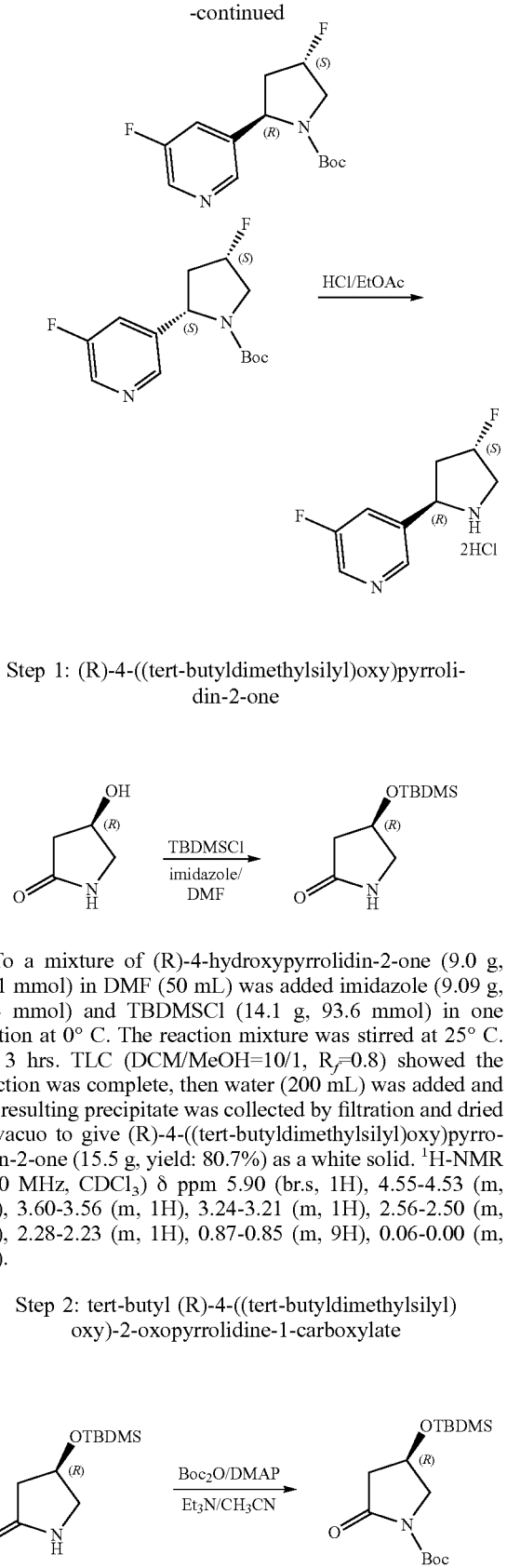

Step 1: (R)-4-((tert-butyldimethylsilyl)oxy)pyrrolidin-2-one

To a mixture of (R)-4-hydroxypyrrolidin-2-one (9.0 g, 89.1 mmol) in DMF (50 mL) was added imidazole (9.09 g, 134 mmol) and TBDMSCl (14.1 g, 93.6 mmol) in one portion at 0° C. The reaction mixture was stirred at 25° C. for 3 hrs. TLC (DCM/MeOH=10/1, $R_f$=0.8) showed the reaction was complete, then water (200 mL) was added and the resulting precipitate was collected by filtration and dried in vacuo to give (R)-4-((tert-butyldimethylsilyl)oxy)pyrrolidin-2-one (15.5 g, yield: 80.7%) as a white solid. $^1$H-NMR (400 MHz, CDCl$_3$) δ ppm 5.90 (br.s, 1H), 4.55-4.53 (m, 1H), 3.60-3.56 (m, 1H), 3.24-3.21 (m, 1H), 2.56-2.50 (m, 1H), 2.28-2.23 (m, 1H), 0.87-0.85 (m, 9H), 0.06-0.00 (m, 6H).

Step 2: tert-butyl (R)-4-((tert-butyldimethylsilyl)oxy)-2-oxopyrrolidine-1-carboxylate To the mixture of (R)-4-((tert-butyldimethylsilyl)oxy)pyrrolidin-2-one (15.5 g, 72.0 mmol) in CH$_3$CN (150 mL) was added Et₃N (8.72 g, 86.4 mmol), DMAP (4.39 g, 36 mmol), and Boc₂O (20.4 g, 93.7 mmol) in one portion at 0° C. The reaction mixture was stirred at 25° C. for 10 hrs. TLC (PE/EtOAc=3/1) showed the reaction was complete, then water (600 mL) was added, and the resulting precipitate was collected by filtration and dried in vacuo to give tert-butyl (R)-4-((tert-butyldimethylsilyl)oxy)-2-oxopyrrolidine-1-carboxylate (19.2 g, yield: 84.6%) as a pink solid. ¹H-NMR (400 MHz, CDCl₃) δ ppm 4.33-4.30 (m, 1H), 3.81-3.77 (m, 1H), 3.56-3.54 (m, 1H), 2.67-2.61 (m, 1H), 2.41-2.37 (m, 1H), 1.46 (s, 9H), 0.80 (s, 9H), 0.00 (s, 6H).

Step 3: tert-butyl ((2R)-2-((tert-butyldimethylsilyl)oxy)-4-(5-fluoropyridin-3-yl)-4-hydroxybutyl)carbamate

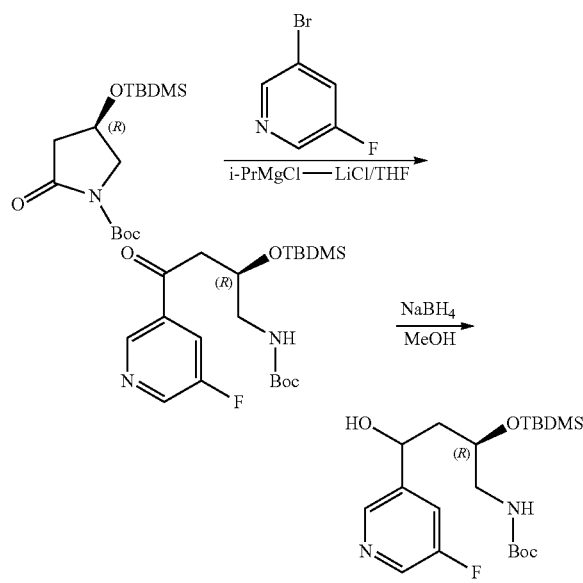

To the mixture of 3-bromo-5-fluoro-pyridine (3.35 g, 19.02 mmol, 1.20 eq) in THF (40.00 mL) was added i-PrMgCl—LiCl (1.3 M, 17.56 mL, 1.44 eq) dropwise at 0° C. over 30 minutes (exothermic). After addition, the temperature was raised to 25° C. over 1 hr and stirred at 25° C. for 30 mins. TLC (PE/EtOAc=10/1) showed a new spot was generated indicating that the Mg reagent was prepared successfully. Tert-butyl (R)-4-((tert-butyldimethylsilyl)oxy)-2-oxopyrrolidine-1-carboxylate (5.00 g, 15.85 mmol, 1.00 eq) in THF (50 mL) was then added dropwise to the solution at −78° C. over 30 mins. The mixture was allowed to warm to 25° C. over 1 hr, then stirred at 25° C. for 16 hrs. TLC (PE/EtOAc=3/1) showed the starting material was consumed completely and the desired product, tert-butyl (R)-(2-((tert-butyldimethylsilyl)oxy)-4-(5-fluoropyridin-3-yl)-4-oxobutyl)carbamate, was detected. The reaction mixture was quenched by addition of MeOH (50 mL) at 0° C. NaBH₄ (1.20 g, 31.70 mmol, 2.00 eq) was added at 0° C., then the mixture was stirred at 25° C. for 4 hrs. TLC (PE/EtOAc=2/1) and LCMS showed the reaction was complete. The combined reaction mixture (4 parallel reactions) was quenched by aqueous NH₄Cl (400 mL) and extracted with EtOAc (600 mL*3). The combined organics were dried over Na₂SO₄ and concentrated in vacuo, and the residue was purified by HPLC to give tert-butyl ((2R)-2-((tert-butyldimethylsilyl)oxy)-4-(5-fluoropyridin-3-yl)-4-hydroxybutyl) carbamate (1.24 g, yield: 18.91%) as a yellow oil. ¹H-NMR (400 MHz, CDCl₃) δ ppm 8.26-8.22 (m, 2H), 7.37 (d, 1H, J=8.8 Hz), 4.95-4.88 (m, 2H), 4.69 (br.s, 1H), 4.00-3.98 (m, 2H), 3.23-3.10 (m, 2H), 1.73 (br.s, 2H), 1.32 (s, 9H), 0.80-0.79 (m, 9H), 0.00 (s, 6H).

Step 4: tert-butyl (4R)-4-((tert-butyldimethylsilyl)oxy)-2-(5-fluoropyridin-3-yl)pyrrolidine-1-carboxylate

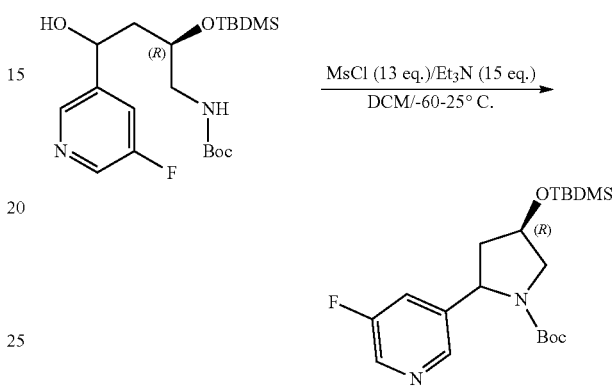

To a mixture of tert-butyl ((2R)-2-((tert-butyldimethylsilyl)oxy)-4-(5-fluoropyridin-3-yl)-4-hydroxybutyl)carbamate (8.70 g, 20.98 mmol, 1.00 eq) and Et₃N (31.84 g, 314.70 mmol, 15.00 eq) in DCM (500.00 mL) was added dropwise MsCl (31.24 g, 272.74 mmol, 13.00 eq) at −60° C. over 0.5 hr. The mixture was then stirred at −60 OC for 1 hr, and the reaction mixture was allowed to warm to 25° C. and stirred for 18 hrs. LCMS showed the starting material was consumed completely. The mixture was then washed with H₂O (200 mL*3), and the aqueous phase was extracted with DCM (200 mL*4). The combined organic layers were dried over Na₂SO₄ and concentrated in vacuo to give crude product tert-butyl (4R)-4-((tert-butyldimethylsilyl)oxy)-2-(5-fluoropyridin-3-yl)pyrrolidine-1-carboxylate (8.30 g, crude) as a black/brown oil, which was used directly without purification.

Step 5: tert-butyl (4R)-2-(5-fluoropyridin-3-yl)-4-hydroxypyrrolidine-1-carboxylate

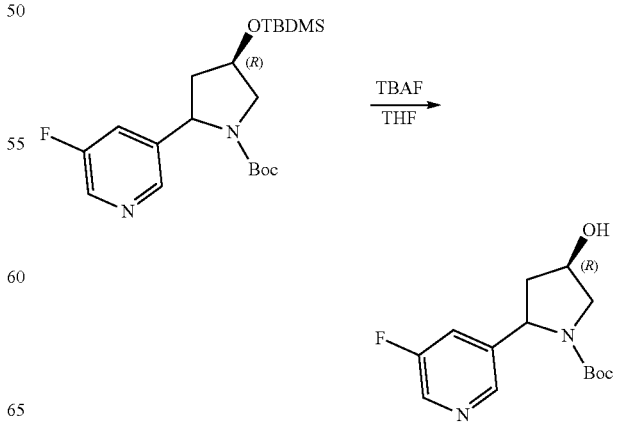

To the mixture of tert-butyl (4R)-4-((tert-butyldimethylsilyl)oxy)-2-(5-fluoropyridin-3-yl)pyrrolidine-1-carboxylate (8.30 g, 20.93 mmol, 1.00 eq) in THF (250.00 mL) was added TBAF (9.43 g, 41.86 mmol, 2.00 eq) at 25° C. The mixture was stirred at 25° C. for 16 hrs. After TLC (PE/EtOAc=1/1) showed the reaction was complete, the mixture was concentrated and the residue was dissolved in EtOAc (600 mL), washed with water (200 mL*5), dried over Na$_2$SO$_4$, and concentrated. The crude product was purified by HPLC to give tert-butyl (4R)-2-(5-fluoropyridin-3-yl)-4-hydroxypyrrolidine-1-carboxylate (4.70 g, 16.65 mmol, yield: 79.54%) as a brown black oil. $^1$H-NMR (400 MHz, CDCl$_3$) δ ppm 8.37-8.33 (m, 2H), 7.48 (br.s, 1H), 5.09-4.89 (m, 1H), 4.56-4.54 (m, 1H), 3.80-3.65 (m, 2H), 2.63-2.43 (m, 1H), 2.03-1.96 (m, 1H), 1.56-1.20 (m, 9H).

Step 6: tert-butyl (2R,4S)-4-fluoro-2-(5-fluoropyridin-3-yl)pyrrolidine-1-carboxylate

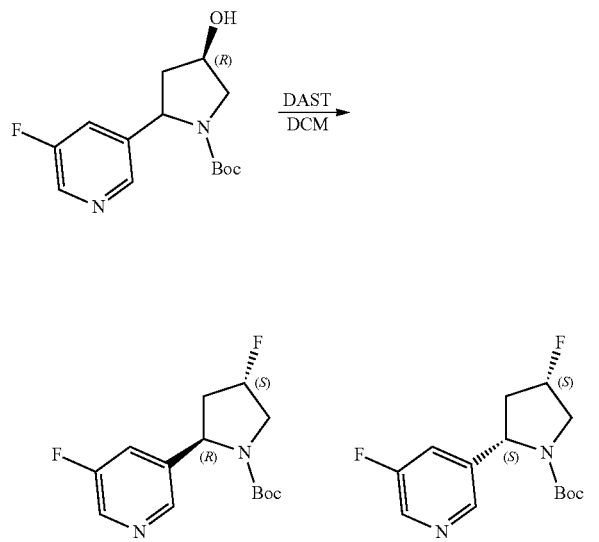

To a mixture of tert-butyl (4R)-2-(5-fluoropyridin-3-yl)-4-hydroxypyrrolidine-1-carboxylate (4.70 g, 16.65 mmol, 1.00 eq) in DCM (150.00 mL) was added DAST dropwise (29.52 g, 183.15 mmol, 11.00 eq) at −78° C. over 0.5 hr. The reaction mixture was stirred at −78° C. for 2 hrs, then allowed to warm to 25° C. and stirred for 20 hrs. After TLC (PE/EtOAc=0/1) showed the starting material was consumed completely, the mixture was cooled to 0° C. and quenched by saturated NaHCO$_3$ solution (100 mL) dropwise. The organic phase was separated and dried over Na$_2$SO$_4$, concentrated to give the residue, then purified by column chromatography on silica gel (PE:EtOAc from 10:1, 8:1 to 5:1, then 3:1) to give tert-butyl (2R,4S)-4-fluoro-2-(5-fluoropyridin-3-yl)pyrrolidine-1-carboxylate (1.38 g, 4.85 mmol, yield: 29.15%, R$_f$=0.53) as a white solid and tert-butyl (2S,4S)-4-fluoro-2-(5-fluoropyridin-3-yl)pyrrolidine-1-carboxylate (1.36 g, 4.78 mmol, yield: 28.73%, R$_f$=0.43) as a yellow oil. $^1$H-NMR (400 MHz, CDCl$_3$) δ ppm 8.31-8.27 (m, 2H), 7.20-7.18 (m, 1H), 5.18 (d, 1H, J=51.6 Hz), 4.97-4.88 (m, 1H), 4.04-4.00 (m, 1H), 3.64 (dd, 1H, J=38.8, 12.8 Hz), 2.67 (dd, 1H, J=15.6, 6.8 Hz), 1.97-1.67 (m, 1H), 1.56-1.12 (m, 9H).

Step 7: 3-Fluoro-5-((2R,4S)-4-fluoropyrrolidin-2-yl)pyridine

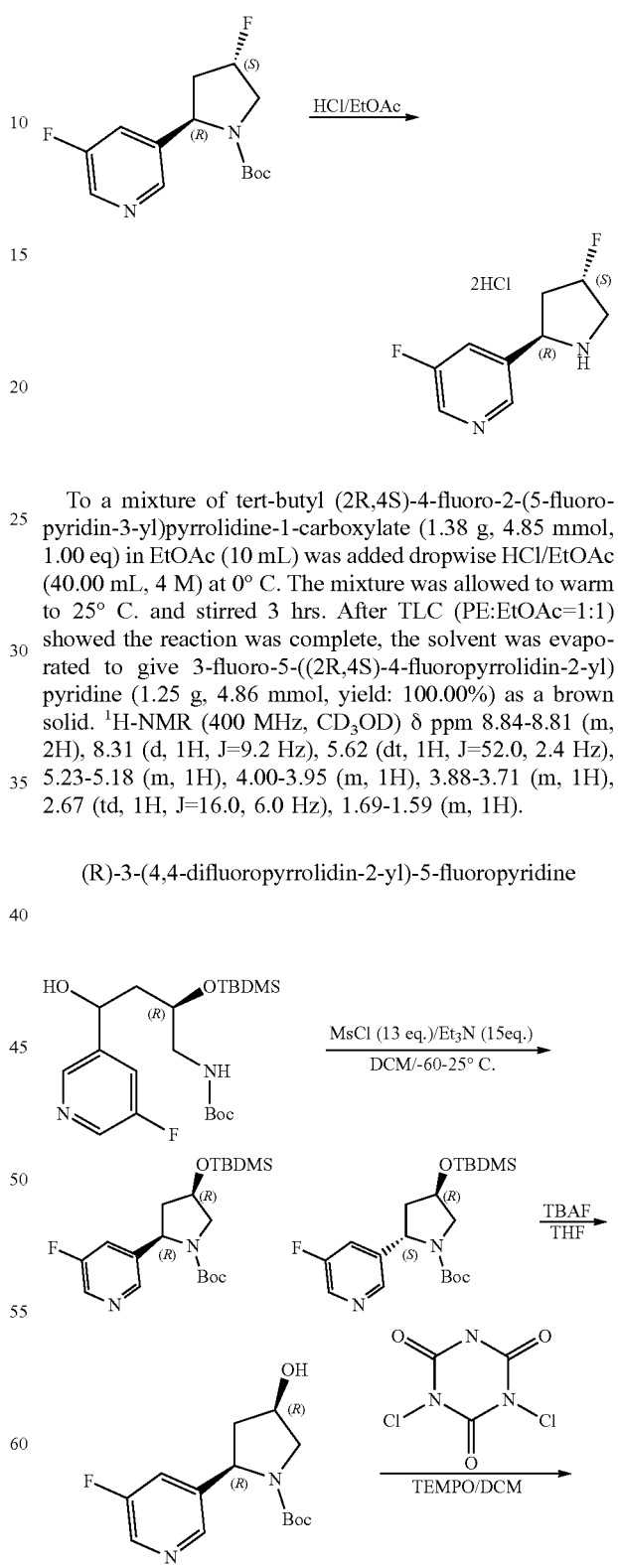

To a mixture of tert-butyl (2R,4S)-4-fluoro-2-(5-fluoropyridin-3-yl)pyrrolidine-1-carboxylate (1.38 g, 4.85 mmol, 1.00 eq) in EtOAc (10 mL) was added dropwise HCl/EtOAc (40.00 mL, 4 M) at 0° C. The mixture was allowed to warm to 25° C. and stirred 3 hrs. After TLC (PE:EtOAc=1:1) showed the reaction was complete, the solvent was evaporated to give 3-fluoro-5-((2R,4S)-4-fluoropyrrolidin-2-yl)pyridine (1.25 g, 4.86 mmol, yield: 100.00%) as a brown solid. $^1$H-NMR (400 MHz, CD$_3$OD) δ ppm 8.84-8.81 (m, 2H), 8.31 (d, 1H, J=9.2 Hz), 5.62 (dt, 1H, J=52.0, 2.4 Hz), 5.23-5.18 (m, 1H), 4.00-3.95 (m, 1H), 3.88-3.71 (m, 1H), 2.67 (td, 1H, J=16.0, 6.0 Hz), 1.69-1.59 (m, 1H).

(R)-3-(4,4-difluoropyrrolidin-2-yl)-5-fluoropyridine

1H), 2.62-2.58 (m, 1H), 2.04-2.01 (m, 1H), 1.56 (s, 3H), 1.32 (s, 6H), 0.99-0.88 (m, 9H), 0.18-0.00 (m, 6H).

Step 2: tert-butyl (2R,4R)-2-(5-fluoropyridin-3-yl)-4-hydroxypyrrolidine-1-carboxylate

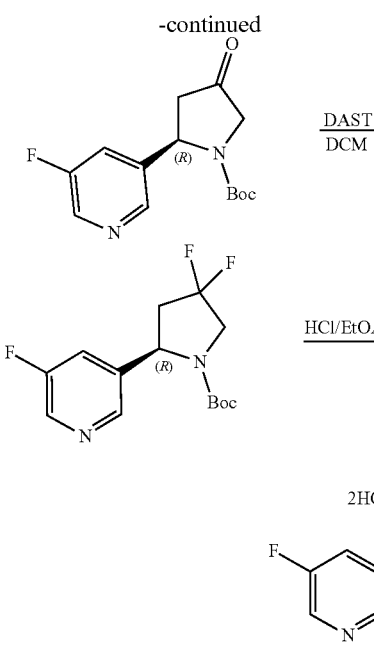

Step 1: tert-butyl (2R,4R)-4-((tert-butyldimethylsilyl)oxy)-2-(5-fluoropyridin-3-yl)pyrrolidine-1-carboxylate

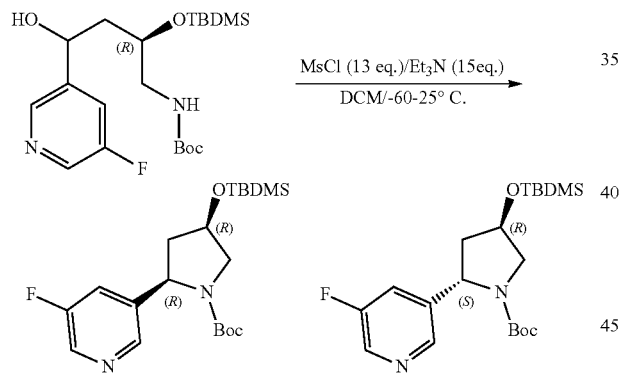

To a mixture of tert-butyl ((2R)-2-((tert-butyldimethylsilyl)oxy)-4-(5-fluoropyridin-3-yl)-4-hydroxybutyl)carbamate (6.80 g, 16.40 mmol) and Et₃N (24.89 g, 246.00 mmol) in DCM (500.00 mL) was added MsCl (24.42 g, 213.20 mmol) dropwise at −60° C. over 30 minutes. The mixture was stirred at −60° C. for 1 hr. The reaction mixture was allowed to warm to 25° C. and stirred for an additional 18 hrs. The mixture was washed with H₂O (200 mL*3). The aqueous phase was extracted with DCM (200 mL*4). The combined organic layers were dried over Na₂SO₄ and concentrated in vacuo. The residue was purified by silica gel chromatography (PE:EtOAc=50/1, 20/1, 10/1) to afford tert-butyl (2S,4R)-4-((tert-butyldimethylsilyl)oxy)-2-(5-fluoropyridin-3-yl)pyrrolidine-1-carboxylate (2.70 g, yield: 41.52%) and tert-butyl (2R,4R)-4-((tert-butyldimethylsilyl)oxy)-2-(5-fluoropyridin-3-yl)pyrrolidine-1-carboxylate (2.40 g, yield: 36.89%) as brown oil. 1H-NMR (400 MHz, CDCl3) δ ppm 8.40 (br.s, 2H), 7.56-7.45 (m, 1H), 5.11-4.94 (m, 2H), 4.53 (br.s, 1H), 3.85-3.79 (m, 1H), 3.66-3.53 (m, To a mixture of tert-butyl (2R,4R)-4-((tert-butyldimethylsilyl)oxy)-2-(5-fluoropyridin-3-yl)pyrrolidine-1-carboxylate (2.40 g, 6.05 mmol) in THF (60.00 mL) was added TBAF (3.16 g, 12.10 mmol) in one portion at 25° C. The mixture was concentrated under reduced pressure at 50° C. The residue was added to water (20 mL). The aqueous phase was extracted with ethyl acetate (30 mL*3). The combined organic phase was washed with saturated brine (20 mL*2), dried over Na₂SO₄, filtered and concentrated in vacuo. The residue was purified by silica gel chromatography (PE: EtOAc=20/1, 10/1, 1/3) to afford tert-butyl (2R,4R)-2-(5-fluoropyridin-3-yl)-4-hydroxypyrrolidine-1-carboxylate (1.30 g, yield: 76.11%) as a yellow solid. 1H-NMR (400 MHz, CDCl3) δ ppm 8.26 (d, 2H, J=12.8 Hz), 7.39 (br.s, 1H), 4.95-4.81 (m, 1H), 4.48-4.47 (m, 1H), 3.73 (br.s, 1H), 3.56-3.53 (m, 1H), 2.55 (br.s, 1H), 1.97-1.98 (m, 1H), 1.65-1.16 (m, 9H).

Step 3: tert-butyl (R)-2-(5-fluoropyridin-3-yl)-4-oxopyrrolidine-1-carboxylate

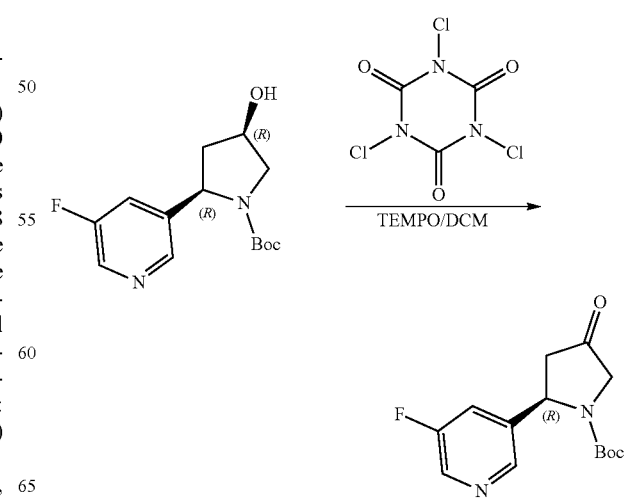

To a mixture of tert-butyl (2R,4R)-2-(5-fluoropyridin-3-yl)-4-hydroxypyrrolidine-1-carboxylate (1.30 g, 4.60 mmol) and trichloroisocyanuric acid (1.10 g, 4.60 mmol) was added TEMPO (72.41 mg, 460.49 umol) at −10° C. The mixture was stirred at −10° C. for 15 min, then warmed to 25° C. and stirred for 1 hr. TLC (EtOAc) showed the reaction was complete. The organic phase was washed with NaHCO$_3$ (20 mL*2), dried over Na$_2$SO$_4$, filtered and concentrated in vacuum. The residue was purified by silica gel chromatography (petroleum ether/ethyl acetate=50/1, 10/1) to afford tert-butyl (R)-2-(5-fluoropyridin-3-yl)-4-oxopyrrolidine-1-carboxylate (1.10 g, yield: 85.32%) as a brown oil.

Step 4: tert-butyl (R)-4,4-difluoro-2-(5-fluoropyridin-3-yl)pyrrolidine-1-carboxylate

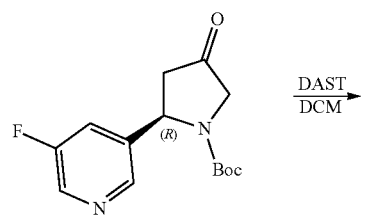

To a mixture of tert-butyl (R)-2-(5-fluoropyridin-3-yl)-4-oxopyrrolidine-1-carboxylate (1.00 g, 3.57 mmol) in DCM (100.00 mL) was added DAST (14.39 g, 89.25 mmol) dropwise at −70° C. under N$_2$. The mixture was stirred at −70° C. for 30 min. Then the mixture was stirred at 25° C. for 16 hrs. The reaction mixture was quenched by saturated aq. NaHCO$_3$ slowly at 0° C. and the aqueous phase was extracted with DCM (50 mL*4). The combined organic phase was washed with saturated brine (30 mL), dried over Na$_2$SO$_4$, filtered and concentrated in vacuo. The residue was purified by silica gel chromatography (petroleum ether/ethyl acetate=100/1, 30/1) to afford tert-butyl (R)-4,4-difluoro-2-(5-fluoropyridin-3-yl)pyrrolidine-1-carboxylate (1.00 g, yield: 92.66%) as a brown oil. 1H-NMR (400 MHz, CDCl3) δ ppm 8.40 (s, 1H), 8.34 (s, 1H), 7.30-7.21 (m, 1H), 5.06 (br.s, 1H), 4.14-3.85 (m, 2H), 2.91-2.84 (m, 1H), 2.39-2.32 (m, 1H), 1.43-1.14 (m, 9H).

Step 5: (R)-3-(4,4-difluoropyrrolidin-2-yl)-5-fluoropyridine

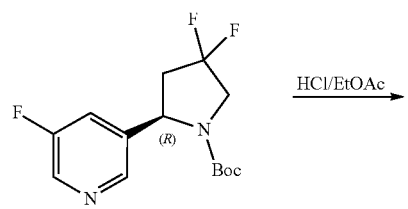

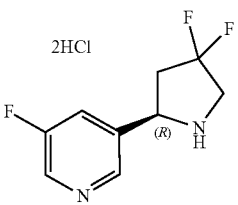

A mixture of tert-butyl (R)-4,4-difluoro-2-(5-fluoropyridin-3-yl)pyrrolidine-1-carboxylate (1.00 g, 3.31 mmol) in HCl/EtOAc (50.00 mL, 4 M) was stirred for 2 hrs at 25° C. The mixture was concentrated under reduced pressure at 30° C. to afford (R)-3-(4,4-difluoropyrrolidin-2-yl)-5-fluoropyridine (840.00 mg, yield: 92.25%) as a white solid as bis HCl salt. 1H-NMR (400 MHz, MeOD) δ ppm 8.68-8.63 (m, 1H), 7.97 (d, 1H, J=9.2 Hz), 5.26-5.21 (m, 1H), 4.03-3.90 (m, 2H), 3.13-2.92 (m, 2H).

(3S,5R)-5-(2,5-difluorophenyl)pyrrolidine-3-carbonitrile

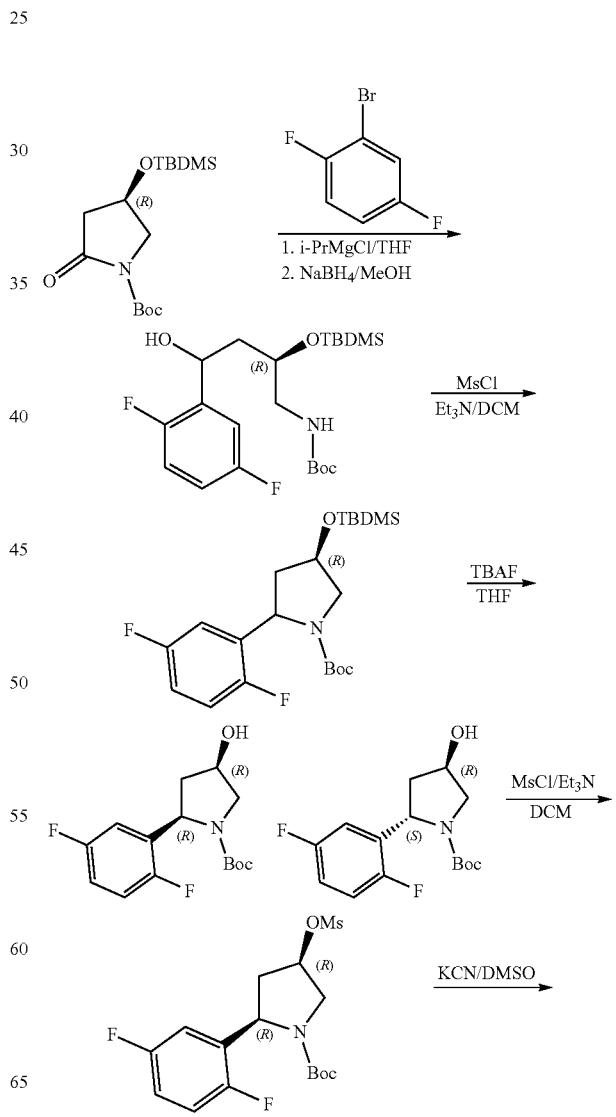

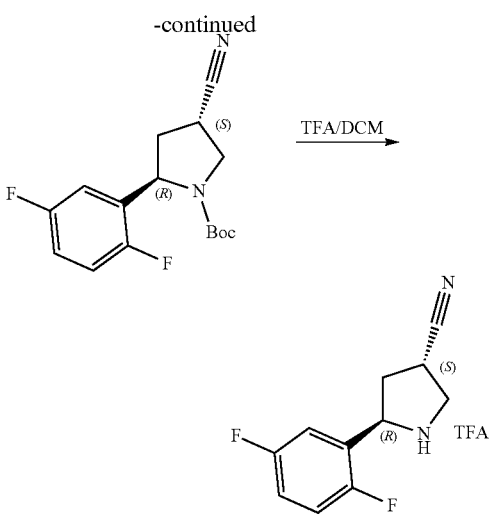

3.33-3.14 (m, 2H), 1.80-1.69 (m, 2H), 1.35 (s, 9H), 0.84-0.82 (9H, m), 0.04-0.03 (6H, m).

Step 2: tert-butyl (4R)-4-((tert-butyldimethylsilyl)oxy)-2-(2,5-difluorophenyl)pyrrolidine-1-carboxylate

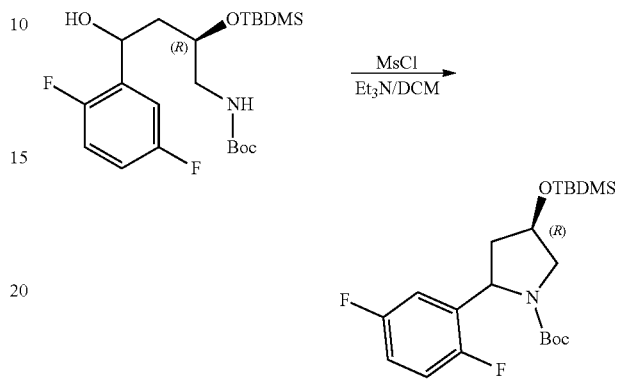

To a solution of tert-butyl ((2R)-2-((tert-butyldimethylsilyl)oxy)-4-(2,5-difluorophenyl)-4-hydroxybutyl)carbamate (13.40 g, 31.05 mmol, 1.00 Eq) and Et₃N (9.43 g, 93.14 mmol, 3.00 Eq) in DCM (50 mL) was added dropwise methanesulfonyl chloride (5.33 g, 46.57 mmol, 1.50 Eq) at −60° C. by under N₂. The mixture was stirred at −60° C. for 2 hrs and 15° C. for 16 hrs. LCMS showed the starting material was consumed completely. The reaction mixture was extracted with DCM (30 mL*2) and the combined organics were washed with brine (50 mL), dried over Na₂SO₄ and filtered, concentrated to give tert-butyl (4R)-4-((tert-butyldimethylsilyl)oxy)-2-(2,5-difluorophenyl)pyrrolidine-1-carboxylate (12.00 g, 26.11 mmol, yield: 84.10%, 90% purity) which was used directly without further purification.

Step 3: tert-butyl (2R,4R)-2-(2,5-difluorophenyl)-4-hydroxypyrrolidine-1-carboxylate Step 1: tert-butyl ((2R)-2-((tert-butyldimethylsilyl)oxy)-4-(2,5-difluorophenyl)-4-hydroxybutyl)carbamate

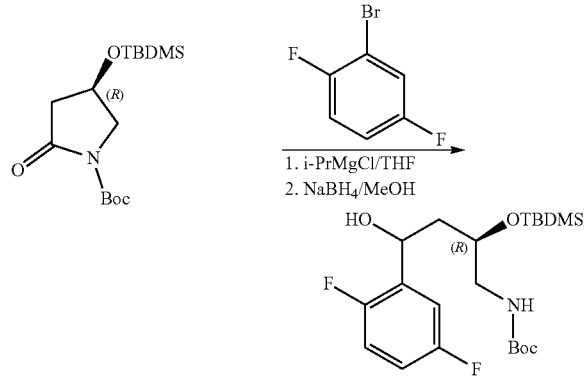

To a solution of 2-bromo-1,4-difluoro-benzene (3.01 g, 15.60 mmol, 1.20 Eq) in THF (15 mL) was added isopropylmagnesium chloride complex (2.27 g, 15.60 mmol, 1.20 Eq) at 0° C. dropwise under N₂. The reaction was stirred at 15° C. for 1 hr to prepare (2,5-difluorophenyl) magnesium bromide (23 mL). To a solution of tert-butyl (R)-4-((tert-butyldimethylsilyl)oxy)-2-oxopyrrolidine-1-carboxylate (4.10 g, 13.00 mmol, 1.00 Eq) in THF (50 mL) was added (2,5-difluorophenyl) magnesium bromide (23 mL) dropwise at 0° C. over 30 mins. The reaction mixture was stirred at 0° C. for 1 hr. Methanol (20 mL) was added to the mixture followed by NaBH₄ (738 mg, 19.50 mmol, 1.50 Eq) at 0° C. The mixture was stirred at 0° C. for 1 hr then poured into 10% aqueous NH₄Cl. The mixture was extracted with EtOAc (20 mL*2), the combined organic layers were washed with brine, dried over Na₂SO₄, filtered and concentrated. The crude product was purified by medium pressure liquid chromatography (MPLC) to give tert-butyl ((2R)-2-((tert-butyldimethylsilyl)oxy)-4-(2,5-difluorophenyl)-4-hydroxybutyl)carbamate (2.22 g, 5.14 mmol, 39.6% yield). ¹H-NMR (400 MHz, CDCl₃) δ ppm 7.17-7.15 (m, 1H), 6.86-6.79 (m, 2H), 5.11-5.06 (m, 1H), 4.70 (br.s, 1H), 4.02-3.98 (m, 1H), 3.69 (br.s, 0.5H), 3.46 (br.s, 0.5H),

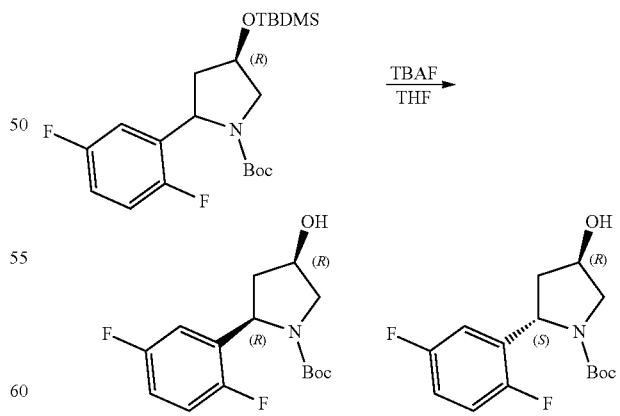

To a solution of tert-butyl (4R)-4-((tert-butyldimethylsilyl)oxy)-2-(2,5-difluorophenyl)pyrrolidine-1-carboxylate (4.50 g, 10.88 mmol, 1.00 Eq) in THF (30 mL) was added TBAF/THF (1 M, 14.15 mL, 1.30 Eq) at 15° C. The mixture was stirred at 15° C. for 16 hrs. TLC (PE:EtOAc=3:1)

showed the starting material was consumed completely. The reaction mixture was quenched by H₂O (50 mL), extracted with EtOAc (30 mL*2) and the combined organics were washed with brine (10 mL), dried over Na₂SO₄, filtered and concentrated in vacuo. The residue was purified by neutral prep-HPLC to afford tert-butyl (2R,4R)-2-(2,5-difluorophenyl)-4-hydroxypyrrolidine-1-carboxylate (1.00 g, 3.34 mmol, yield: 30.70%) as a white solid. ¹H-NMR (400 MHz, CDCl₃) δ ppm 7.04-6.80 (m, 3H), 5.10-5.00 (m, 1H), 4.43 (s, 1H), 3.75 (br.s, 1H), 3.53-3.49 (m, 1H), 2.53 (br.s, 1H), 1.93-1.90 (m, 1H), 1.40-1.16 (m, 9H).

Step 4: tert-butyl (2R,4R)-2-(2,5-difluorophenyl)-4-((methylsulfonyl)oxy)pyrrolidine-1-carboxylate

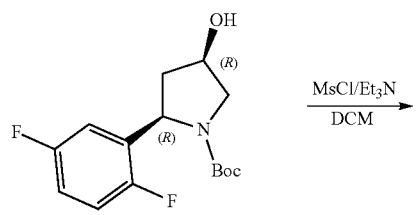

To a mixture of tert-butyl (2R,4R)-2-(2,5-difluorophenyl)-4-hydroxypyrrolidine-1-PGP-103 C₃ carboxylate (3.00 g, 10.02 mmol, 1.00 eq) and Et₃N (2.03 g, 20.04 mmol, 2.00 eq) in DCM (80.00 mL) was added MsCl (1.61 g, 14.03 mmol, 1.40 eq) dropwise at 0° C. The mixture was stirred at 18° C. for 2 hrs. The mixture was quenched by H₂O (30 mL). The aqueous phase was extracted by DCM (50 mL*3). The combined organic layer was dried over Na₂SO₄ and concentrated under reduced pressure. tert-Butyl (2R,4R)-2-(2,5-difluorophenyl)-4-((methylsulfonyl)oxy)pyrrolidine-1-carboxylate (3.60 g, 9.54 mmol, yield: 95.20%) was obtained as a brown solid.

Step 5: tert-butyl (2R,4S)-4-cyano-2-(2,5-difluorophenyl)pyrrolidine-1-carboxylate

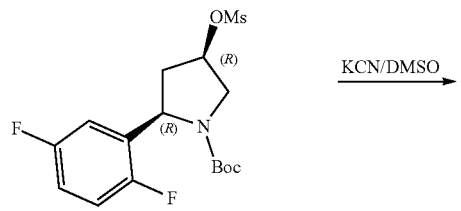

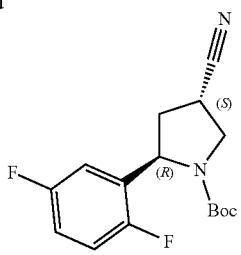

To a mixture of tert-Butyl (2R,4R)-2-(2,5-difluorophenyl)-4-((methylsulfonyl)oxy)pyrrolidine-1-carboxylate (3.60 g, 9.54 mmol, 1.00 eq) in DMSO (20.00 mL) was added KCN (745.49 mg, 11.45 mmol, 1.20 eq) in one portion. The mixture was stirred at 90° C. for 3 hrs. 80 mL of H₂O was added to the mixture, and the mixture was extracted by EtOAc (80 mL*4). The combined organic layer was concentrated under reduced pressure. The residue was purified by silica gel chromatography (PE/EtOAc=40:1, 30:1, 10:1). tert-Butyl (2R,4S)-4-cyano-2-(2,5-difluorophenyl)pyrrolidine-1-carboxylate (1.60 g, 5.19 mmol, yield: 54.40%) was obtained as light green liquid.

Step 6: (3S,5R)-5-(2,5-difluorophenyl)pyrrolidine-3-carbonitrile

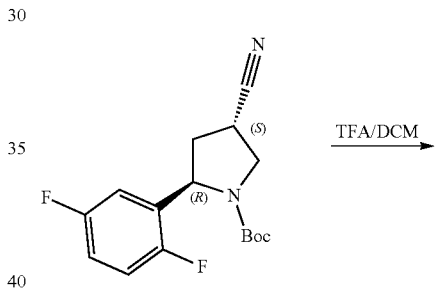

A mixture of tert-Butyl (2R,4S)-4-cyano-2-(2,5-difluorophenyl)pyrrolidine-1-carboxylate (800.00 mg, 2.59 mmol, 1.00 eq) in TFA (4.00 mL)/DCM (20.00 mL) was stirred at 18° C. for 3 hrs. The mixture was dried under N₂. (3S,5R)-5-(2,5-difluorophenyl)pyrrolidine-3-carbonitrile (780.00 mg, 2.42 mmol, yield: 93.44%) was obtained as a light yellow solid.

3-fluoro-5-((2R,4S)-4-fluoropyrrolidin-2-yl)benzamide
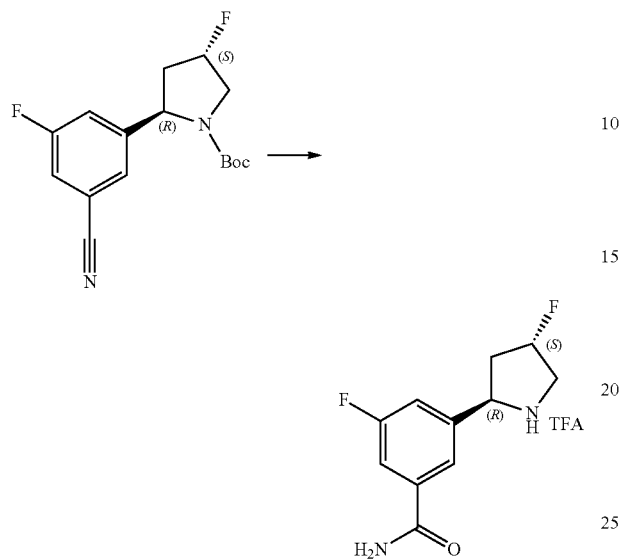
3-Fluoro-5-((2R,4S)-4-fluoropyrrolidin-2-yl)benzonitrile (0.050 g, 0.240 mmol) (Prepared as in WO 2012/034095) was taken up in TFA (0.800 ml, 10.38 mmol) and H₂SO₄ (0.200 ml, 3.75 mmol) and stirred overnight at room temperature. The reaction mixture was diluted with ice water (3 ml) and the solid was isolated by filtration, and used directly.
2-chloro-5-fluoro-3-((2R,4S)-4-fluoropyrrolidin-2-yl)pyridine
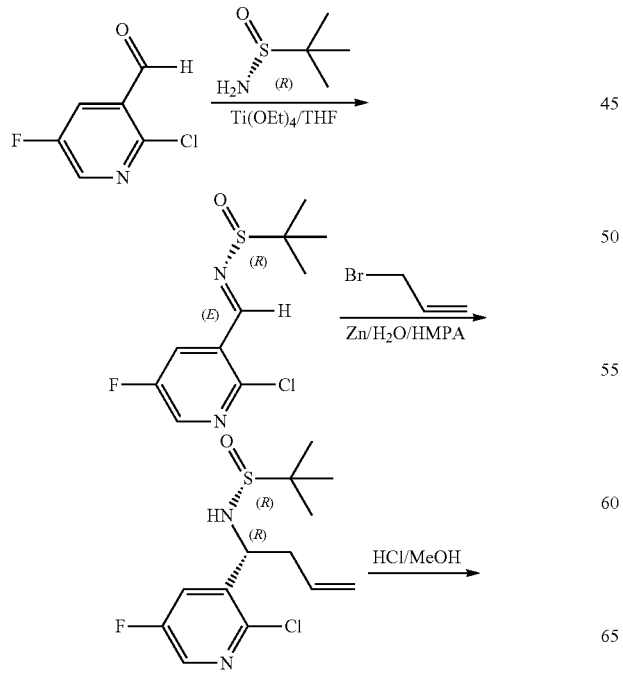
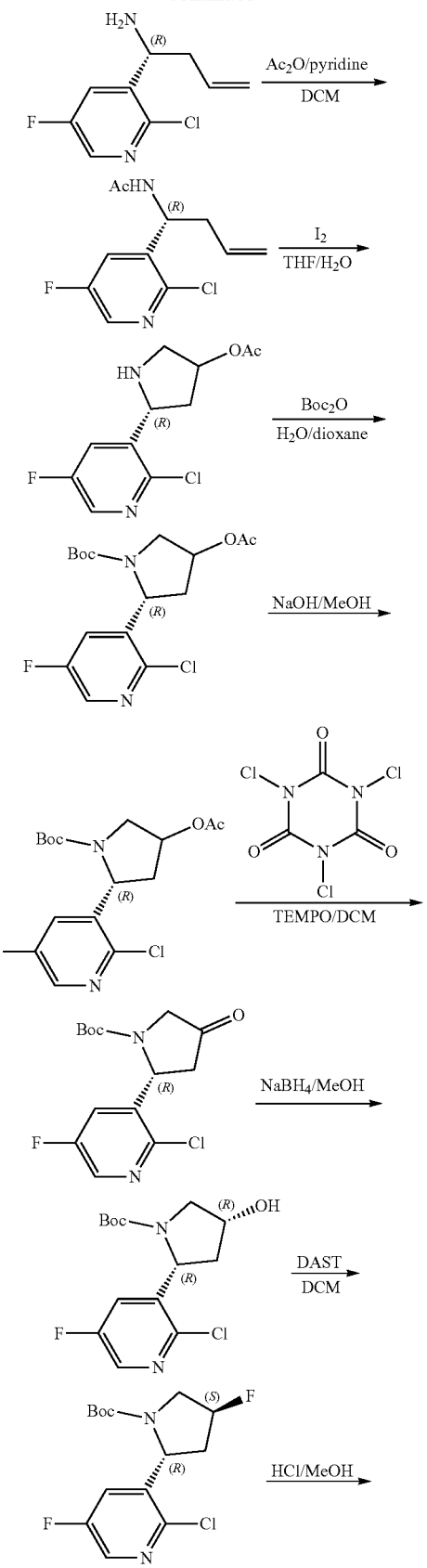

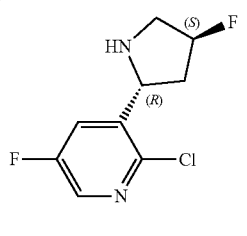

Step 1: (S,Z)—N-((2-chloro-5-fluoropyridin-3-yl)methylene)-2-methylpropane-2-sulfinamide

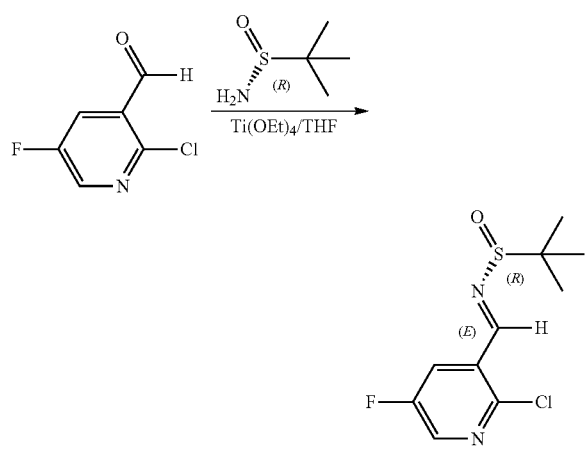

2-chloro-5-fluoronicotinaldehyde (20 g, 125 mmol) was taken up in THF (150 ml) at 0° C. (R)-2-Methylpropane-2-sulfinamide (16.71 g, 138 mmol) was added followed by dropwise addition of titaniumtetraethanolate (22.88 ml, 150 mmol). The reaction mixture was stirred while warming to RT. After 3 hours the reaction mixture was cooled to 0° C., and 150 ml of brine was added and stirred for 20 minutes. The mixture was filtered through Celite. The aqueous layer was separated and discarded. The organic layer with dried over Na$_2$SO$_4$ and the solvent was removed to give (S,Z)—N-((2-chloro-5-fluoropyridin-3-yl)methylene)-2-methylpropane-2-sulfinamide (32 g, 122 mmol, 97% yield), which was carried on without further purification. LCMS: 263 M+H.

Step 2: (R)—N—((R)-1-(2-chloro-5-fluoropyridin-3-yl)but-3-en-1-yl)-2-methylpropane-2-sulfinamide

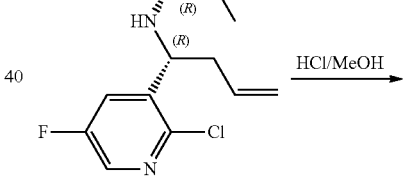

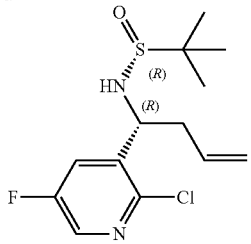

(R,E)-N-((2-chloro-5-fluoropyridin-3-yl)methylene)-2-methylpropane-2-sulfinamide (32.9 g, 125 mmol) was dissolved in HMPA (100 ml) and cooled to 0° C. Zinc (16.37 g, 250 mmol), allyl bromide (21.67 ml, 250 mmol) and water (2.256 ml, 125 mmol) were added at 0° C. and the reaction mixture was allowed to warm to RT overnight. LCMS showed complete conversion to desired product. 100 ml of water was added at RT and stirred for 30 minutes. 30 ml of MBTE was added followed by 60 ml of 10% citric acid and the reaction mixture was stirred for 30 minutes. The mixture was filtered through Celite and washed with MTBE. The organic layer was washed with 10% citric acid, water and brine. The solvent was removed under vacuum to give (R)—N—((R)-1-(2-chloro-5-fluoropyridin-3-yl)but-3-en-1-yl)-2-methylpropane-2-sulfinamide (14.5 g, 47.6 mmol, 38.0% yield) as an orange oil. LCMS: 305 M+H.

Step 3: (R)-1-(2-chloro-5-fluoropyridin-3-yl)but-3-en-1-amine, HCl

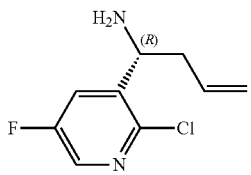

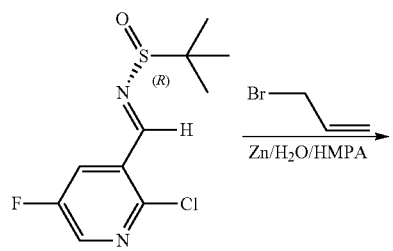

(R)—N—((R)-1-(2-chloro-5-fluoropyridin-3-yl)but-3-en-1-yl)-2-methylpropane-2-sulfinamide (7.5 g, 24.61 mmol) was taken up in 10 ml MeOH. HCl (4M in dioxane) (30.8 ml, 123 mmol) was added and stirred at RT for 1 h. The solvent was removed under vacuum and the residue was diluted in DCM and washed with saturated aqueous NaHCO$_3$. The layers were separated and the organic layer was dried with Na$_2$SO$_4$ and the solvent was removed under vacuum. Recovered (R)-1-(2-chloro-5-fluoropyridin-3-yl)but-3-en-1-amine, HCl (5.83 g, 24.59 mmol, 100% yield) as a solid. LCMS: 201 M+H.

Step 4: (R)—N-(1-(2-chloro-5-fluoropyridin-3-yl)but-3-en-1-yl)acetamide

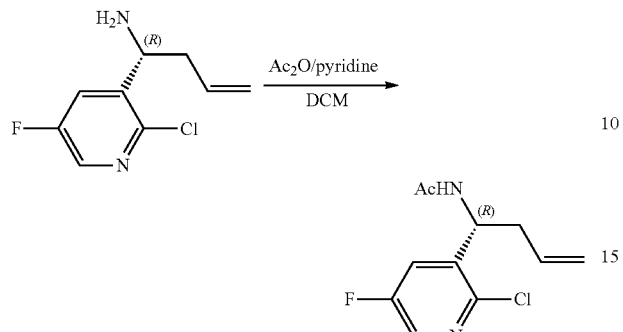

To (R)-1-(2-chloro-5-fluoropyridin-3-yl)but-3-en-1-amine. HCl (5.83 g, 24.59 mmol) in DCM (70.3 ml) at 0° C. was added TEA (4.11 ml, 29.5 mmol) and acetic anhydride (2.320 ml, 24.59 mmol). The mixture was stirred for 2 hours. The reaction mixture was poured into saturated aqueous NaHCO₃ and extracted with DCM. The organic layer was washed with brine, dried over MgSO₄, and evaporated under reduced pressure. Recovered (R)—N-(1-(2-chloro-5-fluoropyridin-3-yl)but-3-en-1-yl)acetamide (5.97 g, 24.60 mmol, 100% yield) and was carried on without further purification. LCMS: 243 M+H.

Step 5: (5R)-5-(2-chloro-5-fluoropyridin-3-yl)pyrrolidin-3-yl acetate

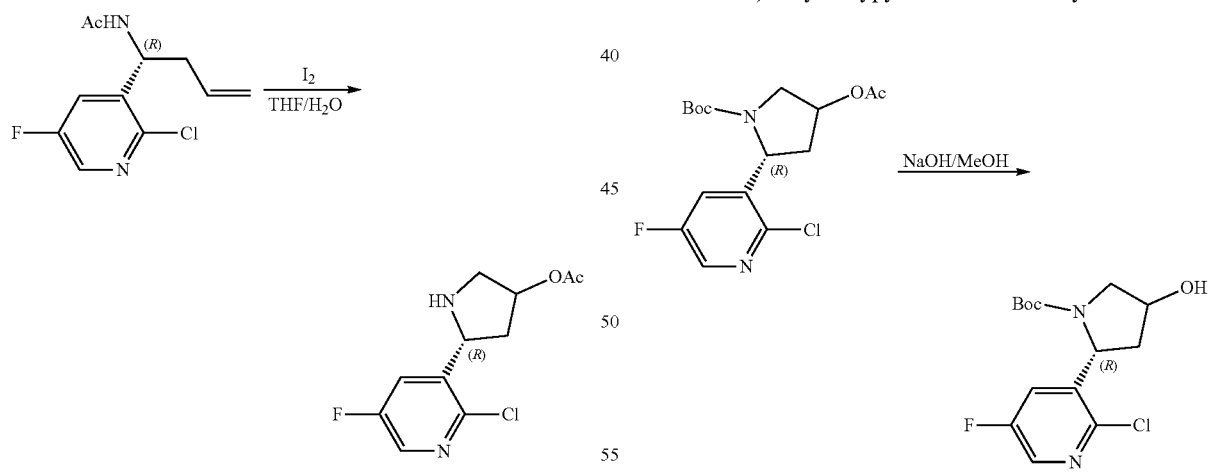

(R)—N-(1-(2-chloro-5-fluoropyridin-3-yl)but-3-en-1-yl)acetamide (5.97 g, 24.60 mmol) was taken up in THF (56.2 ml) and water (14.06 ml), followed by addition of I₂ (18.73 g, 73.8 mmol) and stirred overnight at RT. The crude reaction was diluted with saturated NaHCO₃ and Na₂S₂O₃ solutions and extracted twice with EtOAc. Aqueous layer was basified with saturated aqueous NaHCO₃ and extracted with EtOAc to obtain (5R)-5-(2-chloro-5-fluoropyridin-3-yl)pyrrolidin-3-yl acetate (5.9 g, 22.81 mmol, 93% yield) as a light yellow oil. LCMS: 259 M+H.

Step 6: (2R)-tert-butyl 4-acetoxy-2-(2-chloro-5-fluoropyridin-3-yl)pyrrolidine-1-carboxylate To a solution of (5R)-5-(2-chloro-5-fluoropyridin-3-yl)pyrrolidin-3-yl acetate (5.9 g, 22.81 mmol) in dioxane (76 ml) and water (76 ml) was added BOC-anhydride (7.94 ml, 34.2 mmol) followed by careful addition of 2N NaOH (7 ml) to achieve pH ~9. The reaction mixture was stirred for 1 hour at RT. The reaction mixture was diluted with water and extracted with EtOAc three times. The organic layer was dried over Na₂SO₄ and the solvent was removed under vacuum to give (2R)-tert-butyl 4-acetoxy-2-(2-chloro-5-fluoropyridin-3-yl)pyrrolidine-1-carboxylate (3.5 g, 9.75 mmol, 42.8% yield), which was carried on without further purification. LCMS: 359 M+H.

Step 7: (2R)-tert-butyl 2-(2-chloro-5-fluoropyridin-3-v)-4-hydroxypyrrolidine-1-carboxylate (2R)-tert-butyl 4-acetoxy-2-(2-chloro-5-fluoropyridin-3-yl)pyrrolidine-1-carboxylate (3.5 g, 9.75 mmol) was taken up in MeOH (48.8 ml) followed by addition of 2M NaOH (5.37 ml, 10.73 mmol) and the reaction mixture was stirred at RT for 2 hours. The solvent was removed under vacuum and the aqueous layer was neutralized with 1N HCl, and extracted with EtOAc three times. The combined organic layers were dried over Na₂SO₄. The solvent was removed under vacuum and the residue was purified via silica gel chromatography (0-70% Hex/EtOAc) to give (2R)-tert-butyl 2-(2-chloro-5-fluoropyridin-3-yl)-4-hydroxypyrrolidine-1-carboxylate (2.1 g, 6.63 mmol, 68.0% yield). LCMS: 317 M+H.

Step 8: (R)-tert-butyl 2-(2-chloro-5-fluoropyridin-3-yl)-4-oxopyrrolidine-1-carboxylate

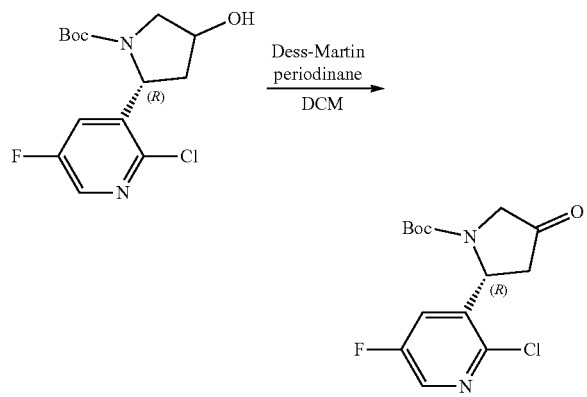

(2R)-tert-butyl 2-(2-chloro-5-fluoropyridin-3-yl)-4-hydroxypyrrolidine-1-carboxylate (2.1 g, 6.63 mmol) was taken up in DCM (66.3 ml) and NaHCO$_3$ (0.557 g, 6.63 mmol) was added followed by Dess-Martin periodinane (8.44 g, 19.89 mmol). The reaction mixture was stirred overnight. Water was added (0.119 ml, 6.63 mmol) followed by Dess-Martin periodinane (8.44 g, 19.89 mmol) and stirred for 18 hours. The pH was adjusted to ~7 with saturated aqueous NaHCO$_3$ and extracted with DCM×3. The organic layers were combined, dried over Na$_2$SO$_4$ and the solvent was removed under vacuum. The residue was purified via flash chromatography (0-70% Hex/EtOAc) to give (R)-tert-butyl 2-(2-chloro-5-fluoropyridin-3-yl)-4-oxopyrrolidine-1-carboxylate (1.6 g, 5.08 mmol, 77% yield). LCMS: 315 M+H.

Step 9: (2R,4R)-tert-butyl 2-(2-chloro-5-fluoropyridin-3-yl)-4-hydroxypyrrolidine-1-carboxylate

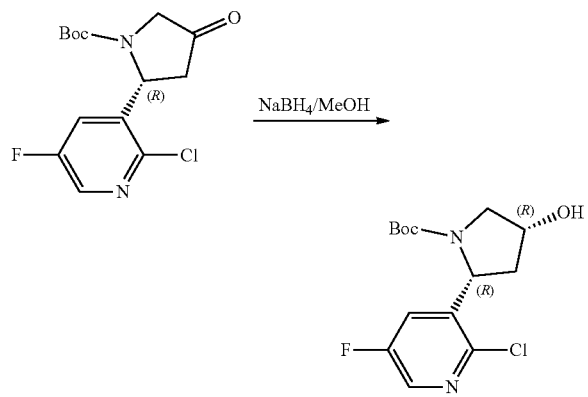

(R)-tert-butyl 2-(2-chloro-5-fluoropyridin-3-yl)-4-oxopyrrolidine-1-carboxylate (1.6 g, 5.08 mmol) was suspended in ethanol (33.9 ml) and cooled to 0° C. NaBH$_4$ was added portionwise (0.096 g, 2.54 mmol) and stirred for 45 minutes at 0° C. The reaction was quenched slowly with saturated NH$_4$Cl and allowed to warm to RT, and the solution was extracted with DCM×3. The organic layers were combined and dried over Na$_2$SO$_4$. The residue was purified via flash chromatography (0-70% Hex/EtOAc) to give (2R,4R)-tert-butyl 2-(2-chloro-5-fluoropyridin-3-yl)-4-hydroxypyrrolidine-1-carboxylate (1.446 g, 4.57 mmol, 90% yield). LCMS: 317 M+H.

Step 10: (2R,4S)-tert-butyl 2-(2-chloro-5-fluoropyridin-3-yl)-4-fluoropyrrolidine-1-carboxylate

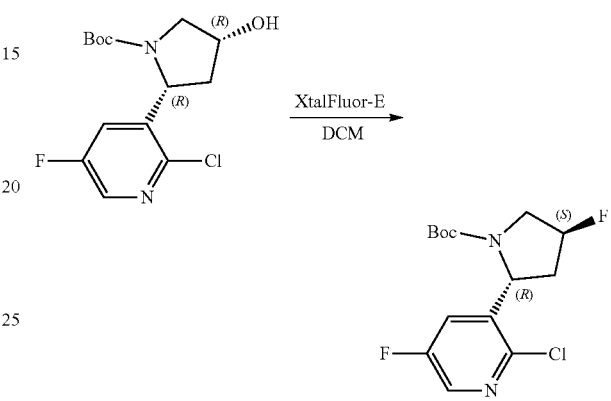

(2R,4R)-tert-butyl 2-(2-chloro-5-fluoropyridin-3-yl)-4-hydroxypyrrolidine-1-carboxylate (1.0 g, 3.16 mmol) was taken up in DCM (25 ml) and cooled to −78° C. TEA-HF (1.098 ml, 9.47 mmol) was added and stirred for 10 minutes. XtalFluor-E (1.446 g, 6.31 mmol) was added and after 10 minutes the reaction mixture was transferred to an ice bath and allowed to warm to 0° C. After 2 hours the reaction mixture was diluted with DCM and quenched with saturated aqueous NaHCO$_3$. The organic layers were separated, and the solvent was removed under vacuum. The residue was purified via ISCO (0-50% Hex/EtOAc; 12 g column) to give (2R,4S)-tert-butyl 2-(2-chloro-5-fluoropyridin-3-yl)-4-fluoropyrrolidine-1-carboxylate (0.805 g, 2.53 mmol, 80% yield) as a white solid. LCMS: 319 M+H.

Step 11: 2-chloro-5-fluoro-3-((2R,4S)-4-fluoropyrrolidin-2-yl)pyridine, HCl

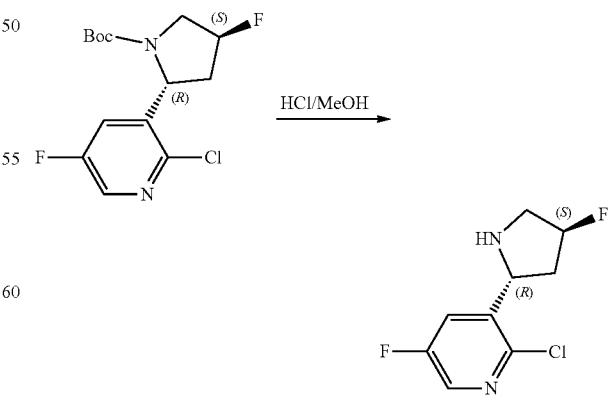

(2R,4S)-tert-butyl 2-(2-chloro-5-fluoropyridin-3-yl)-4-fluoropyrrolidine-1-carboxylate (0.805 g, 2.53 mmol, 80% yield) was taken up in EtOAc (5 ml) and 4N HCl/dioxane (3 ml) was added. The reaction mixture was stirred at RT for 1 hour. The precipitate was filtered off, washed with ether, and dried under high vacuum overnight to give 2-chloro-5-fluoro-3-((2R,4S)-4-fluoropyrrolidin-2-yl)pyridine, HCl (0.612 g, 2.399 mmol, 76% yield) as an off white solid. LCMS: 219 M+H. 5-fluoro-3-((2R,4S)-4-fluoropyrrolidin-2-yl)-2-methoxypyridine

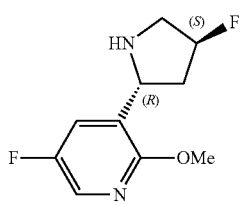

5-Fluoro-3-((2R,4S)-4-fluoropyrrolidin-2-yl)-2-methoxypyridine was prepared in the same way as 3-fluoro-5-((2R,4S)-4-fluoropyrrolidin-2-yl)benzamide, substituting for 5-fluoro-2-methoxynicotinaldehyde for 2-chloro-5-fluoronicotinaldehyde.

3-fluoro-5-((2R,4S)-4-fluoropyrrolidin-2-yl)benzenesulfonamide

Step 1: (2R,4S)-2-(3-(benzylthio)-5-fluorophenyl)-1-(tert-butylsulfonyl)-4-fluoropyrrolidine

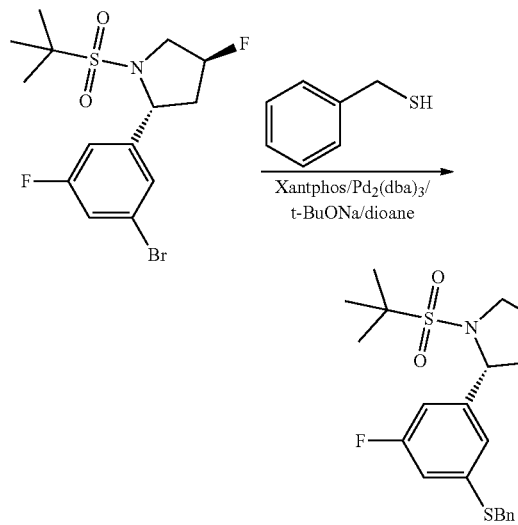

To a mixture of (2R,4S)-2-(3-bromo-5-fluorophenyl)-1-(tert-butylsulfonyl)-4-fluoropyrrolidine (1.00 g, 2.62 mmol, 1.00 eq) in dioxane (3.00 mL) was added t-BuONa (502.80 mg, 5.23 mmol, 2.00 eq), phenylmethanethiol (649.82 mg, 5.23 mmol, 613.04 uL, 2.00 eq), Xantphos (151.37 mg, 261.60 umol, 0.10 eq) and Pd₂(dba)₃ (239.55 mg, 261.60 umol, 0.10 eq). After addition, the mixture was stirred at 80° C. for 16 hrs under N₂. The mixture was concentrated to give the crude product. The mixture was purified by column chromatography on silica gel (PE:EtOAc=20:1-8:1) to give (2R,4S)-2-(3-(benzylthio)-5-fluorophenyl)-1-(tert-butylsulfonyl)-4-fluoropyrrolidine (700.00 mg, 1.64 mmol, yield: 62.78%) as a red oil.

Step 2: 3-((2R,4S)-1-(tert-butylsulfonyl)-4-fluoropyrrolidin-2-yl)-5-fluorobenzenesulfonamide

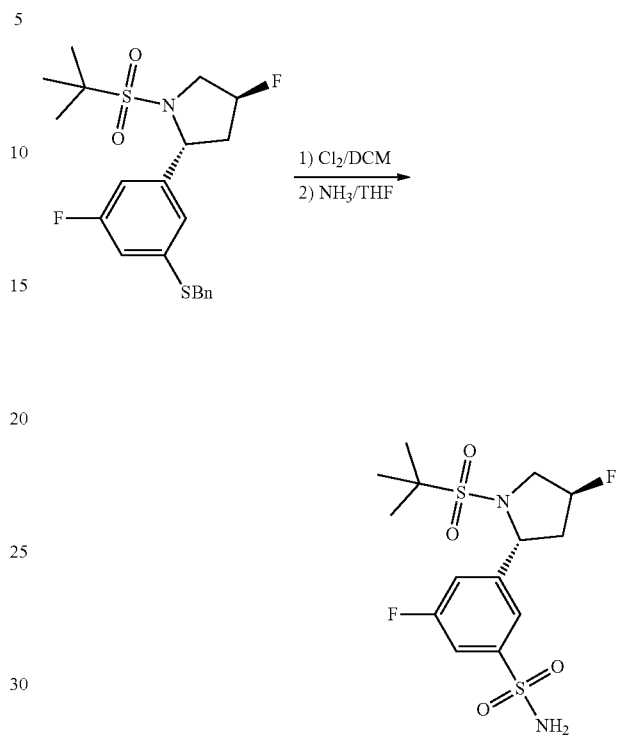

A steady stream of Cl₂ gas was bubbled through a mixture of (2R,4S)-2-(3-(benzylthio)-5-fluorophenyl)-1-(tert-butylsulfonyl)-4-fluoropyrrolidine (700.00 mg, 1.64 mmol, 1.00 eq) in DCM (16.00 mL)/AcOH (8.00 mL)/H₂O (4.00 mL) at 0° C. for 6 mins. The reaction mixture was dissipated by sparging with N₂ gas for 6 mins. The resulting bis-sulfonyl chloride was then treated with excess NH₃H₂O until the pH of the aqueous phase was 9-10 and warmed to 25° C. and stirred for 16 hrs. LCMS showed the reaction was complete. The mixture was extracted with DCM (20 mL*3), the organic layer was concentrated to give 3-((2R,4S)-1-(tert-butylsulfonyl)-4-fluoropyrrolidin-2-yl)-5-fluorobenzenesulfonamide (600.00 mg, crude) as a yellow oil.

Step 3: 3-fluoro-5-((2R,4S)-4-fluoropyrrolidin-2-yl)benzenesulfonamide

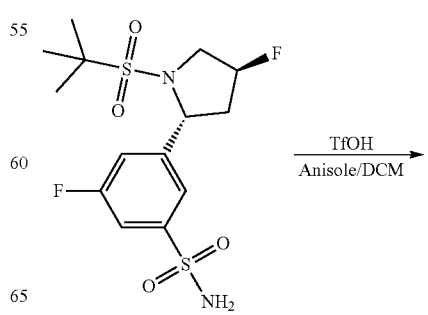

-continued

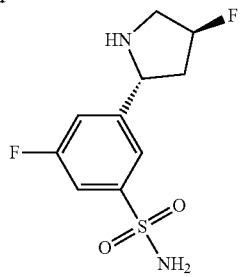

To a mixture of TfOH (706.35 mg, 4.71 mmol, 415.50 uL, 3.00 eq) in DCM (20.00 mL) was added anisole (254.48 mg, 2.36 mmol, 254.48 uL, 1.50 eq) at −40° C., then a solution of 3-((2R,4S)-1-(tert-butylsulfonyl)-4-fluoropyrrolidin-2-yl)-5-fluorobenzenesulfonamide (600.00 mg, 1.57 mmol, 1.00 eq) in DCM (10.00 mL) was added drop wise to the mixture at −40° C. over 0.1 hr. After addition, the mixture was warmed to 25° C. and stirred at 25° C. for 1 hr. TLC (PE:EtOAc=1:1) showed the starting material was consumed complete. The mixture was added to saturated aq. $K_2CO_3$ (100 mL) and stirred for 0.1 hr. The mixture was extracted with DCM (100 mL*2). The water layer was concentrated to give the crude product. The mixture was washed with DCM (10 mL*3), the organic layer was concentrated to give 3-fluoro-5-((2R,4S)-4-fluoropyrrolidin-2-yl) benzenesulfonamide (300.00 mg, crude) as a yellow oil.

The NMR and LC MS data obtained for compounds disclosed herein are also shown below.

| Compound Number | $^1$H NMR | MS (M + 1) |
|---|---|---|
| 1 | $^1$H-NMR (400 MHz, CD$_3$OD) δ ppm 8.55 (br.s, 1H), 8.44 (d, 1H, J = 2.4 Hz), 8.10 (s, 1H), 7.83 (br.s, 1H), 6.69 (br.s, 1H), 6.24 (br.s, 1H), 5.55-5.43 (m, 2H), 4.25-4.16 (m, 2H), 2.95 (br.s, 1H), 2.40-2.26 (m, 1H) | 327 |
| 2 | $^1$H NMR (400 MHz, DMSO-d6) δ 8.76 (d, J = 48.6 Hz, 1H), 8.33 (d, J = 37.6 Hz, 1H), 7.16 (d, J = 50.9 Hz, 3H), 6.47 (d, J = 238.1 Hz, 1H), 5.74-5.24 (m, 2H), 4.26 (d, J = 123.1 Hz, 2H), 2.80 (s, 1H), 2.27 (d, J = 40.7 Hz, 1H) | 344 |
| 3 | $^1$H-NMR (400 MHz, CD$_3$OD) δ ppm 8.57-8.53 (m, 3H), 8.12 (br.s, 1H), 7.91 (s, 1H), 6.56 (br.s, 1H), 5.70 (br.s, 1H), 4.46-4.41 (m, 1H), 4.38-4.24 (m, 1H), 3.25-3.11 (m, 1H), 2.69-2.58 (m, 1H) | 345 |
| 4 | $^1$H-NMR (400 MHz, CD$_3$OD) δ ppm 8.84 (d, 1H, J = 7.6 Hz), 8.66 (s, 1H), 8.49 (s, 1H), 8.11 (s, 1H), 8.00 (br.s, 1H), 5.60-5.57 (m, 1H), 5.49 (d, 1H, J = 52.4 Hz), 4.49-4.30 (m, 2H), 2.93-2.84 (m, 1H), 2.36-2.22 (m, 1H) | 345 |
| 5 | $^1$H-NMR (400 MHz, CDCl$_3$) δ ppm 8.29 (br.s, 1H), 8.10 (s, 1H), 7.14-7.12 (m, 1H), 7.02 (br.s, 1.5H), 6.73 (br.s, 1.5H), 4.32 (br.s, 2H), 3.35 (br.s, 1H), 2.89 (br.s, 1.0H), 2.53 (br.s, 2H) | 350 |
| 6 | $^1$H-NMR (400 MHz, DMSO-d6) δ ppm 8.74 (d, J = 63.8 Hz, 1H), 8.33 (d, J = 36.7 Hz, 1H), 7.73 (d, J = 39.9 Hz, 2H), 6.46 (d, J = 249.9 Hz, 1H), 5.50 (d, J = 56.3 Hz, 1H), 5.34 (t, 1H), 4.54-4.04 (m, 3H), 2.98-2.66 (m, 1H), 2.21 (d, J = 42.5 Hz, 1H) | 351 |
| 7 | $^1$H NMR (400 MHz, DMSO-d6) δ ppm 8.73 (dd, J = 59.6, 7.8 Hz, 1H), 8.32 (d, J = 41.5 Hz, 1H), 8.05 (d, J = 42.4 Hz, 1H), 7.65 (m, 1H), 6.76-6.13 (m, 1H), 5.64-5.24 (m, 2H), 4.42-4.15 (m, 2H), 3.92 (s, 3H), 2.94-2.65 (m, 1H), 2.25 (dt, J = 40.8, 10.7 Hz, 1H) | 357 |
| 8 | $^1$H NMR (400 MHz, DMSO-d6) δ ppm 8.73 (dd, J = 36.6, 7.7 Hz, 1H), 8.32 (d, J = 30.5 Hz, 1H), 7.90 (d, J = 38.4 Hz, 1H), 7.72-7.50 (m, 1H), 6.73-6.25 (m, 1H), 5.50 (dd, J = 53.0, 21.0 Hz, 1H), 5.36-5.12 (m, 1H), 4.37 (dd, J = 21.7, 13.8 Hz, 1H), 4.21-3.95 (m, 1H), 3.41 (d, 3H), 2.86-2.54 (m, 1H), 2.29 (m, 1H) | 357 |
| 9 | $^1$H NMR (400 MHz, Methanol-d4) δ 8.45 (s, 1H), 8.14 (s, 1H), 7.25 (d, J = 1.6 Hz, 1H), 7.09 (dt, J = 9.3, 1.9 Hz, 1H), 6.79-6.51 (m, 1H), 6.19 (s, 1H), 5.57-5.17 (m, 2H), 4.14 (d, J = 36.3 Hz, 2H), 2.92 (s, 1H), 2.24 (dddd, J = 40.9, 14.6, 9.4, 3.7 Hz, 1H) | 360 |
| 10 | $^1$H NMR (400 MHz, Methanol-d4) δ 8.57 (s, 1H), 8.26-8.04 (m, 2H), 7.61 (dd, J = 8.9, 2.8 Hz, 1H), 6.71 (d, J = 7.5 Hz, 1H), 5.68-5.36 (m, 2H), 4.20 (d, J = 36.4 Hz, 2H), 2.38-2.14 (m, 2H) | 361 |
| 11 | $^1$H NMR (400 MHz, Methanol-d4) δ 8.42 (s, 1H), 8.13 (s, 1H), 7.69 (t, J = 1.7 Hz, 1H), 7.51 (s, 1H), 7.34 (dt, J = 9.2, 2.0 Hz, 1H), 6.69 (s, 1H), 6.20 (s, 1H), 5.51 (d, J = 13.9 Hz, 1H), 5.40 (s, 1H), 4.18 (d, J = 36.7 Hz, 1H), 2.95 (s, 1H), 2.27 (dddd, J = 40.8, 13.9, 9.3, 3.7 Hz, 1H) | 369 |
| 12 | $^1$H-NMR (400 MHz, CD$_3$OD) δ ppm 8.81 (d, 1H, J = 7.2 Hz), 8.12 (s, 1H), 7.66 (s, 1H), 7.54 (d, 1H, J = 9.2 Hz), 7.40 (d, 1H, J = 7.6 Hz), 5.52-5.39 (m, 2H), 4.47-4.29 (m, 2H), 2.91-2.81 (m, 1H), 2.29-2.12 (m, 1H) | 369 |
| 13 | $^1$H-NMR (400 MHz, CD$_3$OD) δ ppm 8.54-8.43 (m, 1H), 8.10 (br.s, 1H), 6.96-6.77 (m, 3H), 5.51-5.38 (m, 2H), 4.05 (br.s, 5H), 2.83 (br.s, 1H), 2.20-2.03 (m, 1H) | 374 |

| Compound Number | ¹H NMR | MS (M + 1) |
|---|---|---|
| 14 | ¹H-NMR (400 MHz, CD$_3$OD) δ ppm 8.35 (br.s, 1H), 8.11 (s, 1H), 7.28 (s, 1H), 7.10 (d, 1H, J = 8.0 Hz), 6.91 (d, 1H, J = 8.8 Hz), 6.17 (br.s, 1H), 5.42 (d, 1H, J = 52.4 Hz), 5.23 (br.s, 1H), 4.16-4.08 (m, 1H), 2.91 (br.s, 1H), 2.31-2.17 (m, 1H), 1.47 (d, 6H, J = 3.6 Hz). | 384 |
| 15 | ¹H-NMR (400 MHz, CD$_3$OD) δ ppm 8.76 (d, 1H, J = 7.2 Hz), 8.09 (s, 1H), 7.69 (s, 1H), 7.44 (d, 1H, J = 9.2 Hz), 7.36 (d, 1H, J = 8.4 Hz), 5.55-5.39 (m, 2H), 4.45-4.33 (m, 2H), 2.90-2.81 (m, 1H), 2.30-2.16 (m, 1H) | 387 |
| 16 | ¹H-NMR (400 MHz, CDCl$_3$) δ ppm 8.34 (br.s, 1H), 7.98 (s, 2H), 7.92 (d, 1H, J = 6.8 Hz), 7.02 (d, 1H, J = 6.4 Hz), 6.39 (br.s, 1H), 5.55-5.36 (m, 4H), 4.20-4.03 (m, 2H), 2.93 (br.s, 1H), 2.29-2.15 (m, 1H). | 405 |
| 17 | ¹H-NMR (400 MHz, CD$_3$OD) δ ppm 8.49 (br.s, 1H), 8.08 (br.s, 1H), 7.36 (s, 1H), 7.08 (d, 2H, J = 8.4 Hz), 6.67 (br.s, 1H), 5.52 (br.s, 2H), 5.46 (d, 1H, J = 52.0 Hz), 4.17 (br.s, 1H), 4.09 (br.s, 1H), 4.87 (br.s, 1H), 2.32-2.16 (m, 1H) | 410 |
| 18 | ¹H-NMR (400 MHz, CD$_3$OD) δ ppm 8.37 (br.s, 1H), 8.10 (br.s, 1H), 7.66 (s, 1H), 7.46 (br.s, 1H), 7.30 (br.s, 1H), 6.66 (br.s, 0.5H), 6.17 (br.s, 0.5H), 5.51-5.38 (m, 2H), 4.53 (br.s, 1H), 4.20-4.13 (m, 1H), 3.68-3.65 (m, 2H), 3.46-3.45 (m, 2H), 2.98-2.92 (m, 1H), 2.31-2.22 (m, 1H). | 413 |
| 19 | ¹H-NMR (400 MHz, CD$_3$OD) δ ppm 8.39 (br.s, 1H), 8.12 (br.s, 1H), 7.65 (s, 1H), 7.47 (br.s, 1H), 7.32 (d, 1H, J = 8.8 Hz), 6.68 (br.s, 0.5H), 6.19 (br.s, 0.5H), 5.52-5.39 (m, 2H), 4.62 (br.s, 1H), 4.23-4.14 (m, 2H), 3.21 (d, 2H, J = 6.8 Hz), 2.95 (br.s, 1H), 2.36-2.20 (m, 1H), 1.10-1.07 (m, 1H), 0.50 (d, 2H, J = 8.0 Hz), 0.26 (d, 2H, J = 4.4 Hz). | 423 |
| 20 | ¹H-NMR (400 MHz, CD$_3$OD) δ ppm 8.38 (br.s, 1H), 8.11 (br.s, 1H), 7.62 (s, 1H), 7.43 (br.s, 1H), 7.31 (d, 1H, J = 9.2 Hz), 6.67-6.62 (m, 0.5H), 6.18 (br.s, 0.5H), 5.45 (d, 1H, J = 52.8 Hz), 5.38 (br.s, 1H), 4.60 (br.s, 1H), 4.21-4.13 (m, 1H), 3.36 (br.s, 1H), 2.88 (s, 3H), 2.34-2.18 (m, 1H). | 383.1 |
| 21 | ¹H-NMR (400 MHz, CD$_3$OD) δ ppm 8.41 (br.s, 1H), 8.09 (br.s, 1H), 7.20 (s, 2H), 7.05 (br.s, 1H), 6.66 (br.s, 0.5H), 6.18 (br.s, 0.5H), 5.43 (d, 1H, J = 52.4 Hz), 5.36 (br.s, 1H), 4.54 (br.s, 0.5H), 4.19-4.05 (m, 1.5H), 3.08-2.88 (m, 7H), 2.32-2.18 (m, 1H). | 397.1 |
| 22 | ¹H-NMR (400 MHz, CD$_3$OD) δ ppm 8.51-8.33 (m, 1H), 8.13-8.04 (m, 1H), 7.55 (br.s, 1H), 7.09-7.00 (m, 2H), 6.67-6.28 (m, 1H), 5.63-5.59 (m, 1H), 5.44 (d, 1H, J = 52.8 Hz), 4.58-4.27 (m, 1H), 4.16-3.97 (m, 1H), 2.97 (br.s, 1H), 2.41-2.24 (m, 1H). | 369.0 |

NTRK1 Wild Type Assay at 1 mM ATP

In each well of a 384-well plate, 1 nM-1.5 nM of wild type NTRK1 enzyme (BPS Bioscience; 40280) was incubated in a total of 12.5 μL of buffer (100 mM HEPES pH 7.5, 0.015% Brij 35, 10 mM MgCl$_2$, 1 mM DTT) with 1-2 aM CSKtide (Tuft's University or Anaspec; FITC-AHA-KKKKD DIYFFFG-NH2) and 1 mM ATP at 25° C. for 60 minutes in the presence or absence of a dosed concentration series of compound (1% DMSO final concentration). The reaction was stopped by the addition of 70 μL of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: ~1.7 psi, upstream voltage −500, downstream voltage −3000, post sample sip 35 s). Data was normalized to 0% and 100% inhibition controls and the IC$_{50}$ calculated using a 4-parameter fit in the CORE LIMS.

NTRK Wild Type and G595R Mutant Cellular Assays Protocol

KM12 wild type colon carcinoma cell line harboring the TPM3-NTRK1 fusion protein was obtained from the National Cancer Institute (NCI). This line has been previously shown to be dependent upon the NTRK activity derived from the NTRK fusion protein for growth and survival. The KM12 Cliff (G595R) cell line was generated by mutagenizing the wild type KM12 line with a DNA methylating agent and subsequently selecting for clones that were resistant to chronic exposure to high concentration of a known NTRK inhibitor (Crizotinib). Cells were first plated in 384-well plates at 1000 cells/well in complete media (10% FBS and 1% pen/strep) and incubated overnight at 37° C. Cells were then dosed with test articles at varying concentrations using the Bravo liquid handling system. Concentrations ranged from 25 uM down to 9.5 pM (4-fold dilutions, 10 concentrations total). Each compound was run in duplicate per plate. DMSO and staurosporine (25 uM) were included on each plate as negative and positive controls for growth inhibition. 72 hr after dosing, assay plates were developed using CellTiter-Glo (Promega) and resultant luminescence was read on the Envision plate reader. IC$_{50}$ determinations were calculated using a 4-parameter curve fitting algorithm The table below summarizes the results from the biological assays described above. The following designations are used to indicate activity: A<10.00 nM; B=10.01-100.0 nM; C=100.01-1000.0 nM; and D>1000.1 nM.

| Compound Number | NTRK1 IC$_{50}$ (nM) | KM12 IC$_{50}$ (nM) | G595R-KM12 IC$_{50}$ (nM) |
| --- | --- | --- | --- |
| 1 | A | A | B |
| 2 | A | A | A |
| 3 | B | B | C |
| 4 | A | A | A |
| 5 | B | B | C |
| 6 | A | A | A |
| 7 | A | A | A |
| 8 | B | B | C |
| 9 | A | A | A |
| 10 | A | A | A |
| 11 | A | A | B |
| 12 | A | A | A |
| 13 | A | A | A |
| 14 | B | B | C |
| 15 | A | B | B |
| 16 | A | B | B |
| 17 | A | A | A |
| 18 | B | B | B |
| 19 | A | B | B |
| 20 | B | B | B |
| 21 | B | B | C |
| 22 | B | B | C |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein.

Such equivalents are intended to be encompassed by the following claims.

We claim:

1. A method for treating a subject suffering from a tumor by inhibiting neurotrophic tyrosine receptor kinase (NTRK) activity, the method comprising administering to the subject a therapeutically effective amount of a compound of Formula I or a pharmaceutically acceptable salt thereof, wherein:

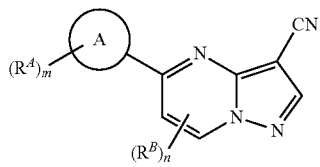

Ring A is cycloalkyl or heterocyclyl;
each $R^A$ is independently selected from monocyclic or bicyclic aryl, monocyclic or bicyclic heteroaryl, monocyclic or bicyclic cycloalkyl, monocyclic or bicyclic heterocyclyl, $C_1$-$C_6$ alkyl, $C_1$-$C_6$ alkoxyl, halo, $C_1$-$C_6$ haloalkyl, $C_1$-$C_6$ haloalkoxyl, $C_1$-$C_6$ hydroxyalkyl, $C_1$-$C_6$ heteroalkyl, —N(R$^1$)(R$^1$), cyano, —C(O)R$^1$, —OC(O)R$^1$, —C(O)OR$^1$, —SR$^1$, —S(O)$_2$R$^1$, —S(O)$_2$—N(R$^2$)(R$^2$), —(C$_1$-C$_6$ alkylene)-S(O)$_2$—N(R$^2$)(R$^2$), —C(O)—N(R$^2$)(R$^2$), —N(R$^2$)—C(O)R$^1$, —(C$_1$-C$_6$ alkylene)-N(R$^2$)—C(O)R$^1$, —NR$^2$S(O)$_2$R$^1$, —P(O)(R$^1$)(R$^1$), and —OR$^1$; wherein
each of aryl, heteroaryl, cycloalkyl, heterocyclyl, $C_1$-$C_6$ alkyl, $C_1$-$C_6$ alkoxyl, $C_1$-$C_6$ haloalkyl, $C_1$-$C_6$ hydroxyalkyl, $C_1$-$C_6$ heteroalkyl is independently substituted with 0-5 occurrences of R$^a$; and
wherein at least one $R^A$ is halo;
each $R^B$ is independently halo;
each $R^1$ is independently selected from hydrogen, $C_1$-$C_6$ alkyl, $C_1$-$C_6$ haloalkyl, $C_1$-$C_6$ haloalkoxyl, $C_1$-$C_6$ hydroxyalkyl, $C_1$-$C_6$ heteroalkyl, cycloalkyl, cycloalkylalkyl, heterocyclyl, and heterocyclylalkyl, wherein each of $C_1$-$C_6$ alkyl, $C_1$-$C_6$ haloalkyl, $C_1$-$C_6$ hydroxyalkyl, $C_1$-$C_6$ heteroalkyl, cycloalkyl, cycloalkylalkyl, heterocyclyl, and heterocyclylalkyl is independently substituted with 0-5 occurrences of R$^b$;
each $R^2$ is independently selected from hydrogen, $C_1$-$C_6$ alkyl, and $C_1$-$C_6$ heteroalkyl; or 2 $R^2$ together with the nitrogen to which they are attached form a heterocyclyl ring substituted with 0-5 occurrences of R$^b$;
each $R^a$ and $R^b$ is independently selected from halo, cyano, hydroxyl, $C_1$-$C_6$ alkyl, $C_1$-$C_6$ alkoxyl, $C_1$-$C_6$ haloalkoxyl, —N(R")(R"), —C(O)—N(R")(R"), —N(R")—C(O)R', and —(C$_1$-C$_6$ alkylene)-N(R")—C(O)R';
each R' and R" is independently selected from hydrogen, $C_1$-$C_6$ alkyl, and $C_1$-$C_6$ hydroxyalkyl;
m is 1, 2, 3, 4 or 5; and
n is 0, 1 or 2.

2. The method of claim 1, wherein the compound is represented by Formula (Ia-1):

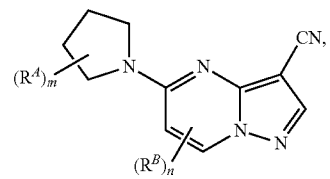

or a pharmaceutically acceptable salt thereof.

3. The method of claim 2, wherein each $R^a$ is independently selected from halo.

4. The method of claim 1, wherein the compound is represented by Formula (Ib):

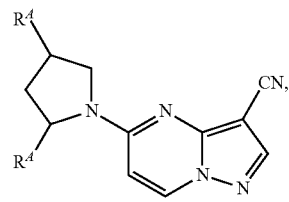

or a pharmaceutically acceptable salt thereof.

5. The method of claim 4, wherein one $R^A$ is halo and one $R^A$ is monocyclic or bicyclic aryl or monocyclic or bicyclic heteroaryl.

6. The method of claim 1, wherein the compound is selected from any one of the compounds in the table below:

| Compound Number | Structure |
|---|---|
| 1 | 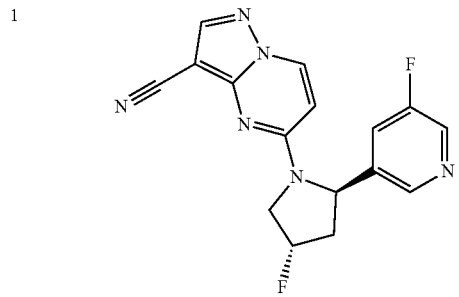 |
| 2 | 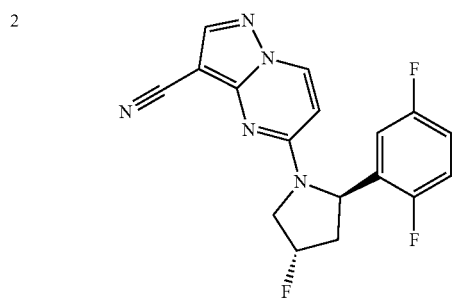 |
| 3 | 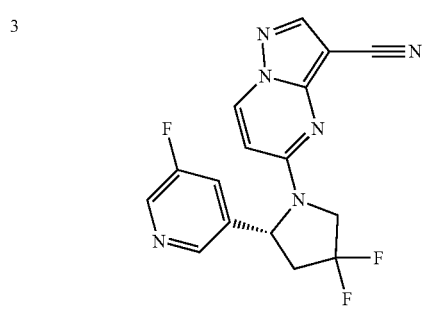 |
| 4 | 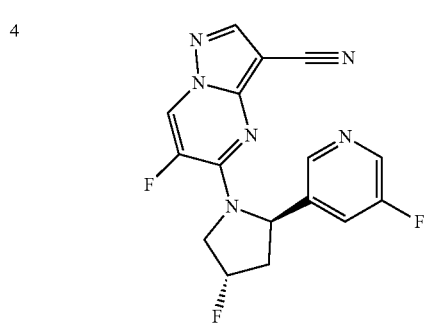 |
| 6 | 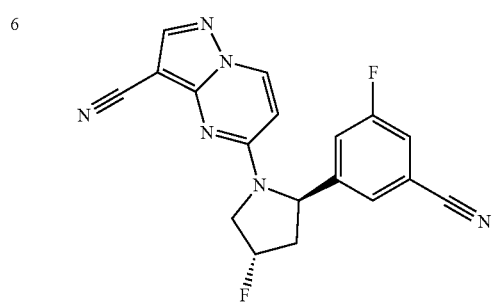 |
-continued
| Compound Number | Structure |
|---|---|
| 7 | 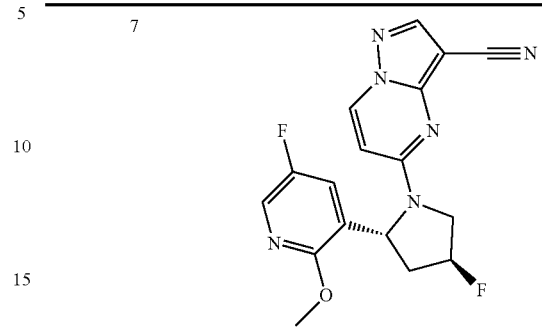 |
| 8 | 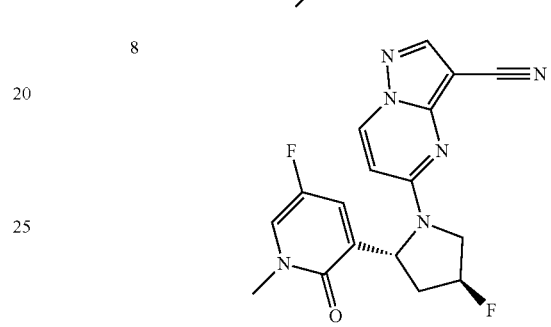 |
| 9 | 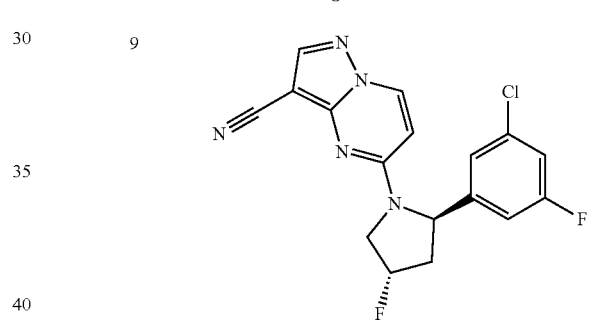 |
| 10 | 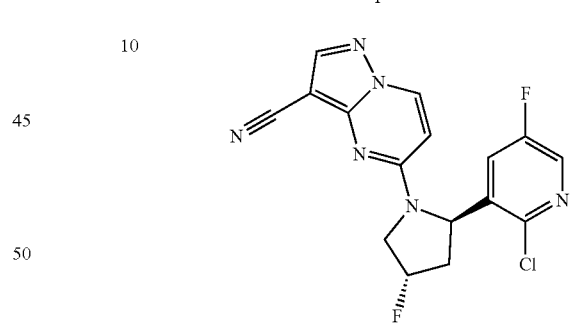 |
| 11 | 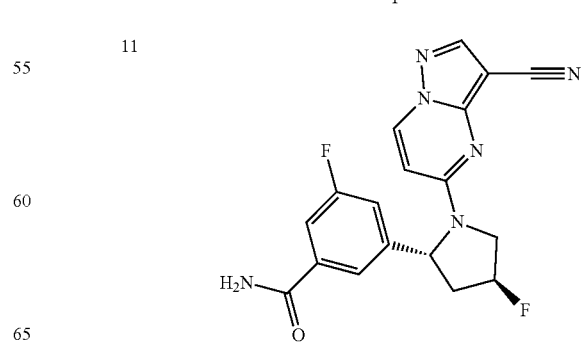 |

-continued

| Compound Number | Structure |
|---|---|
| 12 | 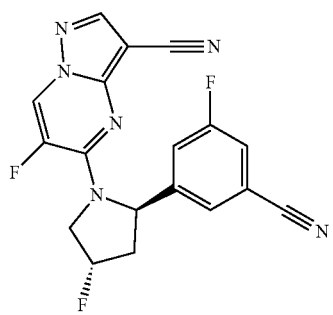 [SMILES: N#Cc1cc(F)cc([C@H]2C[C@H](F)CN2c2nc3c(C#N)cnn3cc2F)c1] |
| 13 | 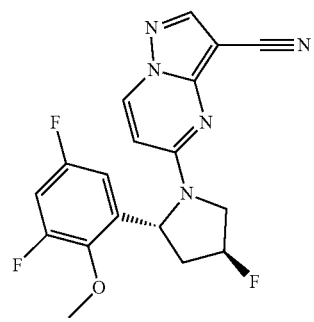 [SMILES: COc1c(F)cc(F)cc1[C@H]1C[C@H](F)CN1c1ccn2ncc(C#N)c2n1] |
| 15 | 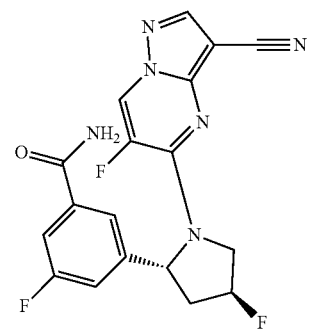 [SMILES: N#Cc1cnn2cc(F)c(CN3C[C@@H](F)C[C@@H]3c3cc(F)cc(C(N)=O)c3)nc12] |
| 17 | 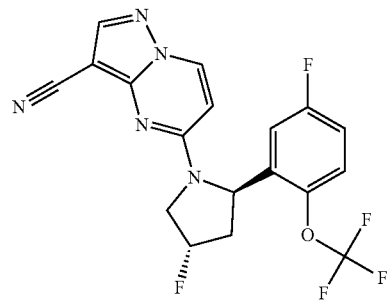 [SMILES: N#Cc1cnn2ccc(N3C[C@@H](F)C[C@@H]3c3cc(F)ccc3OC(F)(F)F)nc12] |

-continued

| Compound Number | Structure |
|---|---|
| 18 | 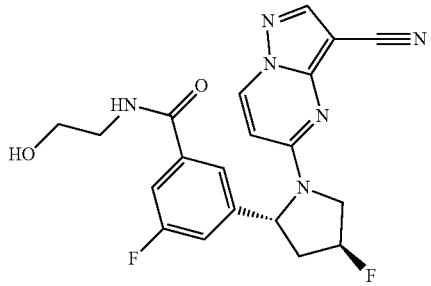 [SMILES: N#Cc1cnn2ccc(N3C[C@@H](F)C[C@@H]3c3cc(F)cc(C(=O)NCCO)c3)nc12] | or a pharmaceutically acceptable salt thereof.

7. The method of claim 1, wherein the compound is

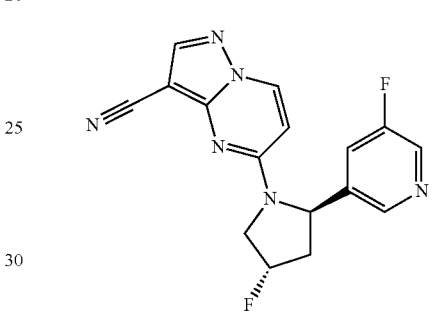

or a pharmaceutically acceptable salt thereof.

8. The method of claim 1, wherein the compound is

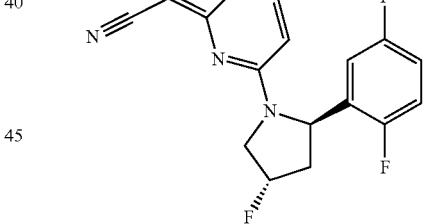

or a pharmaceutically acceptable salt thereof.

9. The method of claim 1, wherein the compound is

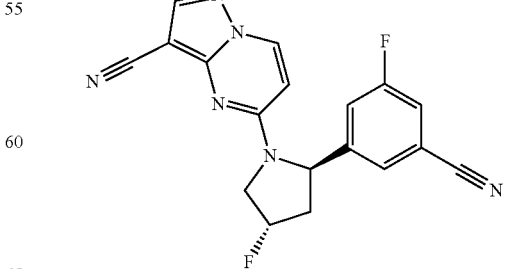

or a pharmaceutically acceptable salt thereof.

10. The method of claim 1, wherein the compound is

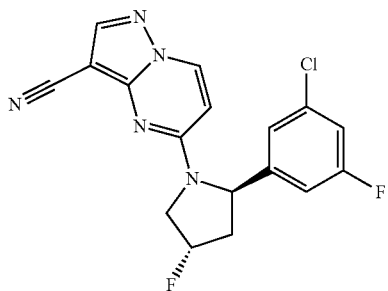 [SMILES: N#Cc1cnn2ccc(N3C[C@@H](F)C[C@@H]3c3cc(F)cc(Cl)c3)nc12]

or a pharmaceutically acceptable salt thereof.

11. The method of claim 1, wherein the compound is

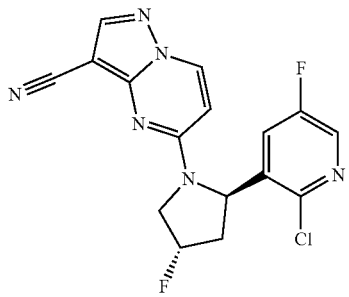 [SMILES: N#Cc1cnn2ccc(N3C[C@@H](F)C[C@@H]3c3cc(F)cnc3Cl)nc12]

or a pharmaceutically acceptable salt thereof.

12. The method of claim 1, wherein the tumor is from a cancer, wherein the cancer is selected from non-small cell lung cancer, breast cancer, melanoma, low and high grade glioma, glioblastoma, pediatric astrocytoma, colorectal cancer, thyroid cancer, pancreatic cancer, biliary cancer, head and neck cancer, primary CNS tumors, cholangiocarcinoma, breast cancer, salivary gland cancer, sarcoma, and spitzoid neoplasms.

13. The method of claim 1, wherein the tumor is characterized by the identification of an NTRK fusion.

14. The method of claim 13, wherein the kinase domain of the NTRK fusion has a mutation.

15. The method of claim 14, wherein the mutation is G595R.

16. The method of claim 12, wherein the cancer is non-small cell lung cancer.

17. The method of claim 12, wherein the cancer is thyroid cancer.

18. The method of claim 12, wherein the cancer is pancreatic cancer.

19. The method of claim 12, wherein the cancer is colorectal cancer.

* * * * *